US008597950B2

(12) United States Patent
Marillonnet et al.

(10) Patent No.: US 8,597,950 B2
(45) Date of Patent: Dec. 3, 2013

(54) TWO-COMPONENT RNA VIRUS-DERIVED PLANT EXPRESSION SYSTEM

(75) Inventors: Sylvestre Marillonnet, Halle (DE); Carola Engler, Halle (DE); Victor Klimyuk, Halle (DE); Yuri Gleba, Halle (DE)

(73) Assignee: Icon Genetics AG, Munich (DE)

( * ) Notice: Subject to any disclaimer, the term of this patent is extended or adjusted under 35 U.S.C. 154(b) by 1650 days.

(21) Appl. No.: 10/586,998

(22) PCT Filed: Jan. 19, 2005

(86) PCT No.: PCT/EP2005/000492
§ 371 (c)(1),
(2), (4) Date: Jul. 21, 2006

(87) PCT Pub. No.: WO2005/071090
PCT Pub. Date: Aug. 4, 2005

(65) Prior Publication Data
US 2007/0300330 A1    Dec. 27, 2007

(30) Foreign Application Priority Data

Jan. 23, 2004 (EP) .................................... 04001460

(51) Int. Cl.
*C12N 15/86* (2006.01)
*A61K 38/00* (2006.01)
*C12N 7/00* (2006.01)
*C07K 14/415* (2006.01)
*C07K 14/005* (2006.01)
*C07H 21/04* (2006.01)
*C12N 5/04* (2006.01)

(52) U.S. Cl.
USPC ........ 435/457; 800/280; 435/69.1; 435/320.1; 435/235.1; 435/419; 536/23.2; 536/23.72; 536/24.1

(58) Field of Classification Search
None
See application file for complete search history.

(56) References Cited

U.S. PATENT DOCUMENTS

| 5,811,653 | A * | 9/1998 | Turpen .......................... 800/294 |
| 6,384,207 | B1 * | 5/2002 | Ainley et al. ................. 536/24.1 |
| 6,632,980 | B1 | 10/2003 | Yadav et al. |
| 2007/0044170 | A1 | 2/2007 | Marillonnet et al. |

FOREIGN PATENT DOCUMENTS

| WO | WO 94/16089 | 7/1994 |
| WO | WO 99/22003 | 5/1999 |
| WO | WO 00/53780 | 9/2000 |
| WO | WO 02/088369 A1 | 11/2002 |
| WO | WO 02/097080 A2 | 12/2002 |

OTHER PUBLICATIONS

Lough et al 2001, Virology 288:18-28.*
Chakrabarty, R., et al., "*Agrobacterium*-mediated Transformation of Cauliflower: Optimization of Protocol and Development of Bt-transgenic Cauliflower," *J. Biosci.*, 2002, pp. 495-502, vol. 27(5), Indian Academy of Sciences.
Haseloff, J., et al., "Removal of a Cryptic Intron and Subcellular Localization of Green Fluorescent Protein are Required to Mark Transgenic *Arabidopsis* Plants Brightly," *Proc. Natl. Acad. Sci. USA*, 1997, pp. 2122-2127, vol. 94, The National Academy of Sciences of the USA.
Koziel, M., et al., "Optimizing Expression of Transgenes with an Emphasis on Post-transcriptional Events," *Plant Molecular Biology*, 1996, pp. 393-405, vol. 32, Kluwer Academic Publishers, Belgium.
Mallory, Allison C., et al., "The Amplicon-plus System for High-level Expression of Transgenes in Plants," *Nature Biotechnology*, 2002, pp. 622-625 vol. 20.
Rose, A., "Requirements for Intron-mediated Enhancement of Gene Expression in *Arabidopsis*," *RNA*, 2002, pp. 1444-1453, vol. 8, RNA Society.
Simpson, C.G., et al., "Expression of a Heterologous Gene Can be Improved by Mutation of Cryptic Splice Sites," *Annual Meeting of the Society for Experimental Biology*, St. Andrews Scotland, UK, 1995, p. 38, vol. 46.
Simpson, C.G. and J.W.S. Brown, "Efficient Splicing of an AU-rich Antisense Intron Sequence," *Plant Molecular Biology*, 1993, 205-211, vol. 21, Kluwer Academic Publishers, Belgium.
Knapp, E., et al., "Conundrum of the Lack of Defective RNAs (dRNAs) Associated with Tobamovirus Infections: dRNAs That Can Move Are Not Replicated by the Wild-Type Virus; dRNAs That Are Replicated by the Wild-Type Virus Do Not Move," *Journal of Virology*, 2001, pp. 5518-5525, vol. 75(12), American Society for Microbiology.
Lough, T., et al., "Trans-Complementation of Long-Distance Movement of *White Clover Mosaic Virus* Triple Gene Block (TGB) Mutants: Phloem-Associated Movement of TGBp1" *Virology*, 2001, pp. 18-28, vol. 288, Academic Press.

* cited by examiner

*Primary Examiner* — Li Zheng
*Assistant Examiner* — Stephen Uyeno
(74) *Attorney, Agent, or Firm* — Alston & Bird LLP

(57) ABSTRACT

A process for replicating or for replicating and expressing a sequence of interest in a plant, comprising: (i) an RNA replicon or a precursor thereof, said RNA replicon being derived from a plus-sense single stranded RNA virus and comprising at least one sequence of interest; and (ii) a helper replicon, or a precursor thereof, wherein said helper replicon is (a) incapable of systemic movement in said plant both in the presence and in the absence of said RNA replicon (i) and (b) capable of expressing in a plant one or more proteins necessary for systemic movement of said RNA replicon (i), whereby said RNA replicon (i) is capable of replicating or replicating and expressing said sequence of interest in said plant, but unable to move systemically in said plant in the absence of said one or more proteins expressed by said helper replicon (ii).

26 Claims, 14 Drawing Sheets pICH16888 transformants infiltrated with pICH14313 providing integrase pICH12691 transformants infiltrated with pICH10881 providing integrase
Line 6    Line 10

TWO-COMPONENT RNA VIRUS-DERIVED PLANT EXPRESSION SYSTEM

FIELD OF THE INVENTION

The present invention relates to a viral vector system for replicating or for expressing a sequence of interest in a plant. The invention also provides a process for replicating and/or expressing a sequence of interest in a plant. This process can be used for expressing a protein of interest in plants, notably in crop plants. The system can be based on a large variety of different viral vectors.

BACKGROUND OF THE INVENTION

Virus-based expression systems can be used for rapid protein production in plants (for review see: Porta & Lomonossoff, 1996, *Mol. Biotechnol.*, 5, 209-221; Yusibov et al., 1999, *Curr. Top. Microbiol. Immunol*, 240, 81-94) and are a powerful tool for functional genomics studies (Dalmay et al., 2000, *Plant Cell*, 12, 369-379; Ratcliff et al., 2001, *Plant J.*, 25, 237-245; Escobar et al., 2003, *Plant Cell*, 15, 1507-1523). Numerous publications and patents in the field describe systems based on DNA and RNA viral vectors (Kumagai et al., 1994, *Proc. Natl. Acad. Sci. USA*, 90, 427-430; Mallory et al., 2002, *Nature Biotechnol.* 20, 622-625; Mor et al., 2003, *Biotechnol. Bioeng.*, 81; 430-437; U.S. Pat. Nos. 5,316,931; 5,589,367; 5,866,785; 5,491,076; 5,977,438; 5,981,236; WO02088369; WO02097080; WO9854342). The existing viral vector systems are usually restricted to a narrow host range in terms of their best performance and even the expression level of such vectors in their most favourable host is far below the upper biological limits of the system.

RNA viruses are the most suitable for use as expression vectors, as they offer a higher expression level compared to DNA viruses. There are several published patents which describe viral vectors suitable for systemic expression of transgenic material in plants (U.S. Pat. Nos. 5,316,931; 5,589,367; 5,866,785). In general, these vectors can express a foreign gene as a translational fusion with a viral protein (U.S. Pat. Nos. 5,491,076; 5,977,438), from an additional subgenomic promoter (U.S. Pat. Nos. 5,466,788; 5,670,353; 5,866,785), or from polycistronic viral RNA using IRES elements for independent protein translation (WO0229068). The first approach—translational fusion of a recombinant protein with a viral structural protein (Hamamoto et al., 1993, *BioTechnology*, 11, 930-932; Gopinath et al., 2000, *Virology*, 267, 159-173; JP6169789; U.S. Pat. No. 5,977,438) gives significant yield. However, the use of such an approach is limited, as the recombinant protein cannot be easily separated from the viral one. One of the versions of this approach employs the translational fusion via a peptide sequence recognized by a viral site-specific protease or via a catalytic peptide (Dolja et al., 1992, *Proc. Natl. Acad. Sci. USA*, 89, 10208-10212; Gopinath et al., 2000, *Virology*, 267, 159-173; U.S. Pat. Nos. 5,162,601; 5,766,885; 5,491,076).

Expression processes utilizing viral vectors built on heterologous subgenomic promoters provide a good level of protein production (U.S. Pat. No. 5,316,931). The most serious disadvantage of such vectors and many others is their limited capacity with regard to the size of DNA to be amplified. Usually, stable constructs accommodate inserts of not more than one kb. In some areas of plant functional genomics this may not be such a serious limitation as G. della-Cioppa et al. (WO993651) described the use of TMV-based viral vectors to express plant cDNA libraries with the purpose of silencing endogenous genes. Additionally, as such vectors are capable of systemic movement and produce coat protein, significant resources of the plant are diverted from the synthesis of recombinant protein. The low expression levels achieved so far with such plant viral expression systems are a major reason why these systems are hardly competitive with other expression systems like bacterial, fungal, or insect cell expression systems. Low expression levels give rise to very high downstream costs for protein isolation and purification in a huge background of plant material. Therefore, costs for downstream processing quickly decrease, as the yield of the protein or product of interest per unit plant biomass increases. Also, a biological safety of such vectors are an issue, as they are able to form infectious viral particles.

An alternative two-component system requiring a helper virus was developed by Turpen (U.S. Pat. No. 5,811,653; U.S. Pat. No. 5,889,191; U.S. Pat. No. 5,965,794); this approach relies on a system of a virus and a helper virus, whereby the helper virus provides a replicase function, whereas the main replicon is deficient in replicase activity. This system is not practical because viral RNA-dependent RNA polymerase (replicase) works inefficiently with substrate RNAs provided in trans. A possible explanation of such inefficiency is that TMV RNA-dependent RNA polymerase is a heterodimer consisting of a 126 kDa protein and a 183 kDa read-through protein (Watanabe et al., 1999, *J. Virol.* 73, 2633-2640). It was shown that at least one component of this heterodimer, the 126 kDa protein, appeared to work primarily in cis (Lewandowsky & Dawson, 2000, *Virology*, 271, 90-98). There are several publications concerning the complementation in trans of other viral functions, like cell-to cell and systemic movement. The MP and CP can be provided in trans either by a transgenic host or by another virus. For example, mutants of TMV with frameshifts within the MP or CP gene were unable to locally or systemically infect inoculated tobacco plants, but acquired the lost functions in transgenic tobacco plants expressing the wild-type MP or CP gene (Holt & Beachy, 1991, *Virology*, 181, 109-117; Osbourn, Sarkar & Wilson, 1990, *Virology*, 179, 921-925). These works did not address the issue of creating virus-based vectors for expressing a heterologous sequence of interest, but rather studied the biological functions of different viral proteins. Another work describes the complementation of long distance movement of a CP-deficient TMV expressing GFP by a chimeric TMV carrying ORF3 of groundnut rosette umbravirus (GRV) (Ryabov, Robinson & Taliansky, 1999, *Proc. Natl. Acad. Sci. USA*, 96, 1212-12170). However, as it follows from the results, the efficiency of GFP expression in systemic leaves of plants co-infected with CP-deficient TMV expressing GFP and TMV having CP replaced by ORF3 of GRV was significantly lower than in plants infected with systemic TMV expressing GFP. It appears that this low expression level may be due to the presence and competition of both viral vectors in systemic leaves. Moreover, all experiments mentioned above led to the formation of infectious viral particles in systemic leaves and are therefore not acceptable for use in the environment from the point of view of biological safety.

Another system proposed by C. Masuta et al. (U.S. Pat. No. 5,304,731) proposes to use a satellite CMV RNA virus to be used as a carrier of the heterologous sequence of interest, and a helper virus that provides functions necessary for CMV RNA replication. To the best of our knowledge, the system is highly inefficient.

A serious concern with prior art virus-based plant expression systems is biological safety. On the one hand, high infectivity of the recombinant virus is highly desired in order to facilitate spread of the virus throughout the plant and to neighbouring pl desired gene product. On the other hand, such a high infectivity compromises containment of the recombinant material since spread to undesired plants can easily occur. Consequently, safer virus-based plant expression systems are highly desired.

There is presently no biologically safe large-scale transgene expression system built on plant RNA viral vectors capable of moving systemically and providing for the yield and efficiency required for technical applications. The existing systemic vectors suffer from a low yield of recombinant product.

Therefore, it is an object of this invention to provide an environmentally safe plant viral expression system for high-yield production of a protein of interest. It is another object of the invention to provide a process of replicating and/or expressing a nucleotide sequence of interest in a plant or plant part, which is of improved ecological and biological safety. It is another object to provide a process of protein production in plants having efficiency enabling competitive large-scale protein production in plants.

GENERAL DESCRIPTION OF THE INVENTION

The above objects are solved by a system for replicating or for replicating and expressing a sequence of interest in a plant, comprising:
(i) an RNA replicon or a precursor thereof, said RNA replicon being derived from a plus-sense single stranded RNA virus and comprising at least one sequence of interest; and
(ii) a helper replicon, or a precursor thereof, wherein said helper replicon is
  (a) incapable of systemic movement in said plant both in the presence and in the absence of said RNA replicon (i) and
  (b) capable of expressing in a plant one or more proteins necessary for systemic movement of said RNA replicon (i),
whereby said RNA replicon (i) is capable of replicating or replicating and expressing said sequence of interest in said plant, but unable to move systemically in said plant in the absence of said one or more proteins expressed by said helper replicon (ii).

The invention further provides a process of replicating or of replicating and expressing a sequence of interest in a plant, comprising providing cells of said plant with said RNA replicon (i) and said helper replicon (ii). The invention may be used for replicating a sequence of interest in a plant or for replicating a sequence of interest and expressing said sequence of interest, e.g. for producing a protein of interest like an industrial enzyme or a pharmaceutical protein in said plant. The invention also relates to proteins produced or producible by the process of the invention. Further, the invention provides a process of protein production in plants or in plant cells.

In important embodiments, said RNA replicon (i) and/or said helper replicon (ii) are provided to a plant via DNA precursors that are introduced into cell nuclei of said plant. These DNA precursors can generate the RNA replicon (i) and/or the helper replicon (ii) by transcription in cell nuclei. For improving formation and build-up of RNA replicon (i) and/or helper replicon (ii) in the cell cytoplasm, said precursor of said RNA replicon (i) and/or said precursor of said helper replicon (ii) may contain one or more introns. Generally, the DNA precursor of said RNA replicon (i) and/or the DNA precursor of said helper replicon (i) contain sequences for replicon function (like a replicase ORF or an MP ORF in the case of said RNA replicon (i)) being derived from sequences of an RNA virus, said sequences for replicon function preferably exhibiting at selected localities of said sequence of said RNA virus function-conservative differences from said sequence of said RNA virus, said differences causing an increased frequency of RNA replicon (i) and/or helper replicon (ii) formation compared to an RNA replicons not exhibiting said differences. This technology is described in detail in PCT/EP04/012743 for one RNA replicon and may be applied in the present invention to said RNA replicon (i) and to said helper replicon (ii).

The inventors have surprisingly identified a novel principle for replicating or for replicating and expressing a sequence of interest in a plant. The inventors have found that a helper replicon that is deficient in the ability to assemble virus particles, e.g. when provided to a plant by agrodelivery as a DNA copy, can express a sufficient amount of coat protein in locally transfected tissue to fully restore systemic movement of the said RNA replicon (i). It was further found that systemic movement of said RNA replicon (i) results in systemically infected leaves that express the sequence of interest but have a greatly reduced amount of coat protein compared with the case where a coat protein-expressing virus expresses a sequence of interest. The coat protein is usually the strongest expressed protein in virus-infected plant cells. With the system and process of the invention, however, resources of systemically infected cells are not used up by coat protein expression. Consequently, the expression levels of said sequence of interest in systemically infected plant cells are higher than in conventional viral expression systems. Further, systemically infected plant cells produce small amounts of assembled viral particles from said RNA replicon (i), whereby spread of the RNA replicon (i) to secondary host plants occurs with very low probability. If spreading of said RNA replicon (i) to an undesired plant occurs in a rare event, it cannot move systemically in such an undesired plant due to the absence of said helper replicon and poses therefore a negligible environmental risk. Thus, the system and process of the invention are of excellent biological/environmental safety. At the same time, the system and process of the invention maintain the important feature of viral expression systems that infection of a part of a plant is sufficient to achieve replication or replication and expression of a sequence of interest in other parts of the plant, preferably in the whole plant.

The advantageous features of the invention may be summarized as follows:
1. The system provides for systemic infection of the host plant by an RNA replicon that does not have a coat protein, and thus can accommodate larger DNA inserts.
2. The expression in systemic leaves is totally dedicated to the heterologous sequence of interest, and there is no or little competition with the expression of coat protein.
3. Because of the low amount of viral proteins (coat protein is present in low amounts as it is produced by the helper replicon in the locally infected leaf) and of the host proteins (due to shut off of the biosynthetic machinery of plant cell), the highest absolute and relative yield of protein of interest or RNA of interest can be achieved.
4. The yield of assembled viral particles is very low, and the assembled virus particles have no protein(s) necessary for systemic movement, thus the expression system is much more safe, than a vector that retains all functions of the wild type virus.
5. Incorporation of introns or other function-conservative differences as defined herein in the DNA precursor of the RNA replicon (i) and optionally also in the helper replicon (ii) improves the efficiency of RNA replicon (and optionally of helper replicon) build up in the cytosol, which provides the efficiency required for a competitive industrial/large scale protein production process.

Further modifications of the RNA replicon (i) and of the helper replicon (ii) are described herein that minimize the risk of wild type virus reconstruction due to recombination between said RNA replicon (i) and said helper replicon (ii). Further, the invention has no detectable limit of the size of the sequence of interest to be expressed, it allows expressing multiple genes in the same cell and plant and it possesses high ecological and biological safety parameters.

The system and process of the invention can be used for replicating or for replicating and expressing a sequence of interest. Replicating refers to RNA production, namely amplification of said sequence of interest together with said RNA replicon (i). Expressing refers to the production of a protein of interest encoded in said sequence of interest. Preferably, the system and process of the invention is used for producing a protein of interest from a sequence of interest present in said RNA replicon (i).

The system of the invention may comprise said RNA replicon (i) and said helper replicon (ii). Preferably, said system comprises a DNA precursor of said RNA replicon (i) and a DNA precursor of said helper replicon (ii). More preferably, said DNA precursors are contained in T-DNA of Agrobacterial Ti plasmids. Most preferably, said system of the invention is a mixture of two Agrobacterium strains, one strain containing in T-DNA said DNA precursor of said RNA replicon (i), the other strain containing in T-DNA said DNA precursor of said helper replicon (ii). The system of the invention may be a kit for producing a protein of interest, said kit containing any of the replicon pairs, precursor pairs, or mixture of two Agrobacterium strains mentioned in this paragraph. Said kit may further contain a plant or seeds of a plant in which said sequence of interest is to be expressed. Further, the system of the invention may be a plant treated, infected or transformed with any of the replicon pairs, precursor pairs, or mixture of two Agrobacterium strains.

A first component of the system (or kit) of the invention comprises said RNA replicon (i). Said RNA replicon (i) is typically derived from a plus-sense single stranded RNA virus. Examples of such viruses are cowpea mosaic virus, potato virus X, and alfalfa mosaic virus. Preferred viruses are tobamoviruses, the most preferred ones being tobacco mosaic virus (TMV) and crucifer-infecting tobamovirus. Being derived from a plus-sense single stranded RNA virus means that said RNA replicon (i) is typically created using such a virus as a starting material. Alternatively, said RNA replicon (i) may be created using genetic functions (e.g. replicase, movement protein) from such a virus. Said RNA replicon (i) can also be created using components or genetic functions from different plus-sense single stranded RNA viruses. Said precursor of said RNA replicon (i) may be a DNA precursor encoding said RNA replicon (i), and said DNA precursor is capable of producing said RNA replicon (i) in cells of said plant. As further explained below, said DNA precursor of said RNA replicon (i) may contain one or more introns; or may have been modified relative to the virus it is derived from by changing the codon usage e.g. for removing splicing sites splicing at which would destroy the replicon capabilities of the RNA replicon.

For being a replicon, said RNA replicon (i) has to be capable of replicating autonomously in a plant cell. Autonomous replication means that the replicon codes for a replicase (RNA-dependent RNA polymerase) catalyzing replication of the replicon. A replicon may make use of functions of the host cell like the translation machinery needed for translating said replicase. Said replicase may be provided with one or several introns, notably if said RNA replicon (i) is provided as a DNA precursor to plant cell nuclei, for increasing the efficiency of RNA replicon build-up in the cytoplasm (cf. PCT/EP03/12530 and PCT/EP04/012743 that are incorporated herein by reference).

Further, said RNA replicon (i) contains said sequence of interest to be replicated or expressed. Preferably, said sequence of interest is expressed in the process of the invention to produce a protein of interest. Said sequence of interest is preferably heterologous to said plus-sense single-stranded RNA virus(es) from which said RNA replicon (i) is derived. Said RNA replicon (i) generally contains further genetic functions needed for expressing or replicating said sequence of interest like one or more subgenomic promoters, ribosome binding sites etc.

Said RNA replicon (i) is unable to move systemically in said plant in the absence of said one or more proteins expressed by said helper replicon (ii). This property can be achieved by modifying the nucleotide sequence encoding the protein necessary for systemic movement of said RNA virus from which said RNA replicon (i) is derived such that this protein cannot be expressed in a functional form from said RNA replicon (i). Expression in a functional form may be prevented by mutating or deleting parts of the sequence coding for said protein, or by mutating or deleting regulatory sequences (e.g. a subgenomic promoter) required for expressing said protein. In a preferred embodiment, said protein (or said proteins if said RNA virus contains more than one protein needed for systemic movement) is largely or totally deleted. Such a deletion adds several additional advantages to the system and process of the invention: Larger sequences of interest can be included in said RNA replicon (i) without compromising the efficiency of said RNA replicon (i), whereby said sequence of interest may be larger than 1 kb. Further, the homology between said RNA replicon (i) and said helper replicon (ii) is reduced. Thereby, recombination events between said replicons (i) and (ii) are unlikely.

In many plant viruses like tobamoviruses, said protein necessary for systemic movement is the coat protein. Thus, said RNA replicon (i) preferably does not contain a coat protein open reading frame (ORF) or lacks substantial parts of a coat protein ORF. Instead, said sequence of interest may take the position of the coat protein ORF. This position is 3'-proximal in many plant viruses, which is generally the position of the viral ORF that is expressed the strongest.

In order to be able to move systemically in said plant in the presence of said helper replicon, said RNA replicon (i) has to have a functional origin of viral particle assembly. In the case of tobamoviruses, the origin of viral particle assembly is located in the movement protein (MP) ORF. It is thus preferred that said RNA replicon (i) contains the sequence segment or ORF that harbors the origin of viral particle assembly in the RNA virus from which said RNA replicon (i) is derived.

The second component of the system and process of the invention is said helper replicon (ii). Said helper replicon (ii) helps said RNA replicon (i) in that it is capable of expressing in a plant one or more proteins necessary for systemic movement of said RNA replicon (i). The helper replicon (ii) may provide in said plant any protein or proteins that enable(s) said RNA replicon (i) to move systemically in said plant. Preferably, said protein necessary for systemic movement corresponds to that deleted or rendered unexpressible in said RNA replicon (i). Most preferably, it is a coat protein.

Said helper replicon (ii) may be a DNA replicon and may be derived from a DNA virus like gemini virus. Preferably, however, said helper replicon (ii) is an RNA replicon and may be derived from an RNA virus like a plus-sense single stranded RNA virus. Said helper replicon (ii) and said RNA replicon (i) may be derived from the same or from different plant viruses, e.g. from a tobamovirus like tobacco mosaic virus. Similarly as said RNA replicon (i), said helper replicon (ii) codes for a replicase capable of catalyzing replication of said helper replicon in plant cells.

Said helper replicon (ii) is incapable of systemic movement in said plant, independent of whether said RNA replicon (i) is present or absent in said plant. Being incapable of systemic movement may be achieved in various ways. In one embodiment, said helper replicon (ii) and said protein necessary for systemic movement are incompatible such that said protein necessary for systemic movement of said RNA replicon (i) cannot provide said helper replicon with the functionality of systemic movement. In this case, said RNA replicon (i) and said helper replicon (ii) are preferably derived from different plant viruses, and the helper replicon (ii) may be capable of expressing a coat protein that provides said RNA replicon (i) but not said helper replicon (ii) with the systemic movement functionality. Alternatively, said RNA replicon (i) and said helper replicon (ii) are derived from the same plant virus.

In a preferred embodiment said helper replicon (ii) is incapable of systemic movement due to lacking a functional origin of viral particle assembly. Thereby, the helper replicon (ii) cannot be packaged by said protein necessary for systemic movement, notably said coat protein. The origin of viral particle assembly may be rendered dysfunctional. In TMV, the origin of viral particle assembly is located in the movement protein (MP) ORF. The origin of viral particle assembly in the MP ORF may also be deleted. It is not required that the MP ORF of said helper replicon (ii) codes for a functional MP. If a functional MP for said helper replicon (ii) is desired, the MP may for example be provided by said RNA replicon (i); further, the MP may also be encoded by a plant host transgenic for MP. If the origin of viral particle assembly is located in the MP ORF, it is most preferred that said helper replicon lacks the MP ORF. This has the additional advantage that homology between a RNA replicon (i) having an MP ORF and the helper replicon (ii) is reduced, providing improved biologically safety to the system and process, since the probability of formation of wild-type like RNA virus by homologous recombination is negligible.

Whether said helper replicon (ii) is capable or incapable of systemic movement can be tested experimentally (cf. examples) by infecting a portion of a leaf of a plant with said replicon (or a precursor thereof) and observing the occurrence of the same replicon in other, non-infected, leaves ("systemic leaves") of this plant. Being incapable of systemic movement is a relative property. Said helper replicon (ii) is considered to be incapable of systemic movement if the probability of systemic movement is substantially reduced compared to the virus it is derived from. In any case, the probability of systemic movement of said helper replicon (ii) is considerably lower than that of said RNA replicon (i), such that replication or replication and expression of said sequence of interest from said RNA replicon (i) in systemic leaves is not suppressed in systemic leaves in the typical time-frame of protein expression with plant viral expression systems (about 1 to 3 weeks). Most preferably, no systemic movement of said helper replicon (ii) in said plant is detectable (e.g. by Western or Northern blotting).

The plant used in the process or the system of the invention does preferably not contain a gene coding for a protein enabling systemic movement of said RNA replicon (i) or said helper replicon (ii), said gene being stably integrated into a nuclear chromosome of the plant. Such a situation would compromise biological safety of the process or system.

For improving the environmental safety and the efficiency of the system, said RNA replicon (i) and said helper replicon (ii) should not be prone to recombination with each other. This may be achieved by having a low homology between said replicons (i) and (ii). Preferably, said RNA replicon (i) and said helper replicon (ii) lack homology in functionally overlapping regions or do not overlap. Functionally overlapping regions are regions in said replicons having or coding for the same function, e.g. the replicase ORF, the MP ORF, or subgenomic promoters. Homology in such regions may be reduced e.g. by changing codons using the degeneracy of the genetic code and/or by using functional regions for said replicon (i) and (ii) that derive from different plant viruses.

Many potential recombination events do not change said replicons or lead to unfunctional replicons, depending on the specific replicons. Such recombinations may reduce the efficiency of the system but do not pose an environmental risk. For achieving the best environmental safety, said RNA replicon (i) and said helper replicon (ii) preferably lack a recombination-prone homology in a region, wherein recombination between said RNA replicon (i) and said helper replicon (ii) would create a replicon capable of, at the same time, (A) expressing a protein necessary for systemic movement and
(B) moving systemically in a plant.

Such a replicon would be comparable to viral vectors in conventional plant viral expression systems. The skilled person can easily identify such regions. In an embodiment wherein both replicons (i) and (ii) are based on tobamoviruses and said helper replicon (ii) lacks a functional origin of viral particle assembly, such a region is that downstream of the location in the MP ORF where the origin of assembly was deleted or rendered unfunctional. In this region, the homology between said RNA replicon (i) and said helper replicon (ii) should be reduced. Since in TMV the 3' part of the MP ORF and the 5' part of the CP subgenomic promoter overlap and in some strains the MP ORF further contains a part of the CP ORF, the possibilities of changing the codon usage is limited for reducing the homology, since this may impair the function of the CP subgenomic promoter. Instead of changing the codon usage, functional replacement may be used, i.e. the use of functional elements that derive from different viruses like a subgenomic promoter from different RNA viruses. Examples of such subgenomic promoters are the CP subgenomic promoters from TMV strains U1 and U5 or the CP subgenomic promoter of crTMV (crucifer-infecting tobamovirus). As an example, the CP in the helper replicon may be under control of the CP subgenomic promoter from TMV strain U1 and the sequence of interest in the RNA replicon (i) may be under control of the CP subgenomic promoter from crTMV or TMV strain U5, or vice versa. In any case, both the subgenomic promoter of the sequence of interest in the RNA replicon (i) and the subgenomic promoter of the CP in the helper replicon should be CP subgenomic promoters. In such an embodiment, the helper virus (ii) may be based on a tobamovirus (TMV) and may contain, in 5' to 3' direction, (a) tobamoviral replicase ORF(s), a CP subgenomic promoter, and, operately linked thereto, a coat protein necessary for systemic movement of said RNA replicon (i), whereby the MP ORF with the origin of particle assembly will be essentially or fully deleted. As mentioned above, the subgenomic promoter for the coat protein in the helper replicon and the subgenomic promoter used in RNA replicon (i) for the sequence of interest or a movement protein are preferably from different TMV strains.

The sequence homology between said RNA replicon (i) and said helper replicon (ii) in any sequence segments having at least 100 nucleotides (preferably at least 150 nucleotides) should be at most 90%. Such sequence segments are preferably located downstream of the replicase ORFs of said RNA replicon (i) and said helper replicon (ii). Preferably, the sequence homology between said RNA replicon (i) and said helper replicon (ii) in sequence segments having at least 100 nucleotides (preferably at least 1550 nucleotides) is at most 80%. More preferably, the sequence homology between said RNA replicon (i) and said helper replicon (ii) in sequence segments having at least 100 nucleotides (preferably at least 150 nucleotides) is at most 70%. Most preferably, the sequence homology between said RNA replicon (i) and said helper replicon (ii) in sequence segments having at least 100 nucleotides (preferably at least 150 nucleotides) is at most 60%. In a highly preferred embodiment, these homology values apply to the sequence segment of the subgenomic promoter of the CP in the helper replicon (ii) and the subgenomic promoter of the sequence of interest in the RNA replicon (i).

The system of the invention thus contains at least said components (i) and (ii). The system of the invention may contain said RNA replicon (i) and/or said helper replicon (ii) in the form of a precursor from which said replicons (i) and (ii) are formed in cells of the plant. The precursor of said RNA replicon (i) will generally be DNA coding for said RNA replicon (i) and having a promoter functional in said plant for forming said RNA replicon (i) by transcription of said DNA in cells of said plant. Similarly, if said helper replicon (ii) is an RNA replicon (RNA replicon (ii)), the precursor of said helper-replicon (ii) may be DNA. Said DNA precursors may be flanked by T-DNA left and right border sequences and may be carried by agrobacteria. In a particularly preferred embodiment of the invention, said system of the invention comprises, in an *Agrobacterium*-carried T-DNA, a DNA precursor of said RNA replicon (i); and, in an *Agrobacterium*-carried T-DNA, a DNA precursor of said helper replicon (ii). Other precursors of said replicons (i) and (ii) for said system of the invention are DNA for biolistic transformation of said plant or for other transformation methods.

DNA precursors of said replicons typically have a sequence encoding said RNA replicon (i) and/or said helper replicon (ii) operably linked or linkable to a transcription promoter. If a DNA sequence encoding a replicon is operably linked to a transcription promoter, the transcription promoter may be a regulated promoter, like an inducible, tissue-specific or developmentally regulated promoter in order to make expression of said sequence of interest regulatable. More preferably, said promoter is a constitutive promoter. In this case, the process of the invention is switched on by applying said DNA precursors to said plant or parts thereof.

The system of the invention may further contain a plant or seeds thereof for carrying out the process of the invention. In principal, the invention may be carried out with any plant for which infectious viruses are known. Preferred are crop plants including monocot and dicot plants, whereby the latter are preferred. The invention is well-established with *Nicotiana* plants and may be applied to other plants of the family Solanaceae. *Nicotiana tabacum* and *N. benthamiana* are most preferred. These plants have the additional advantage that they typically do not enter the human food chain.

Said plant may be a wild-type plant or a transgenic plant. An MP gene stably and expressibly integrated in the genome of said plant may be used for complementing the MP function of said helper replicon (ii), as described above. A preferred MP for this purpose is the MP of tobacco mosaic virus.

Obviously, said plant used for the process of the invention, said RNA replicon (i), and said helper replicon (ii) have to be appropriately selected for giving a functional system. For example, said replicons (i) and (ii) have to be able to replicate in cells of said plants, the used MPs have to be functional for enabling cell-to-cell movement in said plant, the used coat protein has to able to provide systemic movement to said RNA replicon (i) in said plant, etc. These issues are familiar to people of skill in the art.

In the process of the invention, said RNA replicon (i) and said helper replicon (ii), or precursors thereof, are provided to cells of said plant. Said replicons (i) and (ii) may be provided directly to said plant, which may be as RNA molecules or as packaged viral particles. Alternatively, said RNA replicon (i) or said helper replicon (ii) or both said RNA replicon (i) and said helper replicon (ii) may be provided to said plant as DNA precursors of said RNA replicon (i) and/or said helper replicon (ii). The type of precursor depends on the type of transformation method to be used. Usable transformation methods are given below. A preferred transformation method is *Agrobacterium*-mediated transformation. In this case, said plant is provided with said RNA replicon (i) and/or said helper replicon (ii) by transfecting with agrobacteria containing in their T-DNA said precursor of said replicon (i) and/or with agrobacteria containing in their T-DNA said precursor of said helper replicon (ii).

When said plant is transformed with said RNA replicon (i) and said helper replicon (ii), or precursors thereof, a selected part of said plant should be treated with both replicons in order to allow complementation of said RNA replicon (i) by said helper replicon (ii). In the case of *Agrobacterium*-mediated transformation, this is most easily achieved by treating a selected part of said plant with a mixture of two *Agrobacterium* strains, one strain containing said RNA replicon (i) as a DNA precursor in T-DNA, and another strain containing said helper replicon (ii) as a DNA precursor in T-DNA. Since at least one of said replicons (i) and (ii) will generally be capable of cell-to-cell movement due to an MP, it is not absolutely required that a cell of said plants is transformed with both replicons (i) and (ii). For reasons of efficiency, it is, however, preferred that cells of said plant are transformed with both replicons (i) and (ii).

For making full use of the invention, selected parts of said plant like one or more leaves, preferably lower leaves, should be provided with said RNA replicon (i) and said helper replicon (ii) but not other parts of said plant. Other parts of said plants, notably systemic leaves, will then be reached by said RNA replicon (i) by way of systemic movement. Further, one or more plants may be sprayed with an *Agrobacterium* suspension containing two *Agrobacterium* strains (e.g. *A. tumefaciens* strains), one containing a DNA precursor of said RNA replicon (i) and the other containing a DNA precursor of said helper replicon (ii).

The plants that can be used for the process of the invention correspond to those that may be a component of the system of the invention.

Said replicated or expressed sequence of interest may be harvested from said plant by conventional means. These products may be isolated using the whole plant, i.e. plant material that was provided with said replicons (i) and (ii) and plant material that was not provided with said replicons (i) and (ii). Preferably, these products are harvested and isolated from plant parts that were not provided with said replicons (i) and (ii), like leaves systemically infected by said RNA replicon (i).

PREFERRED EMBODIMENTS

A system for replicating or for replicating and expressing a sequence of interest in a plant, comprising:

(i) Agrobacteria containing a T-DNA comprising a precursor of an RNA replicon, whereby said RNA replicon is derived from tobacco mosaic virus, lacks a functional coat protein coding sequence, and comprises at least one sequence of interest, said precursor of said RNA replicon preferably containing one or more introns e.g. in the replicase ORF, said precursor of said RNA replicon preferably containing one or more introns; and (ii) Agrobacteria containing a T-DNA comprising a precursor of a helper replicon derived from a tobamovirus, wherein said helper replicon
   (a) lacks a functional origin of viral particle assembly and is incapable of systemic movement in said plant and
   (b) is capable of expressing in said plant a tobacco mosaic virus coat protein necessary for systemic movement of said RNA replicon (i), whereby said RNA replicon (i) is capable of replicating or replicating and expressing said sequence of interest in said plant, but unable to move systemically in said plant in the absence of said tobacco mosaic virus coat protein expressed by said helper replicon (ii).

A process of expressing a sequence of interest in a *Nicotiana* plant, comprising co-transforming a leaf of said plant with a mixture of the Agrobacteria of the above system.

A process of expressing a interest in a plant, comprising providing cells of said plant with (i) Agrobacteria containing a T-DNA comprising a precursor of an RNA replicon, said RNA replicon being derived from a plus-sense single stranded RNA virus and comprising at least one sequence of interest, said DNA precursor of said RNA replicon containing one or more introns; and (ii) Agrobacteria containing a T-DNA comprising a precursor of a helper replicon, wherein said helper replicon is
   (a) incapable of systemic movement in said plant both in the presence and in the absence of said RNA replicon (i) and
   (b) capable of expressing in a plant one or more proteins necessary for systemic movement of said RNA replicon (i), whereby said RNA replicon (i) is capable of replicating or replicating and expressing said sequence of interest in said plant, but unable to move systemically in said plant in the absence of said one or more proteins expressed by said helper replicon (ii), wherein said precursor of said RNA replicon contains one or more introns; or sequences for replicon function of said RNA replicon (i), said sequences being derived from a sequence of said RNA virus, said sequences for replicon function exhibit at selected localities of said sequence of said RNA virus function-conservative differences from said sequence of said RNA virus, said differences causing an increased frequency of RNA replicon (i) formation compared to an RNA replicon not exhibiting said differences.

Act2—promoter of the *Arabidopsis* ACTIN2 gene; RdRp—viral RNA-dependent RNA polymerase; MP—viral movement protein; NTR—viral 3' non-translated region; CP—viral coat protein; Tnos—transcription termination region of nopalin synthase.

Figure 1:
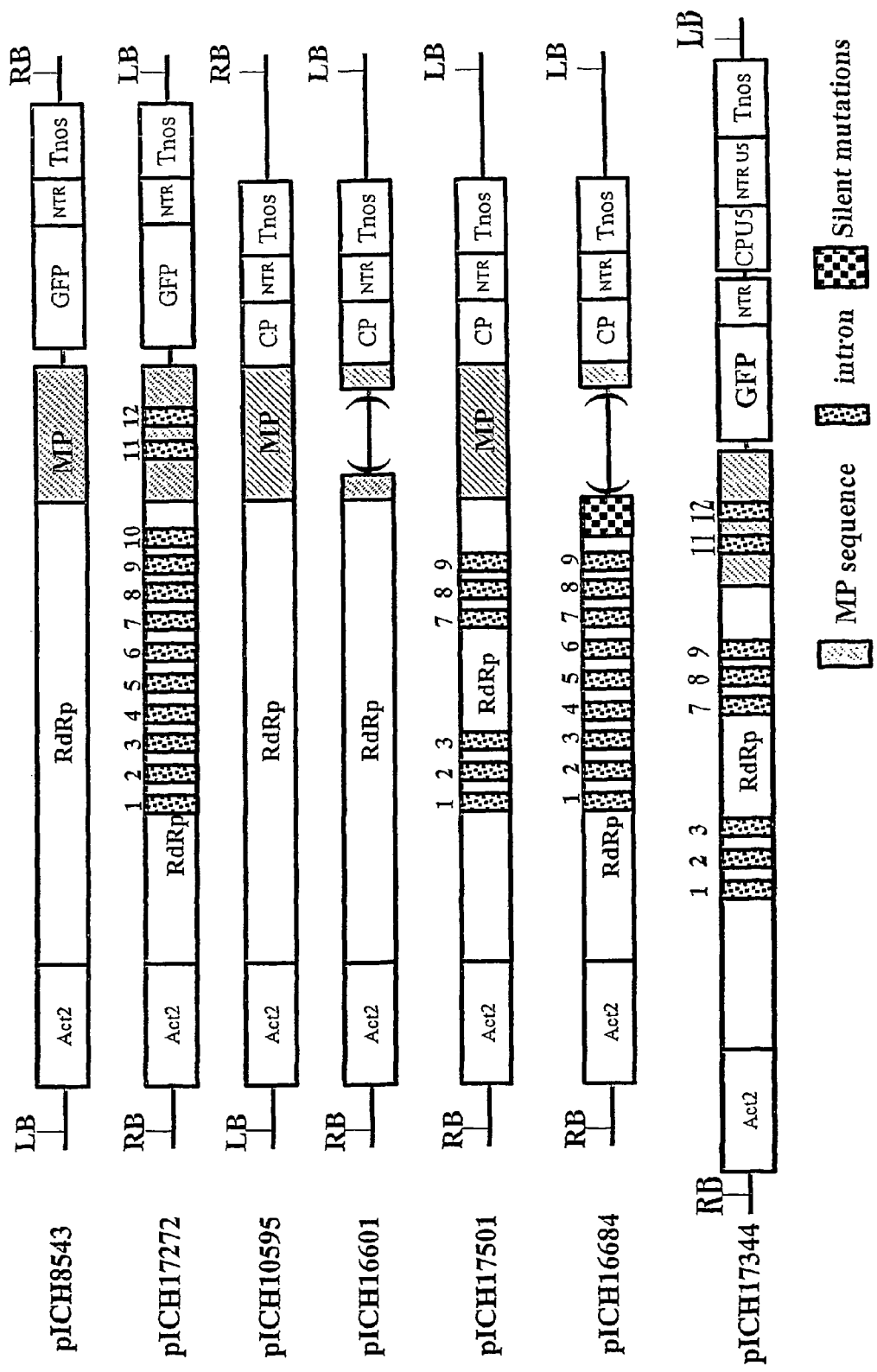
FIG. 1 depicts schemes of T-DNA regions for vectors pICH8543, pICH17272, pICH10595, pICH16601, pICH17501, pICH16684, pICH17344 designed for having an increased frequency of RNA virus-based replicon formation in plant cells. Some constructs contain introns which are numbered. The numbers correspond to the introns given in the annex. pICH8543, pICH17272, and pICH17344 are RNA replicons (i) according to the invention. pICH16601 and pICH16684 are helper replicons (ii) according to the invention.
Figure 2:

FIG. 2 shows systemic *N. benthamiana* leaves of two plants co-infiltrated with pICH17272 and pICH16684.

Figure 3:
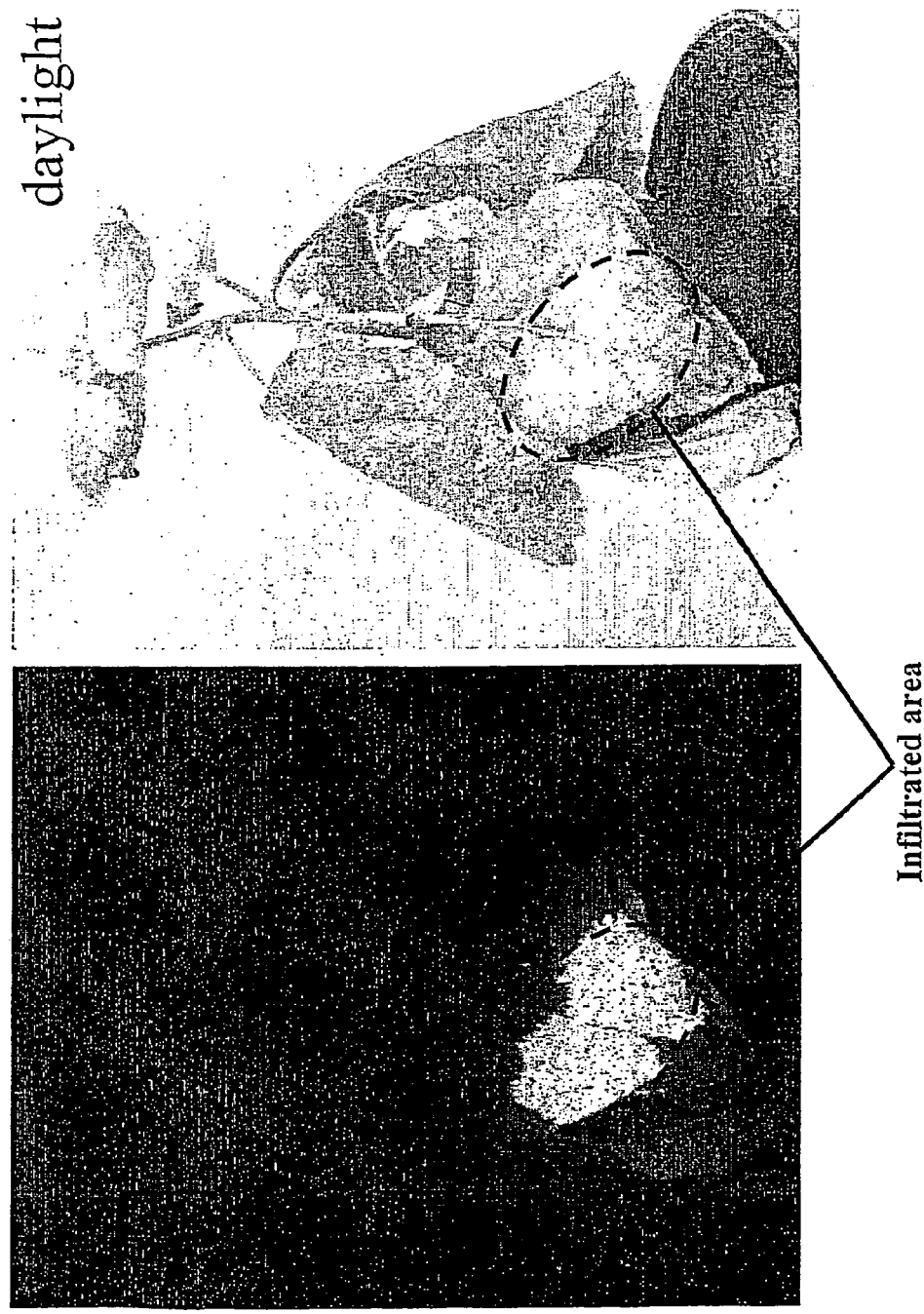

FIG. 3 shows an *N. benthamiana* plant co-infiltrated with pICH17272 and pICH17501. The left picture shows, under UV-light, the infiltrated area circled in the picture on the right hand side. GFP expression is found exclusively in the co-infiltrated area.

Figure 4:
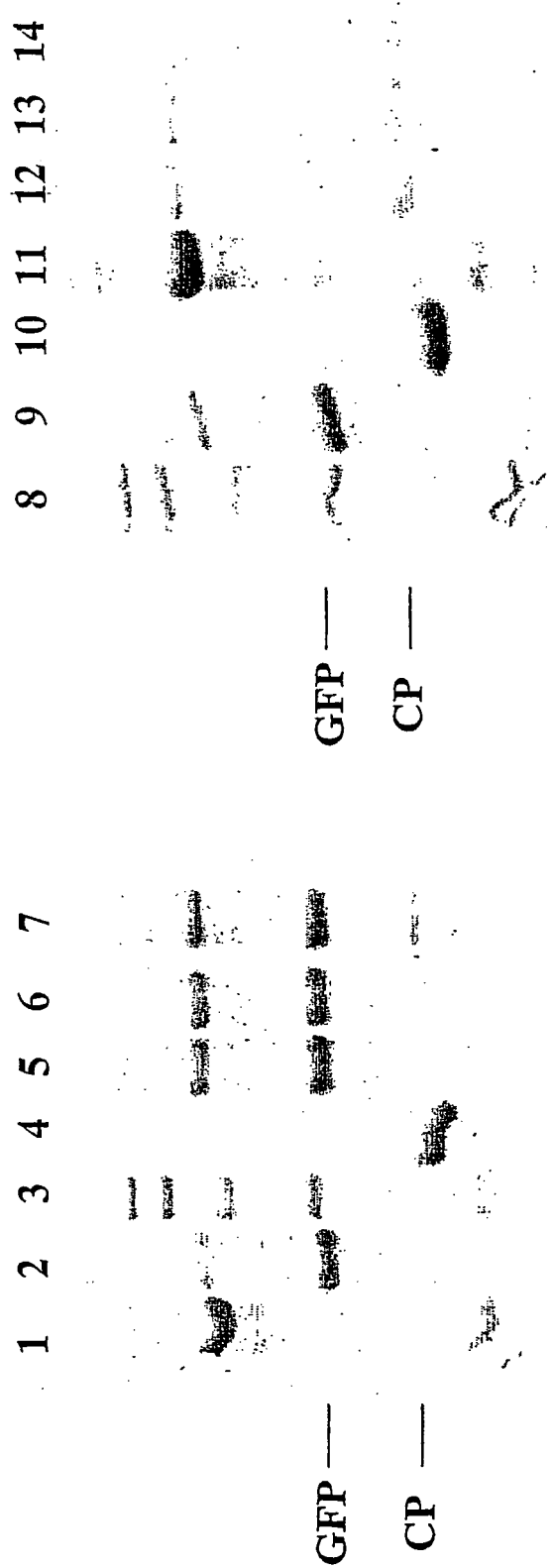
Figure 5:
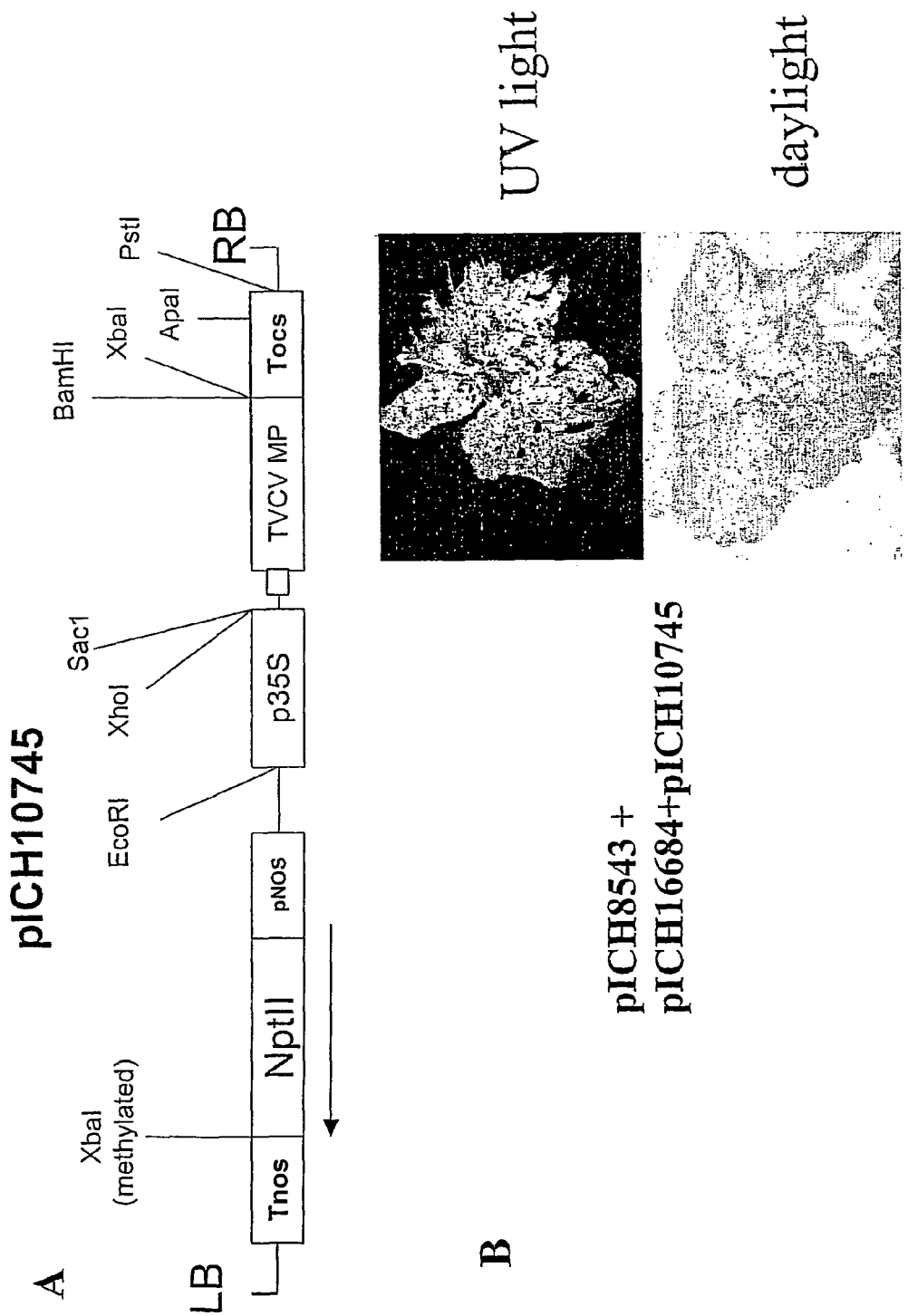

FIG. 4 shows SDS gel electrophoretic separation (coomassie stained) of total soluble proteins extracted from infiltrated and systemic leaves of *N. benthamiana*.
Lanes:
  1. pICH16601 upper non-infiltrated leaf tissue
  2. pICH8543 infiltrated area
  3. Molecular weight marker
  4. Systemic leaf of a plant infected with TVCV
  5,6. systemic leaf of plant co-infiltrated with pICH16684 and pICH17272
  7. systemic leaf of a plant co-infiltrated with pICH16601 and pICH17272
  8. Molecular weight marker
  9. pICH8543 infiltrated area
  10. Systemic leaf of a plant infected with TVCV
  11. pICH16601 upper non-infiltrated leaf tissue
  12 to 14. pICH17344, systemic leaf FIG. 5, is a schematic presentation of the T-DNA region of vector pICH10745 (A) and systemic *N. benthamiana* leaves of a plant co-infiltrated with pICH8543, pICH16684, and pICH10745.

Figure 6A:
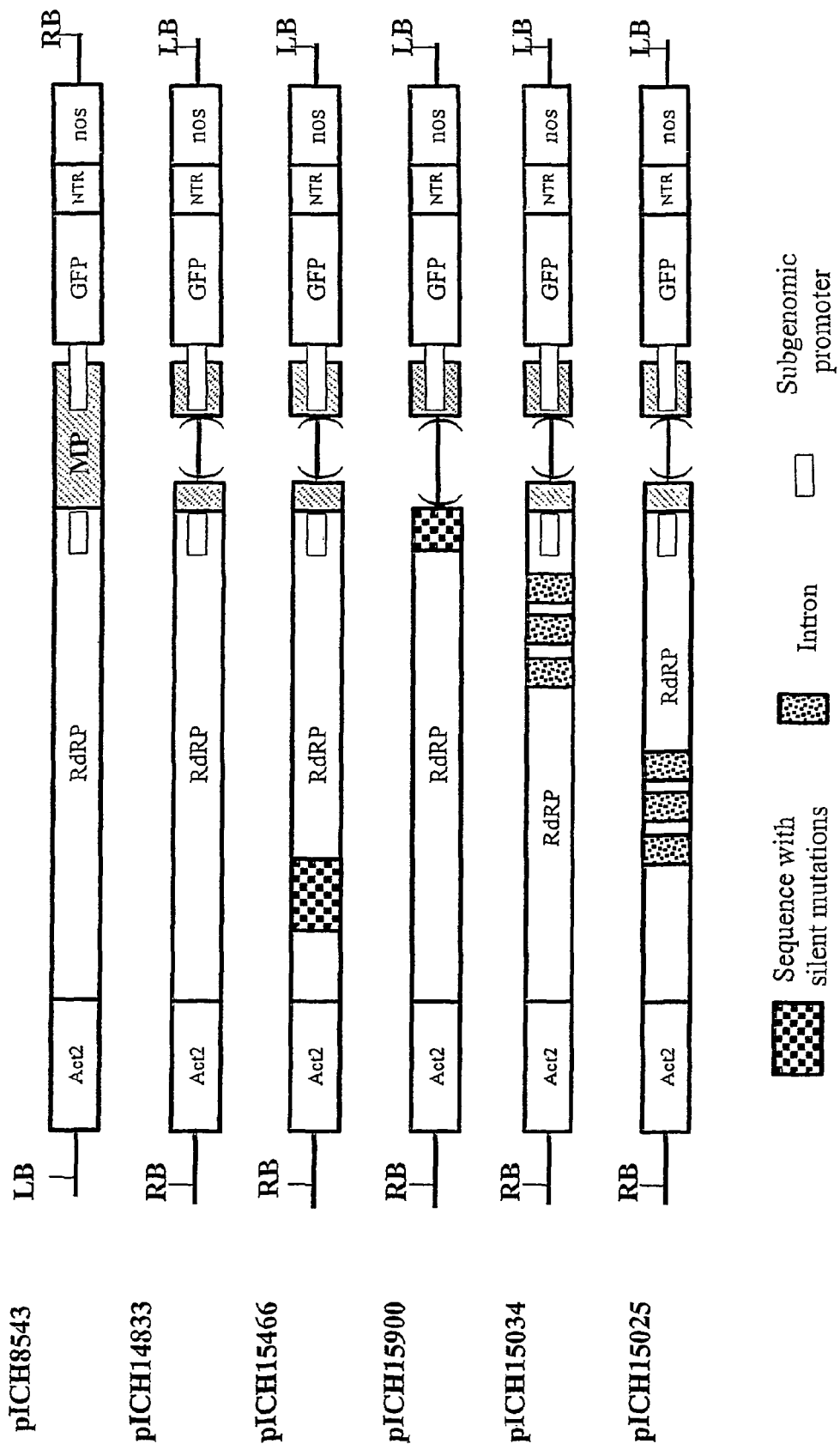
Figure 6B:
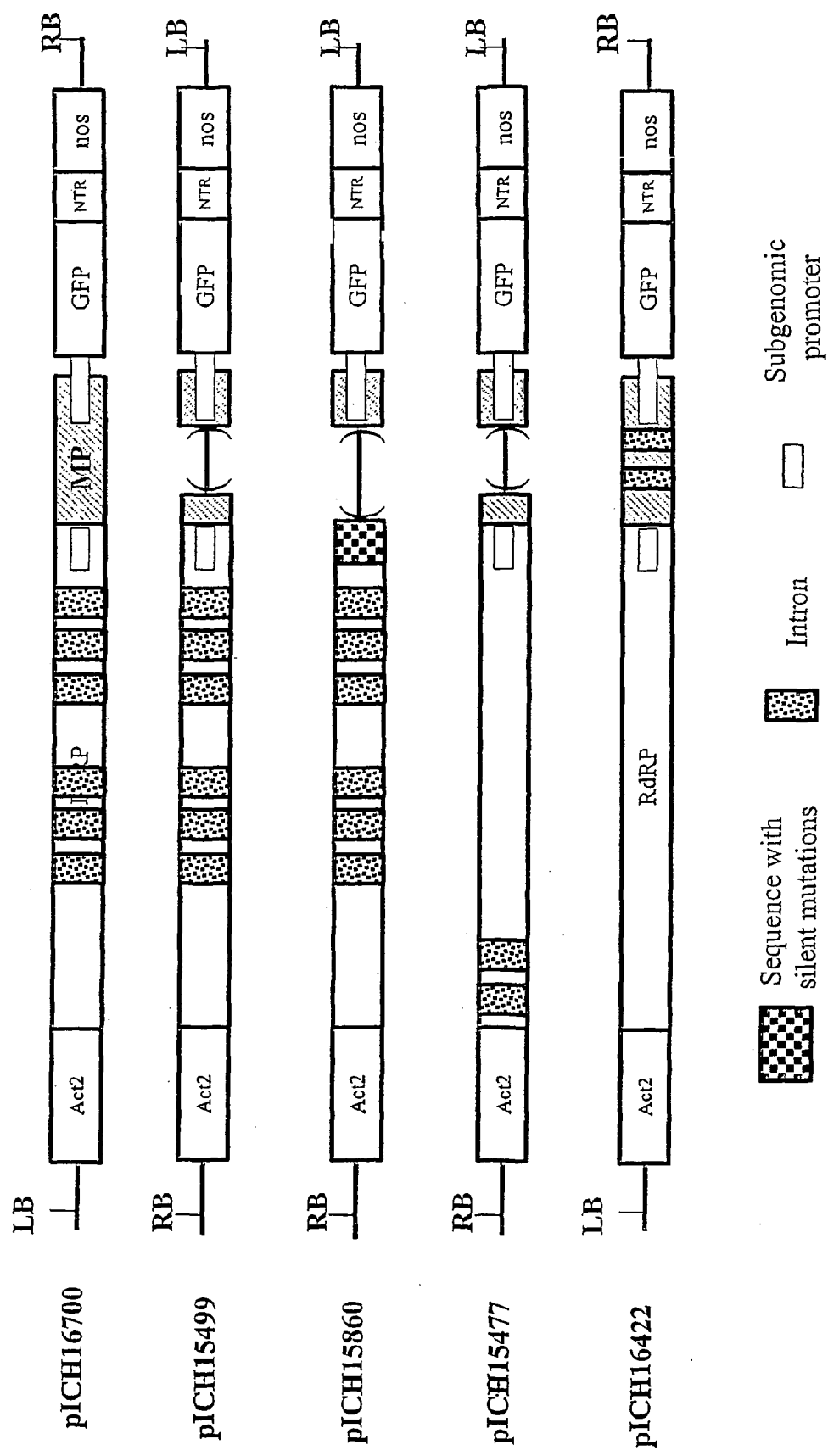

FIGS. 6 A and B are schematic representations of the T-DNA regions of vectors with and without function-conservative differences according to the invention.

FIG. 7 shows GFP expression after agroinfiltration of viral constructs in *Nicotiana benthamiana* and *Nicotiana tabacum* leaves. The vector (pICH) identification number for each infiltrated area is indicated.
7A—*Nicotiana benthamiana*, 8 days after agroinfiltration;
7B—*Nicotiana tabacum*, 8 days after agroinfiltration;
7C—*Nicothiana benthamiana* protoplasts isolated 5 days after agroinfiltration. Many light spots in the right picture indicate an extremely high frequency of replicon formation and GFP expression.

Figure 8:
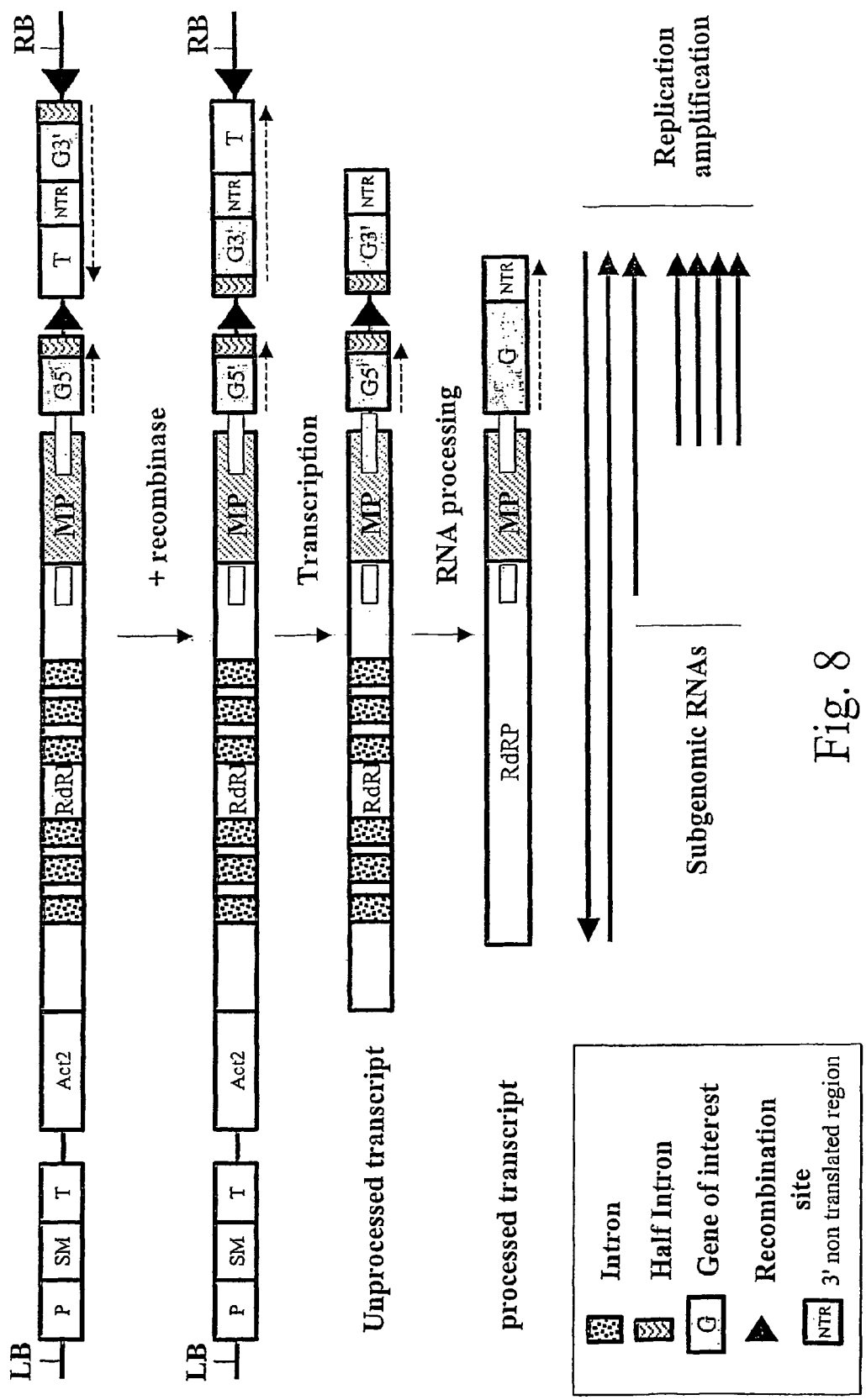

FIG. 8 is a schematic representation of an RNA virus-based replicon precursor designed according to the present invention, which gives zero expression level of the gene of interest (GFP, indicated by G) in the non-induced state.
P—transcription promoter; T—transcription termination region; SM—selectable marker gene; Ac2—promoter of *Arabidopsis* ACTIN2 gene; RdRP viral RNA-dependent RNA polymerase; MP—viral movement protein; NTR—viral 3' non-translated region.

Figure 9:
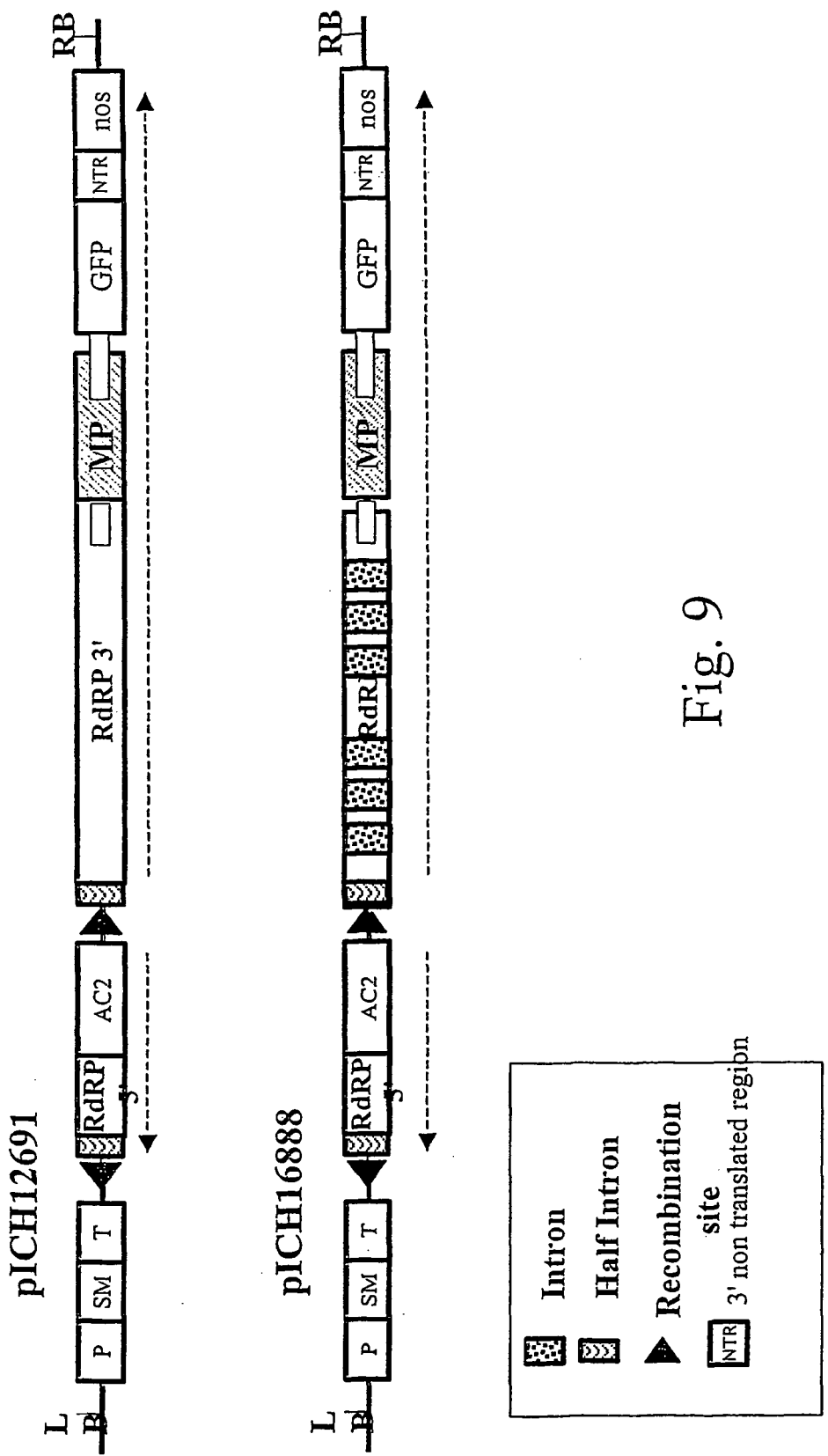

FIG. 9 depicts T-DNA regions of constructs pICH12691 and pICH16888.
P—transcription promoter; T—transcription termination region; SM—selectable marker gene; Ac2—promoter of *Arabidopsis* ACTIN2 gene; RdRP viral RNA-dependent RNA polymerase; MP—viral movement protein; NTR—viral 3' non-translated region.

Figure 10:
Figure 10:
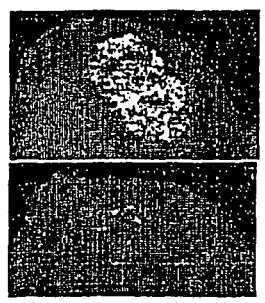

FIG. 10 shows leaves under UV light of different stably transformed *N. benthamiana* lines carrying the T-DNA regions of either pICH12691 or pICH16888. The leaves were agro-infiltrated with vectors (pICH10881 or pICH14313) providing integrase.

Figure 11:
Figure 11:
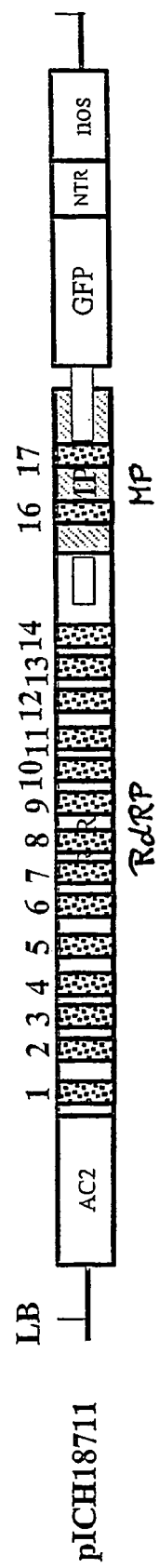

FIG. 11 shows leaves of *Beta vulgaris* one week after agro-infiltration with pICH18711 at day light (left) and UV (right) illumination. Light patches in the right photograph indicate GFP fluorescence. Introns (spotted boxes) in the construct shown at the bottom are numbered.

FIGS. 1 to 5 and 9 to 11 of PCT/EP04/012743 further illustrate the principle and examples of embodiments wherein sequences for replicon function of a DNA precursor of an RNA replicon exhibit at selected localities function-conservative differences from the sequence of the plant RNA virus, causing an increased frequency of replicon formation compared to an RNA replicon not exhibiting said differences.

DETAILED DESCRIPTION OF THE INVENTION

The present invention provides a process of highly efficient and biologically safe systemic expression of a sequence or protein of interest using an RNA virus-derived replicon (said RNA replicon (i)). This process overcomes limitations of existing RNA viral vector-based expression systems, such as size limitation for heterologous sequences to be expressed systemically and high instability of said vectors. Further, said process offers better biosafety characteristics and prevents the formation of wild type viruses due to recombination of viral components. The replicons (i) and (ii) of the invention can be designed such that such recombinations are avoided. The approach described herein allows for a rapid and highly efficient expression of a sequence of interest in a whole plant including systemic leaves.

To our knowledge, there are no efficient two-component systems relying on the use of (a) vectors that are deficient in systemic movement (lacking functional coat protein) and (b) transgenic plants providing the missing coat protein in trans. Such systems are not practically useful, probably because the levels of coat protein expressed even under a strong constitutive promoter is insufficient to provide for efficient systemic movement of the vector. In addition, creation of transgenic plants is time consuming and should be avoided in those applications where rapid expression of small amounts of protein or RNA of interest is required. Also, in case where a constitutive promoter provides for the expression of a sufficient amount of coat protein to support systemic movement, the biological safety of the system would be low, as the assembly of infectious viral particles would take place in systemic leaves.

Many different RNA viruses belonging to different taxonomic groups are suitable for constructing said RNA replicon (i) and said helper replicon (ii) of this invention, subject to the identification of the viral elements responsible for systemic movement and to the possibility to reconstitute the systemic movement functionality of the RNA replicon (i) by expressing one of such elements in trans from the helper replicon (ii) of the invention. A list of RNA viruses which can be used for the creation of said RNA replicon (i) and said helper replicon (ii) of this invention is presented below. Taxa names in quotes (and not in italic script) indicate that this taxon does not have an ICTV international approved name. Species (vernacular) names are given in regular script. Viruses with no formal assignment to genus or family are indicated:

RNA Viruses:
ssRNA Viruses: Family: Bromoviridae, Genus: Alfamovirus, Type species: alfalfa mosaic virus, Genus: Ilarvirus, Type species: tobacco streak virus, Genus: Bromovirus, Type species: brome mosaic virus, Genus: Cucumovirus, Type species: cucumber mosaic virus;

Family: Closteroviridae, Genus: Closterovirus, Type species: beet yellows virus, Genus: Crinivirus, Type species: Lettuce infectious yellows virus, Family: Comoviridae, Genus: Comovirus, Type species: cowpea mosaic virus, Genus: Fabavirus, Type species: broad bean wilt virus 1, Genus: Nepovirus, Type species: tobacco ringspot virus;

Family: Potyviridae, Genus: Potyvirus, Type species: potato virus Y, Genus: Rymovirus, Type species: ryegrass mosaic virus, Genus: Bymovirus, Type species: barley yellow mosaic virus;

Family: Sequiviridae, Genus: Sequivirus, Type species: parsnip yellow fleck virus, Genus: Waikavirus, Type species: rice tungro spherical virus; Family: Tombusviridae, Genus: Carmovirus, Type species: carnation mottle virus, Genus: Dianthovirus, Type species: carnation ringspot virus, Genus: Machlomovirus, Type species: maize chlorotic mottle virus, Genus: Necrovirus, Type species: tobacco necrosis virus, Genus: Tombusvirus, Type species: tomato bushy stunt virus, Unassigned Genera of ssRNA viruses, Genus: Capillovirus, Type species: apple stem grooving virus;

Genus: Carlavirus, Type species: carnation latent virus; Genus: Enamovirus, Type species: pea enation mosaic virus, Genus: Furovirus, Type species: soil-borne wheat mosaic virus, Genus: Hordeivirus, Type species: barley stripe mosaic virus, Genus: Idaeovirus, Type species: raspberry bushy dwarf virus;

Genus: Luteovirus, Type species: barley yellow dwarf virus; Genus: Marafivirus, Type species: maize rayado fino virus; Genus: Potexvirus, Type species: potato virus X; Genus: Sobemovirus, Type species: Southern bean mosaic virus, Genus: Tenuivirus, Type species: rice stripe virus, Genus: Tobamovirus, Type species: tobacco mosaic virus, Genus: Tobravirus, Type species: tobacco rattle virus, Genus: Trichovirus, Type species: apple chlorotic leaf spot virus; Genus: Tymovirus, Type species: turnip yellow mosaic virus; Genus: Umbravirus, Type species: carrot mottle virus;

In addition to TMV-based expression systems, viral vectors for expressing heterologous genes of interest were developed on the basis of several other plus sense ssRNA viruses, such as potato virus X (Mallory et al., 2002, *Nat. Biotechnol.*, 20, 622-625), alfalfa mosaic virus (Sanches-Navarro et al., 2001, *Arbh. Virol.*, 146, 923-939), and cowpea mosaic virus (Gopinas et al., 2000, 267, 159-173). The strategy described in this invention for TMV-based vectors can also be employed to the viral expression systems mentioned above.

The construction of different types of TMV-based viral vectors used in this invention (FIG. 1) is described in examples 1 to 5. Vector pICH8543 (example 1) has an origin of (viral particle) assembly but lacks a coat protein (CP) coding sequence. This vector and its intron-containing derivative pICH17272 (example 4) are capable of cell-to-cell movement and sequence of interest (GFP) expression in primary infected leaves and contain an origin of assembly, but are unable to move systemically due to the absence of a coat protein. Another pair of vectors, pICH10595 (example 2) and pICH17501 (example 5), encode, in addition to IMP, the CP instead of GFP, and are able to move systemically and to form infectious viral particles. Co-infiltration of the vectors pICH17272 and pICH17501 (FIG. 3) does not lead to GFP expression in systemic leaves. GFP is strongly expressed only in the primary inoculated leaf, but viral symptoms are clearly visible in systemic leaves. The explanation of this result is that an expression vector without CP (pICH17272) cannot compete with a helper virus (pICH17501) capable of moving systemically.

In order to address this problem, the helper viral vectors (helper replicon (ii)) pICH16601 and pICH16684 (FIG. 1, example 3) that are capable of expressing CP but lack the origin of assembly and are consequently unable to move systemically were generated. Co-infiltration of these helper viral vectors with RNA replicons (i) that express GFP but are unable to move systemically leads to the appearance of GFP in systemic leaves (FIG. 2). The total soluble protein from systemic leaves of plants infected with the two-vector system (FIG. 4, lanes 5-7) contained a high level of GFP that was comparable to that of primary inoculated leaves (FIG. 4, lane 2). This high expression level is not achieved when a systemically moving viral vector is used for GFP expression, as such a viral vector predominantly expresses CP (FIG. 4, lanes 12-14).

A minor amount of CP is also produced in systemic leaves by the two-component system of the invention (FIG. 4, lane 7). This can be explained by the presence of recombined viral vector capable of expressing CP and of moving systemically. However, the relative proportion of such recombinants is negligible and does not have any significant impact on the productivity (expression level) described above. In addition, the frequency of such recombinations can be further reduced and even eliminated completely, by reducing the length of overlapping stretches or the homology between the helper replicon (ii) and the RNA replicon (i) that expresses the sequence of interest.

The reduction or complete elimination of homologous functional regions being targets for homologous recombination can be achieved by several different approaches: deletions of said regions; changes of coding regions within the regions of homology by applying different codon usage; changing said regions by directed evolution (for review of approach see Tobin et al., 2000, *Curr. Opin. Struct Biol.*, 10, 421-427). In case of TMV-based viral vector systems, one can use different RNA-dependent RNA polymerases (RdRp) for the RNA replicon (i) that expresses said sequence of interest and the helper replicon (ii). Well characterised RdRps for this purpose are e.g. the RdRps of TVCV, TMV-U1, TMV-U5, or crTMV.

A homology within RdRp coding regions does, however, not cause a serious recombination problem, since recombination between regions upstream of the origin of viral particle assembly (in replicon (i)) does not result in wild-type virus or virus having the system movement capability of a wild-type virus. More problematic is a short region of homology located at the 3' end of the MP gene in front of GFP in case of the RNA replicon (i) (see FIG. 1, plasmids pICH8543; pICH17272) and the part of the MP coding sequence located in front of the CP ORF of the helper replicon (ii) (FIG. 1, pICH16601; pICH16684), since a recombination between these regions might lead to the formation of wild type virus-like replicons compromising the efficiency or safety of the system. Such short regions can be easily modified by various methods in order to remove the homology and any chance of undesired recombination events. In addition, certain functions of the replicons (i) and/or replicon (ii) like MP expression necessary for cell-to-cell movement, may be provided in trans by a transgenic host plant (Holt & Beachy, 1991, *Virology*, 181, 109-117). In such an embodiment, only those parts of the MP ORF overlapping with the RdRp of said helper replicon and the origin of assembly can be left in said RNA replicon (i). In general, there are many different strategies to reduce or completely remove the recombination frequency between said RNA replicon (i) and said helper replicon (ii), that can be easily performed by a person familiar with the art.

As was mentioned in the general description, in order to completely remove the homology region that can lead to the formation of autonomous viral vector capable of systemic movement, a subgenomic promoters can be used in order to drive CP expression from the helper replicon that is heterologous to the RNA virus from which said RNA replicon (i) is derived. More specifically, the subgenomic promoter used to drive CP expression from the helper replicon should be heterologous to the subgenomic promoter(s) used in the RNA replicon (i) to drive expression of MP and/or the sequence of interest. In the case of a TMV-based system, CP subgenomic promoters from different virus strains can be used in the helper replicon. Examples of such strains include TMV-U1, TMV-U5, crTMV, etc.

Interestingly, additional co-expression of MP in trans in infiltrated leaves increases the efficiency of systemic vector in our system. As it is shown in Example 7, transient expression of TVCV MP under control of a constitutive promoter significantly improves the efficiency of systemic movement of GFP-expressing replicon. This can be explained by production of larger quantities of CP by the helper replicon capable of cell-to-cell movement via said trans-complementation. Said additional CP might provide for packaging of larger number of RNA replicon (i) into viral particles capable of systemic movement.

Different methods may be used for providing cells of a plant with said RNA replicon (i) and/or said helper replicon (ii). Said vectors may be transformed into plant cells by a Ti-plasmid vector carried by *Agrobacterium* (U.S. Pat. Nos. 5,591,616; 4,940,838; 5,464,763) or particle or microprojectile bombardment (U.S. Pat. No. 05,100,792; EP 00444882B1; EP 00434616B1). Other plant transformation methods can also be used like microinjection (WO 09209696; WO 09400583A1; EP 175966B1), electroporation (EP00564595B1; EP00290395B1; WO 08706614A1) or PEG-mediated transformation of protoplasts etc. The choice of the method for vector delivery depends on the plant species to be transformed and the vector used. For example, microprojectile bombardment is generally preferred for vector delivery in monocot, while for dicots, *Agrobacterium*-mediated transformation gives better results in general.

In the examples described below, we used *Agrobacterium*-mediated delivery of vectors into *Nicotiana* cells. However, the vectors may be introduced into the plants in accordance with any of the standard techniques suitable for stable or transient transformation of the plant species of interest. Transformation techniques for dicotyledonous are well known in the art and include *Agrobacterium*-based techniques and techniques which do not require *Agrobacterium*. Non-Agrobacterium techniques involve the uptake of exogenous genetic material directly by protoplasts or cells. These techniques include PEG or electroporation mediated uptake, particle bombardment-mediated delivery and microinjection. Examples of these techniques are described in Paszkowski et al., *EMBO J.* 3, 2717-2722 (1984), Potrykus et al., *Mol. Gen. Genet.* 199, 169-177 (1985), Reich et al., *Biotechnology* 4:1001-1004 (1986), and Klein et al., *Nature* 327, 70-73 (1987). In each case, the transformed cells are regenerated to whole plants using standard techniques.

*Agrobacterium*-mediated transformation is a preferred technique for the transformation of dicotyledons because of its high transformation efficiency and its broad utility with many different plant species. The many crop species which may be routinely transformed by *Agrobacterium* include tobacco, tomato, sunflower, cotton, oilseed rape, potato, soybean, alfalfa and poplar (EP 0 317 511 (cotton), EP 0 249 432 (tomato), WO 87/07299 (Brassica), U.S. Pat. No. 4,795,855 (poplar)).

In the examples of this invention, we used agro-inoculation, a method of *Agrobacterium*-mediated delivery of T-DNA for transient expression of gene(s) of interest (Vaquero et al., 1999, *Proc. Natl. Acad. Sci. USA*, 96, 11128-

11133). Agro-inoculation is an extremely useful tool not only for small-to-middle scale recombinant protein production systems, but as one of the elements of a vector optimisation system allowing to obtain fast results with different variants of constructs.

This invention is not limited to TMV-based vectors described in examples 1-5, but can be extended to replicons based on other plant RNA viruses.

Sequences or genes of interest, their fragments (functional or non-functional) and their artificial derivatives that can be expressed in plants or plants cells using the present invention include, but are not limited to: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidcin, bacterial levansucrase, *E. coli* glgA protein, MAPK4 and orthologues, nitrogen assimilation/methabolism enzyme, glutamine synthase, plant osmotin, 2S albumin, thaumatin, site-specific recombinase/integrase (FLP, Cre, R recombinase, Int, SSVI Integrase R, Integrase phiC31, or an active fragment or variant thereof), oil modifying enzymes (like fatty acids desaturases, elongases etc), isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CryIC toxin, delta endotoxin, polypeptide toxin, protoxin etc.), insect specific toxin AaIT, cellulose degrading enzymes, E1 cellulase from *Acidothermus celluloticus*, lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, enzymes involved in the synthesis of polyhydroxyalkanoates (PHA), acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, *Umbellularia californica* C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, D6-desaturase, proteins having an enzymatic activity in fatty acids biosynthesis and modifications, e.g. the peroxysomal β-oxidation of fatty acids in plant cells, acyl-CoA oxidase, 3-ketoacyl-CoA thiolase, lipase, maize acetyl-CoA-carboxylase, etc.; 5-enolpyruvylshikimate-3-phosphate synthase (EPSP), phosphinothricin acetyl transferase (BAR, PAT), CP4 protein, ACC deaminase, protein having posttranslational cleavage site, DHPS gene conferring sulfonamide resistance, bacterial nitrilase, 2,4-D monooxygenase, acetolactate synthase or acetohydroxyacid synthase (ALS, AHAS), polygalacturonase, Taq polymerase, bacterial nitrilase, many other enzymes of bacterial or phage origin including restriction endonucleases, methylases, DNA and RNA ligases, DNA and RNA polymerases, reverse trascryptases, nucleases (Dnases and RNAses), phosphatases, transferases etc.

The present invention can be used for the purpose of molecular farming and purification of commercially valuable and pharmaceutically important proteins including industrial enzymes (cellulases, lipases, proteases, phytases etc.) and fibrous proteins (collagen, spider silk protein, etc.). Human or animal health protein may be expressed and purified using described in our invention approach. Examples of such proteins of interest include inter alia immune response proteins (monoclonal antibodies, single chain antibodies, T cell receptors etc.), antigens including those derived from pathogenic microorganisms, colony stimulating factors, relaxins, polypeptide hormones including somatotropin (HGH) and proinsulin, cytokines and their receptors, interferons, growth factors and coagulation factors, enzymatically active lysosomal enzyme, fibrinolytic polypeptides, blood clotting factors, trypsinogen, a1-antitrypsin (AAT), human serum albumin, glucocerebrosidases, native cholera toxin B as well as function-conservative proteins like fusions, mutant versions and synthetic derivatives of the above proteins.

Sequences for Replicon Function that Exhibit Function-Conservative Differences from the Sequence of the RNA Virus, Causing an Increased Frequency of Replicon Formation In this embodiment, said DNA precursor encoding said RNA replicon (i) contains sequences for replicon function of said RNA replicon (i), said sequences being derived from a sequence of said RNA virus, said sequences for replicon function exhibit at selected localities of said sequence of said RNA virus function-conservative differences from said sequence of said RNA virus, said differences causing an increased frequency of RNA (i) replicon formation compared to an RNA replicon not exhibiting said differences. Alternatively or additionally, said helper replicon may be derived from a plus-sense single stranded RNA virus and said DNA precursor encoding said helper replicon (ii) contains sequences for replicon function of said helper replicon (ii), said sequences being derived from a sequence of said RNA virus, said sequences for replicon function exhibit at selected localities of said sequence of said RNA virus function-conservative differences from said sequence of said RNA virus, said differences causing an increased frequency of helper replicon formation compared to a helper replicon not exhibiting said differences.

Said function-conservative differences are preferably present in the replicase ORFs of said DNA precursors. In cases where said RNA replicon (i) and said helper replicon (ii) are based on the same RNA virus, the replicase ORFs including said function-conservative differences in the RNA replicon (i) and the helper replicon (ii) may be identical. Further, function-conservative differences may be present in an MP ORF, notably of the DNA precursor of said RNA replicon (i).

Said function-conservative differences are causal for said increased frequency of RNA replicon (i) and/or helper replicon (ii) formation in plant cells. The causal connection between the increased frequency of replicon formation and said differences can be tested experimentally by comparing the frequency of replicon formation between sequences for replicon function having said differences and sequences for replicon function not having said differences. Such an experimental comparison can be made e.g. by counting protoplasts expressing said sequence of interest as described in the examples. Preferably, a sequence of interest coding for an easily detectable reporter protein like green fluorescent protein is used for this purpose. As further described below, it is also preferred to perform the experimental comparison with RNA replicons not capable of cell-to-cell spreading.

Said function-conservative differences are introduced into said sequences for replicon function at selected localities of said sequence of said RNA virus. Said selected localities are localities in sequences for replicon function of said RNA virus that are responsible for a low probability of an RNA replicon transcribed in the nucleus to appear in the cytosol as a functional replicon. Preferably, such selected localities have a high A/T(U)-content, i.e. a high A-content and/or a high T-content (a high U-content on RNA level), or have cryptic splicing sites, i.e. sequence portions that can be recognized by the nuclear splicing machinery as splicing sites. Said selected localities may be identified in an RNA virus on which an RNA replicon is based by analyzing the RNA profile of the RNA virus as exemplified below. Further, selected localities may be identified experimentally by analyzing the RNA formed in a plant cell after transformation with a heterologous DNA encoding an RNA replicon that does not exhibit said (function-conservative) differences according to the invention. This experimental analysis may be done by RT-PCR, preferably together with sequencing of the RT-PCR products. In the RT-PCR test, the replicase is preferably rendered dysfunctional e.g. by a frame-shift mutation in order to prevent RNA replicons reaching the cytoplasm from amplifying; such amplification may lead to contamination of RNA transcripts with wild type virus or to an overrepresentation of amplified RNA replicons in the cytoplasm. In this way, undesired splicing products that indicate splicing events destroying the RNA replicon may be identified. Further, the exact sites of undesired splicing may be identified and then remedied by introducing said function-conservative differences at said selected localities.

Thus, the invention also provides a process of expressing a sequence of interest in a plant, plant part, or plant cell culture, wherein (A) a plant, plant part, or plant cell culture is provided with a DNA precursor lacking said function-conservative differences, (B) testing RNA derived from said DNA precursor for undesired splicing products in said sequences for replicon function (e.g. by RT-PCR), (C) identifying (e.g. in the sequence of a product of said RT-PCR), a selected locality as a locality of an undesired splicing event, (D) introducing a function-conservative difference (e.g. an intron) according to the invention into or near said selected locality identified in step (C) into a DNA precursor of step (A) for producing said DNA precursor encoding said replicon (i) or (ii) of the invention, and expressing a sequence of interest in a plant, plant part, or plant cell culture according to the invention, e.g. from a plant transiently transformed with said heterologous DNA of the invention.

Said function-conservative differences cause an increased frequency of replicon formation by suppressing the deleterious effect of said selected localities on said frequency of RNA replicon formation. Said function-conservative differences may comprise a reduction of a high A/U-content in said RNA replicon by reducing a high A/T content in said sequences for replicon function of said sequence encoding said RNA replicon. Said high A/U content may be reduced by at least partial deletion or at least partial replacement by G/C bases (e.g. using the degeneracy of the genetic code), provided said differences are function-conservative. Further, cryptic splicing sites flanking A/U-rich regions of said sequences derived from a plant RNA virus may be removed. Such function-conserved differences may be introduced at one or at, preferably, several selected localities.

Preferred function-conservative differences comprise the insertion of one or more introns, most preferably nuclear introns, or one or more sequences capable of forming nuclear introns near or within A/U-rich localities of said sequences being derived from sequences of said plant RNA virus. It has surprisingly been found that the introduction of introns at or near A/U-rich localities results in an increased frequency of RNA replicon formation. Several introns may be introduced and examples are given herein for various numbers of introduced introns. The effects of more than one intron are cumulative. Further, intron insertion may be combined with other function-conservative differences at other selected localities.

FIG. 8 shows an example for the introduction of sequences capable of forming a nuclear intron, albeit in the sequence of interest to be expressed. In the example of FIG. 8, the intron is formed from two intron halves upon recombinase-catalyzed flipping of a part of said heterologous DNA. This principle may also be applied to sequences for replicon function of said RNA replicon. In an embodiment wherein two different RNA replicons are formed in the same cell, recombination between said two different replicons may result in the formation of an intron from two intron halves present on different replicons. Further, an RNA replicon may be formed by recombination between two precursors, neither of which is a replicon. Also in this case, an intron may be assembled from two intron halves derived from different precursor molecules.

The plant or the plant part (e.g. leaves) are preferably transiently transformed with said DNA precursors of the invention for transient expression of said sequence of interest. The term "transient transformation" means the introduction of said DNA precursors without selection of transformed cells for stable incorporation of said heterologous DNA into a plant chromosome. Transient transformation usually provides for transient expression of the sequence(s) encoded by the DNA precursor(s). Transient transformation can be achieved by any of the transformation methods given above. Agroinfiltration is preferred, e.g. by dipping the plant upside down in the *Agrobacterium* suspension, application of vacuum, and fast release of the vacuum.

The DNA precursors encoding an RNA replicon is preferably operably linked to a transcriptional promoter, preferably a constitutive transcriptional promoter. In another embodiment, said plant belongs to the genus *Nicotiana* and said sequences for replicon function are derived from a tobamovirus, preferably from tobacco mosaic virus. In a particularly preferred embodiment, tobacco plants including the stem and all leaves are transiently transformed by agroinfiltration. The latter embodiment can be used for large-scale applications of the process of the invention. In large-scale applications, said process is concomitantly applied to many plants (at least 5, preferably at least 10, more preferably at least 100 plants).

It is known that plant RNA viruses (an exception are viroids—small non-coding RNAs amplifying in plant cell nuclei—for a review see Diener, T. O., 1999, *Arch. Virol. Suppl.*, 15, 203-220; Flores, R., 2001, *CR Acad. Sci. III*, 324, 943-952) never occur in the plant nucleus, but in the cytoplasm. Therefore, the sequences of RNA viruses are not adapted to withstand nuclear RNA processing events due to the presence of motifs that might be involved in complex series of processing steps including transport of processed RNA in cytoplasm, in which pre-mRNAs, rRNA and tRNA precursors are involved. The processing events, such as 5' end capping, splicing, 3' end generation, polyadenylation, degradation, base and sugar modification as well as editing (in plastids and mitochondria) are intensively studied. However, many elements of such events still remain unclear. The most dramatic changes to pre-mRNA in the nucleus happen during pre-mRNA splicing, the process by which intervening RNA sequences (introns) are removed from the initial transcript and exons are concomitantly ligated. Splicing is mediated by the splicesome, a complex structure comprising uridilate-rich small nuclear ribonucleoprotein particles. The splicesome carries out the splicing reaction in two consecutive steps: the first one—cleavage at the 5' splice site of upstream exon/ intron junction leading to lariat formation, and second step— cleavage at the 3' splice site of intron/downstream exon junction followed by upstream and downstream exons ligation (for review see: Kramer, A., 1996, Annu. Rew. Biochem., 65, 367-409; Simpson, G G. & Filipowicz, W. 1996, Plant. Mol. Biol., 32, 1-41). The 5' and 3' splice site dinucleotides (5'/GU; AG/3') flanking the intron sequences are highly conserved in higher plants and single G replacement might abandon the splicing activity at the site concerned. It is surprising that despite of a high conservation of splice sites between plants and animals, heterologous introns in plants are usually not spliced or spliced incorrectly (van Santen, V L. et al., 1987, Gene, 56, 253-265; Wiebauer, K., Herrero, J. J., Filipowicz, W. 1988, Mol. Cel. Biol., 8, 2042-2051). Considering that plant viral RNAs were not under evolutionary pressure to resist nuclear RNA processing machinery, these RNAs are very likely to become subject of such processing, including splicing, once they are placed into the nuclear environment. We address these problems by subjecting the expression vector to function-conservative modifications that significantly increase the frequency of functional RNA replicon formation, when the expression vector is introduced as a DNA precursor into plants or plant cells to provide for transient expression. We believe that such modifications of virus-derived sequences are the most profound solution for increasing the efficiency of RNA virus-based replicons. In this invention we predominantly focus on modifications (said function-conservative differences) within the plant RNA virus derived sequences, as they are crucial for increasing the efficiency of RNA replicon formation.

By introducing said function-conservative differences (e.g. introns), we have unexpectedly found an improvement of orders of magnitude. An analysis of the sequence derived from the RNA virus of expression vector pICH8543 (Reference Example 1, FIG. 6A) using the Netgenell server program (Hebsqaard et al., 1991, J. Mol. Biol., 220,49-65) for the presence of cryptic introns and RNA splicing sites showed the presence of intron-like regions that might be spliced by the nuclear RNA processing machinery (see circled regions in FIG. 2 of PCT/EP04/012743). There are many other programs that can be used to identify potentially problematic regions (said selected localities) within plant viral RNA sequences, such as exon/intron prediction program (Burge & Karlin, 1997, J. Mol. Biol., 268, 78-94) or splicing signal prediction program SpliceView of ITB, the Italian Institute for Biomedical Technologies, for a variety of organisms.

Considering that all existing programs are not ideal and are subject to mistakes, the potential problematic regions can also be determined experimentally. This can be done by analyzing the transcripts derived from a DNA vector under test in a nuclear environment with the help of such a routine technique as RT-PCR (Frohman, M A., 1989, Methods Enzymol., 218, 340-356) or its more advanced version suitable for precise quantification of the concentration of different transcripts called real-time PCR (Gibson et al., 1996, Genome Res., 6, 995-1001), preferably followed by sequencing of the PCR-amplified products. The function-conservative differences of the invention change dramatically the RNA profile, for example by replacing intron-like sequences with exon-like ones, e.g. by introducing silent mutations with replacement of A/U-rich regions (intron-like) with G/C-rich regions (exon-like) (see FIG. 3 of PCT/EP04/012743, circled regions). Plant introns, unlike exons, are usually A/T(U) rich (Lorkovic, Z J. et al., 2000, Trends Plant Sci., 5, 160-167; Brown, J W. & Simpson, C G. 1998, Annu. Rev. Plant Physiol. Plant Mol. Biol., 49, 77-95; Csank, C. et al., 1990, Nucl. Acid Res., 18, 5133-5141; Goodall & Filipowicz, 1989, Cell, 58, 473-483), but there are exceptions, for example when in monocotyledonous plants G/C rich introns were found (Goodall & Filipowicz, 1989, Cell, 58, 473-483; Goodall & Filipowicz, 1991, EMBO J., 10, 2635-2644). For practicing this invention, selected localities of high A/T(U) content include not only sequence stretches of at least 20 nucleotides in length with at least 55%, preferably at least 65%, most preferably 80% or a higher of A/T(U) content, but also shorter stretches ("islands") of 6-19 nucleotides in a row of purely A/T(U)-containing sequences. Herein, localities of high A/U content include sequences which are more A- than U-rich, sequences which are A-rich, sequences which are more U- than A-rich, and sequences which are U-rich. Additionally, any transcribed sequence of interest can be tested for post-transcriptional modifications that cause a change in nucleic acids sequences (e.g. RNA splicing) by RT-PCR (Frohman, M A. 1989, Methods Enzymol., 218, 340-356). It is a trivial task for those familiar with the art to use RT-PCR for detecting the regions within RNA that are subject to post-transcriptional modifications like deletions of sequences from the original RNA transcript. In Reference Example 2 we demonstrate that the modification of A/U rich region increases the number of GFP expressing cells at least 10-fold. This is clearly demonstrated in FIG. 7 by comparing the areas agroinfiltrated with pICH15466 (modified vector, FIG. 6A) and pICH14833 (control vector, FIG. 6A). Removing the movement protein (MP) allows for an accurate count of primary cells possessing functional RNA replicons, as cell-to-cell movement from the site of primary infection to neighbouring cells does not take place. In Reference Example 3, the modification of another U-rich intron-like region containing many cryptic splice sites (FIG. 2B of PCT/EP04/012743) and covering the subgenomic promoter of the movement protein (MP) was performed (FIG. 4 of PCT/EP04/012743, circled). This modification gave a dramatic effect on the increase of the frequency of replicon formation from viral vector pICH1590. As it was established in protoplast counting experiments (Reference Example 3), the increase was approximately 100-fold in comparison with the unmodified vector pICH14833 for both tested Nicotiana species—N. benthamiana and N. tobacco (see the corresponding infiltrated areas in FIG. 7, A, B). In general, by using the approaches described here, the frequency of RNA replicon formation can be increased approx. 300-fold, i.e. increasing the proportion of cells with functional replicons from about 0.2% (control vector) to more than 50% (modified vector). We believe this is not the limit and reaching a frequency of 100% is very realistic.

Figure 7A:
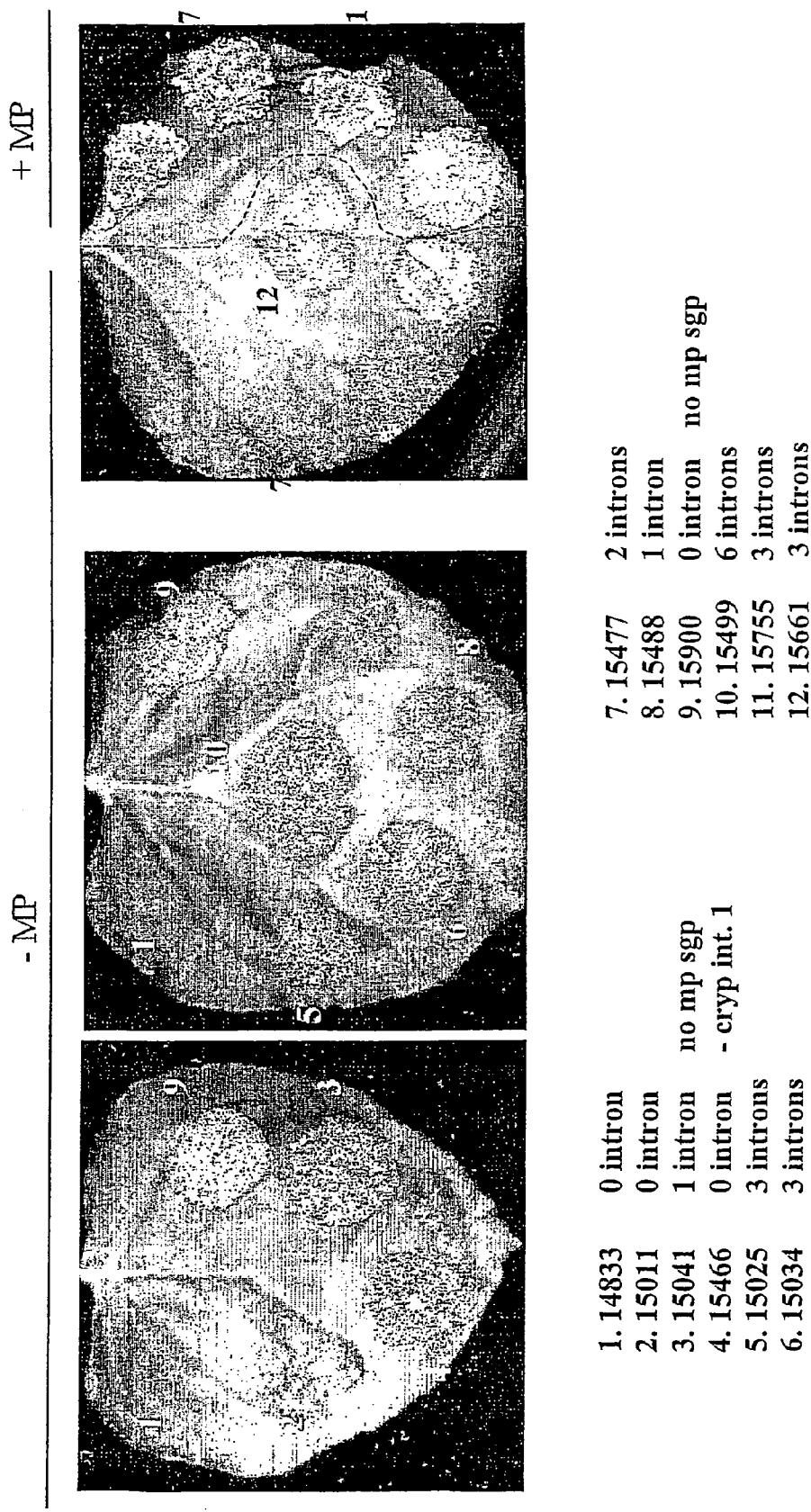
Figure 7B:
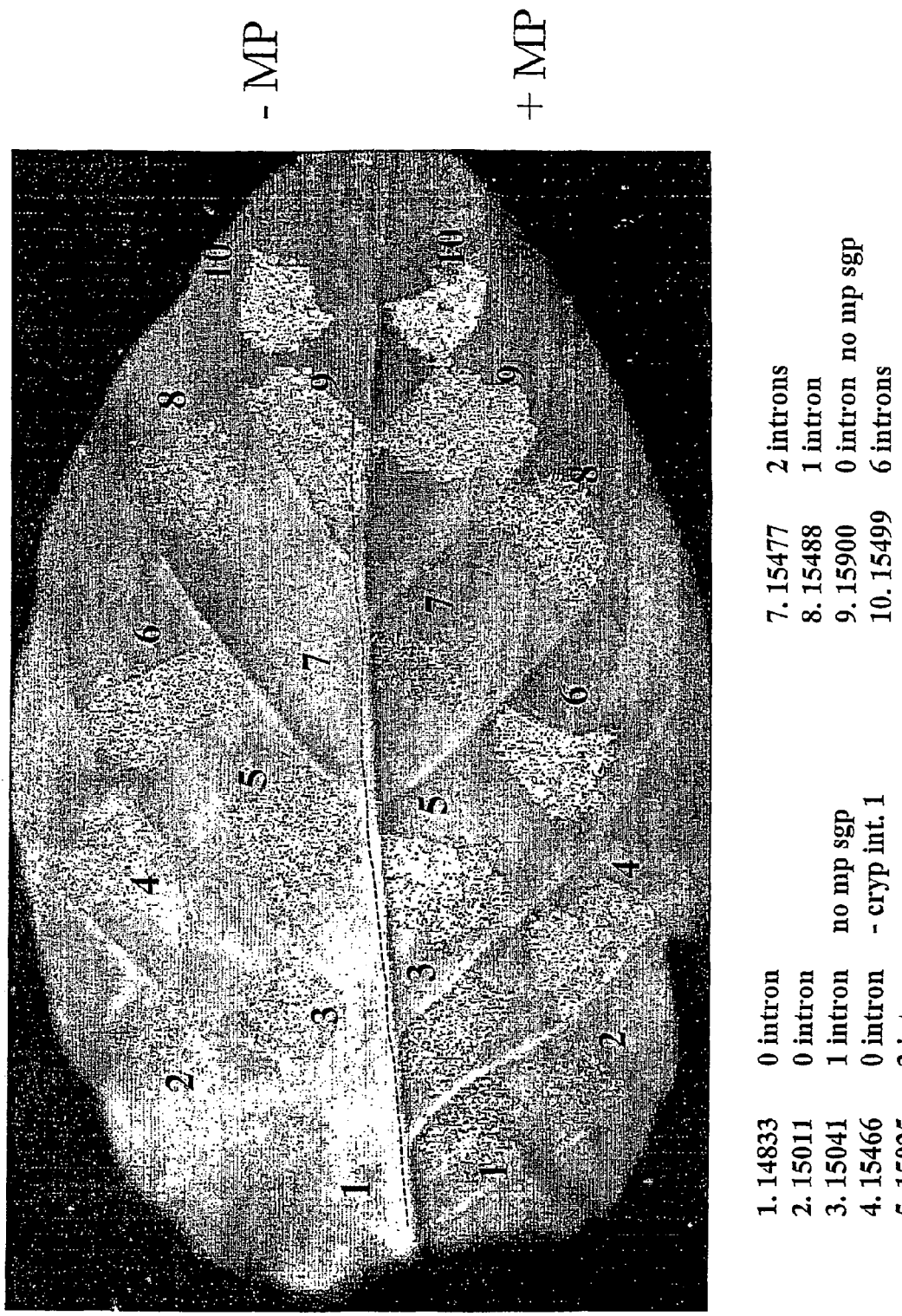
Figure 7C:
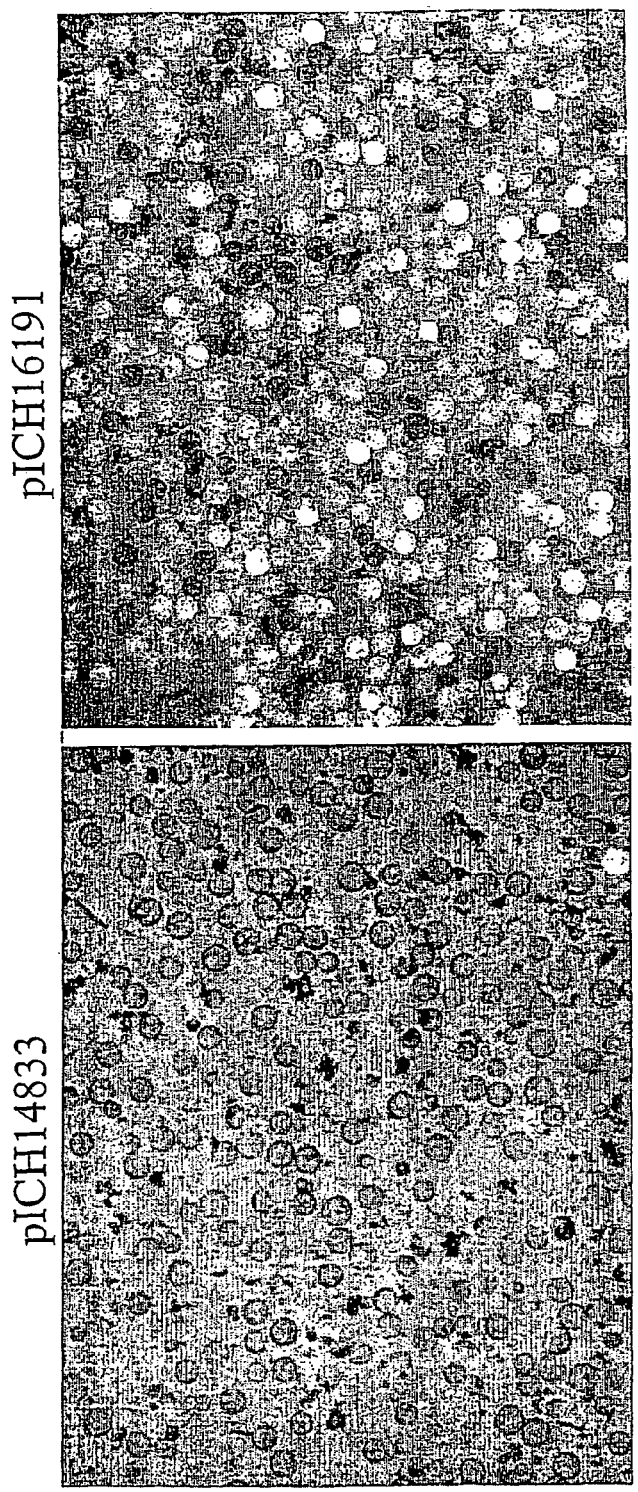
Figure 7C:
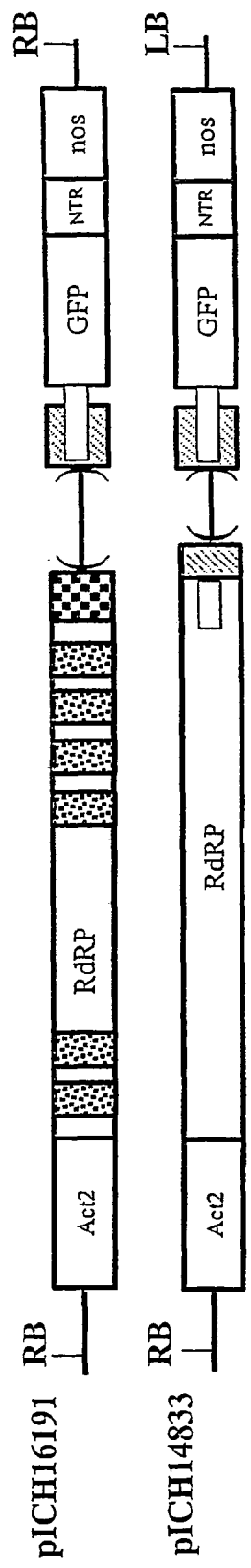

Such a high efficiency of replicon formation opens the door for expressing two or more different genes from two different RNA replicons (like sid RNA replicon (i) and said helper replicon (ii)) within the same plant cell, e.g. co-expressing different genes by using two or more plant RNA virus based vectors (Example 4 and 5). The achievement of synchronized release of two or more replicons concomitantly in the same cell is crucial for such co-expression, as the principle "first come, first served" is especially true for viral vectors. Systemic or cell-to-cell movement does not help, as different viral vectors do normally not overlap in their areas of spread or such overlap is insignificant. Simple calculations demonstrate the importance of the technology for achieving co-expression of two sequences of interest in the same plant cell from two replicons. In the case of a non-optimised viral vector with a frequency of functional replicon formation of only 0.2% of all cells, the proportion of cells co-expressing two genes from two different RNA replicons will be 0.2×0.2=0.04%, while for the construct with increased frequency of functional RNA replicon formation (50% or ½ of all cells), said proportion of cells will be 0.5×0.5=0.25 or 25%, e.g. about 625-fold higher. With some of the best performing vectors (e.g. pICH16191, FIG. 7C) the proportion of cells having the functional replicon reaches ca. 90% (FIG. 7C, top right). This means that using such a vector for expressing two different sequences of interest from two independent replicons, co-expression can take place in about 80% of all cells. It appears very likely that the technology can be further improved and that 100% co-expression can be reached.

It is worth to note that function-conservative differences in heterologous sequences of interest to be expressed from said RNA replicon might also be used to increase the frequency of RNA replicon formation, notably in combination with differences in sequences for replicon function. For example, modifications within said sequences of interest can be introduced that are necessary for formation and/or processing of said replicon.

In an important embodiment of this invention, the frequency of replicon formation is improved by inserting nuclear introns in said sequences for replicon function (Reference Example 4). The incorporation of introns into the coding region of viral RNA-dependent RNA polymerase (RdRP) (Reference Examples 4 and 8) results in a significant (at least 50-fold) increase in the frequency of replicon formation from (FIG. 7A,B) vectors carrying function-conservative differences as defined herein (pICH15034, pICH15025, pICH15499 in FIG. 6 A,B). The RNA profile for a vector containing 6 inserted introns from *Arabidopsis* is shown in FIG. 5 of PCT/EP04/012743. In another example (Reference Example 7), insertion of introns in MP sequences increases the frequency of replicon formation at least 100 times.

Many nuclear introns can be used to practice this invention. Examples of such introns include introns from rice tpi Act1, and salT genes (Rethmeier et al., 1997, *Plant J.*, 12, 895-899; Xu et al., 1994, *Plant Physiol.*, 100, 459-467; McElroy et al., 1990, *Plant Cell*, 2, 163-171); from the maize Adh1, GapA1, actin and Bz1 genes (Callis et al., 1987, *Genes Dev.*, 1, 1183-11200; Donath et al., 1995, *Plant Mol. Biol*, 28, 667-676; Maas et al., 1991, *Plant Mol. Biol.*, 16, 199-207; Sinibaldi & Mettler, 1992, in W E Cohn, K Moldave, eds, *Progress in Nucleic Acids Research and Molecular Biology*, vol 42, Academic Press, New York, pp 229-257), from petunia rubisco gene SSU301 (Dean et al., 1989, *Plant Cell*, 1, 201-208), *Arabidopsis* A1 EF1α, UBQ10, UBQ3, PAT1 genes (Curie et al., 1993, *Mol. Gen. Genet.* 228, 428-436; Norris et al., 1993, *Plant Mol. Biol.*, 21, 895-906; Rose & Last, 1997, *Plant J.*, 11, 455-464) and many others. Synthetic introns can also be used for this invention. The smallest usable introns or their parts may be limited to splice donor and acceptor sites which usually flank the internal intron sequences. Preferably, the introns should have a size of at least 50 nt., more preferably a size of 100 to 200 nt., but actually there are no limitations regarding the size of the introns. However, the size of the construct should be kept suitable for manipulations. The origin of the intron, its structure and size may be selected individually depending on the nature of the vector. Transient expression experiments may be used for testing the efficiency of a chosen intron or the corresponding intron parts.

The modifications described above have a cumulative effect, e.g. if intron insertion(s) are combined with a modification of the MP subgenomic promoter, the increase in frequency of replicon formation can be approx. 300-fold (Reference Example 5). The preferred regions for intron insertions in order to have an increase in the frequency of RNA replicon formation are called selected localities herein. Such localities may contain "intron-like" structures. This is confirmed by the insertion of introns in MP, actually in close proximity to such a problematic region as the MP subgenomic promoter (Reference Example 7). A 100-fold increase in frequency of replicon formation was observed. Insertion of introns into "exon-like" regions does not have such a pronounced effect as insertion in said intron-like regions (Reference Example 6).

The content of patent application European patent application No. 04001460.7, filed on Jan. 23, 2004, the priority of which is claimed by the present patent application and the content of International patent application PCT/EP03/012743 are incorporated herein by reference.

EXAMPLES

Information on the genetics of tobamoviruses like TMV and crucifer-infecting tobamovirus can be found in WO02/029068.

Example 1

Construction of a GFP-Expressing TMV-Based RNA Vector

A cr-TMV-based viral vector containing GFP, pICH8543 (FIG. 1), has been described in international patent application PCT/EP03/12530 (see also below). This clone contains the *Arabidopsis* Actin2 promoter, the TVCV RNA-dependent RNA polymerase, a chimaeric sequence (TVCV/cr-TMV) for the movement protein, the GFP coding sequence, the 3' untranslated region of cr-TMV and finally the Nos terminator, cloned in a binary vector. This clone lacks a coat protein coding sequence. pICH8543 was transformed into *Agrobacterium* strain GV3101 and infiltrated into one leaf of a *Nicotiana benthamiana* plant using a needle-less syringe. Four days after infiltration, GFP fluorescence foci could be seen in the infiltrated area. Fluorescence lasted for several weeks in the infiltrated leaf but did not move to upper uninoculated leaves.

Construction of Vector pICH8543

A replicon containing a green fluorescent protein (GFP) gene was made in several cloning steps. The resulting construct, pICH8543, contains in sequential order: a 787 bp fragment from the *Arabidopsis* actin 2 promoter (ACT2, ref An et al, 1996, GenBank accession AB026654, bp 57962 to 58748), the 5' end of TVCV (GenBank accession BRU03387, bp 1 to 5455), a fragment of cr-TMV (GenBank accession Z29370, bp 5457 to 5677, with thymine 5606 changed to cytosine to remove the start codon of the coat protein, CP), sequences "taa tcg ata act cga g", a synthetic GFP (sGFP) gene, cr-TMV 3' nontranslated region (3' NTR; GenBank accession Z29370, bp 6078 to 6312), and finally the nopaline synthase (Nos) terminator. The entire fragment was cloned between the T-DNA left (LB) and right (RB) borders of pICBV10, a Carb$^R$ pBIN19-derived binary vector.

Example 2

Construction of a CP-Expressing TMV-Based RNA Vector

Cloned cDNAs of the crucifer-infecting tobamovirus (cr-TMV; Dorokhov et al., 1994, *FEBS Lett.* 350, 5-8) and of the turnip vein-clearing virus (TVCV; Lartey et al., 1994, *Arch. Virol.* 138, 287-298) were obtained from Prof. Atabekov from Moscow University, Russia. A viral vector expressing TVCV CP was made by subcloning an EcoRI-ApaI fragment (containing part of MP, the complete CP coding sequence, and the 3' non translated region of TVCV) from the TVCV cDNA into pICH8543. The resulting clone, pICH10595 (FIG. 1), contains the complete TVCV cDNA cloned between the *Arabidopsis* Actin2 promoter and the Nos terminator, in a binary vector. The pICH10595 was transformed in *Agrobacterium* strain GV3101 and infiltrated into a *Nicotiana benthamiana* leaf. Three weeks later, the upper non-infiltrated leaves had a wrinkled yellow appearance indicating viral infection. Polyacrylamide gel electrophoresis (PAGE) with coomassie staining and Western blot analysis revealed that the systemic leaves expressed large amounts of coat protein, indicating that pICH10595 is functional.

To test whether CP produced by pICH10595 could package in trans the RNA replicon of pICH8543, both clones were co-infiltrated into a *Nicotiana benthamiana* leaf. Five days after infiltration, GFP could be detected in the inoculated leaf area. However, no GFP could be detected in upper leaves, even three weeks after infiltration. At this time, the inoculated plant had typical symptoms of a plant inoculated with wild-type virus: it was shorter than a control uninoculated plant, and upper leaves were wrinkled and yellowish. PAGE and coomassie staining of the gel showed that CP was expressed in the systemic leaf, but no GFP protein could be detected. Western blot analysis also failed to detect GFP in the systemic leaves, although GFP was detected in the inoculated leaf. In conclusion, a wildtype virus is unable to move a viral amplicon expressing a gene of interest (such as GFP) in trans.

Example 3

Construction of a CP-Expressing Clone Lacking an Origin of Assembly

In the previous example, only the wild type virus is detected in the upper uninoculated leaves when the lower leaves are first infiltrated with a mixture of CP and GFP-expressing clones. The CP clone is so efficient to replicate and move that the GFP-expressing clone cannot compete effectively and move systemically. To prevent the CP-expressing clone to move systemically, we removed the area that putatively contains the origin of assembly (OAS) of the virus (the CP-expressing clone), which corresponds to part of the MP located upstream of the CP subgenomic promoter. The resulting clone, pICH16601 (FIG. 1) is similar to pICH10595 but lacks base pairs 4966-5454 (coordinates relative to GenBank accession BRU03387). pICH16601 was transformed in *Agrobacterium* strain GV3101 and was coinfiltrated with pICH8543 into a *Nicotiana benthamiana* leaf. Twelve days later, GFP fluorescence appeared in the veins of the upper non-infiltrated leaves. Then, on the following days, GFP fluorescence grew out of the veins into leaf tissue and covered part of the leaf area. PAGE and coomassie staining as well as Western blot analysis showed that GFP protein was made in the systemic leaves. Therefore, removing the OAS from the CP-expressing clone allows a clone of interest to move systemically by providing CP in trans.

Example 4

Addition of Introns to the Construct Containing the Gene of Interest Improves its Systemic Movement To improve the efficiency of coexpression of the CP-expressing clone and of the clone of interest in the infiltrated area, introns were inserted in the RdRp and the MP of the construct containing the heterologous sequence of interest. pICH8543 was modified by addition of ten *Arabidopsis* introns in the RdRp (introns 1 to 10, sequence in the annex) at positions 1844, 2228, 2588, 2944, 3143, 3381, 3672, 3850, 4299, 4497 (coordinates relative to GenBank accession BRU03387) and of two introns in the MP (introns 11-12) at positions 5287 and 5444. The resulting clone, pICH17272 (FIG. 1) was coinfiltrated in an *Nicotiana benthamiana* leaf with pICH16601. GFP appeared in the systemic leaves starting 7 days after infiltration, faster than when a clone without intron was used.

Example 5

Addition of Introns to the CP-Expressing Construct Improves Systemic Movement of the Construct Containing the Sequence of Interest To improve expression of CP in a larger number of cells in the infiltrated area, introns 1 to 9 (described above) were added to pICH16601, at the same positions as described for the construction of pICH17272. In addition, the MP subgenomic promoter area was replaced by less T-rich and more GC-rich sequence. As a result, the sequence between bp 4585 to 5460 (coordinates relative to GenBank accession BRU03387) were replaced by Seq 1 given in the annex, resulting in construct pICH16684 (FIG. 1). pICH16684 was coinfiltrated with pICH17272 in an *N. benthamiana* leaf. Seven days after infiltration, GFP appeared in systemic leaves (FIG. 2). More tissue expressing GFP was obtained than when clones without introns were used.

An additional CP-expressing construct was made by the addition of 6 introns (introns 1 to 3 and 7 to 9, as described for construction of pICH17272) to pICH10595. This construct, pICH17501 (FIG. 1), contains a complete MP and therefore contains the OAS. This construct was coinfiltrated with pICH17272. GFP was expressed in the infiltrated leaf area, but never move to upper systemic leaves (FIG. 3). Only CP-expressing amplicons were found in the systemic leaf. This shows that the presence of introns is not sufficient for systemic movement, and that removing the OAS from the CP-expressing clone is essential.

Example 6

The Gene of Interest is Expressed at High Level in Systemic Leaf

To compare the approach described herein with systemic movement obtained using traditional vectors which express CP from the same molecule as the gene of interest, we made a control construct, pICH17344, that expresses both GFP and CP (FIG. 1). This construct is similar to pICH17272 but the 3' end of the 3'NTR (corresponding to bp 6274 to 6312 in GenBank accession Z29370) was replaced by the 1005 3' terminal sequence from tobacco mild green mosaic virus (TMGMV) U5 variant (bp 5498 to 6502). pICH17344 was transformed in *Agrobacterium* GV3101 and infiltrated into a *Nicotiana benthamiana* leaf. Seven days after inoculation, GFP fluorescence was detected in systemic leaves. Analysis by PAGE and coommassie staining showed that more CP was made than GFP in the systemic leaves of plants inoculated with pICH17344 (FIG. 4). In contrast, no or little CP was present in the systemic leaves of plants inoculated with a mixture of pICH16684 and pICH17272 (FIG. 4). Therefore, in the present invention, most expressed protein in systemic leaves corresponds to the gene of interest instead of CP.

Some CP is made in systemic leaves of plants inoculated with a mixture of pICH16684 and pICH17272, albeit less than with pICH17344. This most likely occurs as a result of recombination between pICH16684 and pICH17272, producing a wild type CP-expressing virus. Reducing homology between both clones by making a CP-expressing clone based on a related but different virus (for example TMV strain U1) can reduce or eliminate such recombination events.

Example 7

Transient Expression of MP in Trans in Infiltrated Leaves

Clones with a mutated OAS, pICH16601 and pICH16684 (FIG. 1), cannot move from cell-to-cell due to a deletion of a part of the MP (unless they are coexpressed with a second amplicon expressing MP). Therefore, only a limited number of cells express CP in infiltrated leaf areas. We reasoned that expression of MP in trans in all cells of the infiltrated area would result in more cells expressing CP, and therefore in more cells coexpressing the GFP and CP constructs, and finally, in more efficient systemic movement. A construct containing the TVCV MP gene under control of the 35S promoter was made. This construct, pICH10745 (FIG. 5, A), was coinfiltrated with pICH17272 and pICH16684 (FIG. 5B). Systemic movement of GFP-expressing amplicons was significantly more efficient with such transient complementation of MP in trans (FIG. 5B) than when the MP construct was not used (see FIG. 2).

REFERENCE EXAMPLES

The following Reference Examples correspond to examples 1 to 11 of PCT/EP04/012743.

Reference Example 1

Construction of a TMV-Based RNA Vector

Cloned cDNAs of the crucifer-infecting tobamovirus (cr-TMV; Dorokhov et al., 1994, *FEBS Lett.* 350, 5-8) and of the turnip vein-clearing virus (TVCV; Lartey et al., 1994, *Arch. Virol.* 138, 287-298) were obtained from Prof. Atabekov front Moscow University, Russia. A viral vector containing a green fluorescence protein (GFP) gene was made in several cloning steps. The resulting construct, pICH8543 (FIG. 6A), contains in sequential order: a 787 bp fragment from the *Arabidopsis* actin 2 promoter (ACT2, ref An et al, 1996, GenBank accession AB026654, bp 57962 to 58748), the 5' end of TVCV (GenBank accession BRU03387, bp 1 to 5455), a fragment of cr-TMV (GenBank accession Z29370, bp 5457 to 5677, with thymine 5606 changed to cytosine to remove the start codon of the coat protein, CP), sequences “taa tcg ata act cga g”, a synthetic GFP (sGFP) gene, cr-TMV 3' nontranslated region (3' NTR; GenBank accession Z29370, bp 6078 to 6312), and finally the nopaline synthase (Nos) terminator. The entire fragment was cloned between the T-DNA left (LB) and right (RB) borders of pICBV10, a $Carb^R$ pBIN19-derived binary vector. pICH8543 was transformed into *Agrobacterium* strain GV3101 and infiltrated into a *Nicotiana benthamiana* leaf. Foci of GFP fluorescence that appeared at 3 dpi grew and became confluent. Surprisingly, even though most cells in the infiltrated area finally expressed GFP due to viral replication and movement, only a fraction of the cells initiated viral replication, as detected by a number of independent GFP expressing foci. It became clear that the limiting factor is not DNA delivery to plant cells, since infiltration of *Nicotiana benthamiana* leaves with a GFP gene under control of the 35S promoter leads to GFP expression in almost every cell in the infiltrated area (not shown).

To confirm this observation, we made a viral vector construct containing a mutation in the MP. This construct, called pICH14833, is similar to pICH8543 but differs by a deletion of 389 bp in the MP gene, upstream of the EcoRI site present in the MP. The sequence of the NcoI to EcoRI fragment that includes this deletion is given in the annex as SEQ ID No. 14. The entire viral construct (from the ACT2 promoter to the Nos terminator) was cloned between the T-DNA left and right borders of pICBV49, a pBIN19-derived $Kan^R$ binary vector. Due to the deletion in the MP, replicons produced from this construct cannot move from cell to cell but are able to replicate autonomously within a cell. Cell to cell movement can be restored when MP is provided in trans, e.g. from a constitutive promoter such as the cauliflower mosaic virus 35S promoter.

To make an MP expression construct, the TVCV MP gene was amplified by PCR from cloned TVCV cDNA (GenBank accession Z29370, bp 4802 to 5628) and subcloned in a binary vector under control of the 35S promoter. The resulting construct, called pICH10745 (not shown), and pICH14833 were transformed into *Agrobacterium* strain GV3101 and various dilutions of an overnight culture were infiltrated in *Nicotiana benthamiana* leaves as described by English and colleagues (1997, Plant J., 12, 597-603), except that the infiltration media lacked acetosyringone. Infiltration of pICH14833 alone led to the appearance of a few GFP expressing cells within the infiltrated area. By counting protoplasts prepared from the infiltrated area, we found that only one to three protoplasts expressed GFP from a total of 500 protoplasts (0.2 to 0.6%). Coinfiltration of pICH14833 and pICH10745 led to the formation of GFP-expressing foci that grew from each initial GFP-expressing cell. Ultimately, due to cell-to-cell movement, a large proportion of cells in the infiltrated area expressed GFP (FIG. 7A).

RNA viruses such as tobamoviruses replicate in the cytoplasm and never enter the nucleus. Therefore, they have evolved in an environment where they are not exposed to the nuclear pre-mRNA processing machinery. As a result, it is not surprising that RNA replicon transcripts generated in the nucleus from artificial viral constructs may not be recognized and processed properly by the RNA processing machinery. Moreover, RNA replicons from viral vectors are very large: approximately 7,000 nt in the case of the replicon based on TMV. Very few plant genes have such a large size and the majority of such genes contains introns that facilitate processing of the pre-mRNAs, export from the nucleus, and that improve the stability of the processed transcripts. We therefore hypothesized that modifications of the pre-mRNAs that would increase the efficiency of accurate processing and of export of correctly processed transcripts from the nucleus to the cytosol would lead to an increase of the number of cells that would initiate viral replication. It turned out that there are two approaches can be used to make RNA virus-based vectors that can more efficiently initiate viral replication after DNA delivery to the nucleus: (1) one approach is the removal of sequence features that might induce unwanted processing events (such as alternative splicing events using cryptic splice sites, or premature termination events); (2) a second approach is the addition of introns to increase the amount of properly processed transcripts, to improve export of the RNA from the nucleus to the cytoplasm, and/or to improve stability of the transcripts.

Reference Example 2

Removal of Intron-Like Sequences Increases the Frequency of Viral RNA Replicon Formation in the Cytoplasm We analyzed the sequence of the RNA replicon from pICH4351 using the Netgenell server program (Hebsqaard et al., 1991, *J. Mol. Biol.*, 220,49-65) and noticed several intron-like sequence features that might induce alternative splicing events. One such feature is a 0.6 kb uridine-rich region (corresponding to nt 827 to 1462 in GenBank accession BRU03387) at the beginning of the RdRP (FIG. 2A of PCT/EP04/012743). This region was replaced in pICH14833 by a PCR-mutagenized sequence that differs from the original sequence by a 54 nucleotide substitution (sequence given in the annex as SEQ ID No. 15; cf. FIG. 3 of PCT/EP04/012743). The 52 nucleotide substitutions were made to replace T-rich sequences by more GC-rich sequences. All nucleotide substitutions were made silent so as not to change the RdRP protein sequence. This mutagenized fragment also contains two nucleotide substitutions (at position 829 and 1459; coordinates relative to GenBank accession BRU03387) that were introduced to remove putative cryptic splice donor and acceptor sites, respectively. To test the effect of these mutations, the resulting clone pICH15466 (FIG. 6A) was agroinfiltrated in *N. benthamiana* leaves with or without pICH10745 (movement protein in trans). Eight days after infiltration, a 10-fold increase in the number of GFP expressing cells was observed in the area infiltrated with pICH15466 (compared to pICH14833, FIG. 7). This suggests that removal of intron-like sequences from the viral amplicon prevents unwanted alternative splicing events and results in more efficient initiation of viral replication. Coinfiltration of pICH15466 and pICH10745 leads to cell-to-cell movement of the modified replicon at a similar speed as a non-modified replicon. This shows that the modification of the RNA sequence did not affect cell to cell movement of the viral vector.

Reference Example 3

Removal of Intron-Like Sequences in the MP Subgenomic Promoter

A second potentially problematic region corresponds to the MP subgenomic promoter (FIG. 2B of PCT/EP04/012743). This region is very T-rich and resembles intron sequences very closely. As a consequence, many cryptic splice donor and acceptor sites are predicted in nearby sequences by intron prediction programs. Unfortunately, modifications cannot be made easily to this region without affecting subgenomic promoter function. We decided to completely mutagenize the entire region without regard for the subgenomic promoter, and to provide MP in trans to compensate for the expected loss of MP expression. As MP will not be expressed from this construct, we also deleted most of MP sequence except for the 3' sequences that contain the CP subgenomic promoter which is required to drive expression of the gene of interest. We therefore replaced a 383 bp fragment in pICH14833 (bp 4584 to 5455 in GenBank accession BRU03387) by a 297 bp mutagenized fragment (SEQ ID No. 16). The resulting construct pICH15900 (FIG. 6A) was agroinfiltrated in *Nicotiana benthamiana* leaves with or without pICH10745. Interestingly, a huge increase in the number of cells initiating replication was detected in comparison to leaf areas infiltrated by pICH14833. By counting GFP-expressing protoplasts prepared from infiltrated leaf areas, we estimate that this modification results in a 80 to 100-fold increase in the number of cells initiating viral replication compared to the unmodified pICH14833. pICH15900 was coinfiltrated with pICH10745 (p35S-MP expression cassette) and an increase in GFP fluorescence was detected due to cell to cell movement. This increase was however very limited because so many cells already expressed GFP even in the absence of cell-to-cell movement. A 1000-fold dilution (corresponding approximately to a calculated OD of 0.004 at 600 nm) of the *agrobacterium* suspension containing pICH 15900 coinfiltrated with a 5-fold diluted suspension of *agrobacteria* containing pICH10745 (corresponding approximately to a calculated OD of 0.8 at 600 nm) gave rise to separate GFP expression foci. Fluorescent foci were as bright and of the same size as control foci obtained with pICH14833. This tells us that the modification in pICH15900 and the delivery of MP in trans do not compromise functionality of the replicon regarding the level of replication, expression of the gene of interest and cell-to-ell movement. The same constructs (pICH14933 and pICH15900, with or without pICH10745) were coinfiltrated to *Nicotiana tabacum* leaves. The modifications in pICH15900 lead to a similar increase in the number of cells initiating replication (in comparison to pICH14833) as they did in *N. benthamiana.*

Reference Example 4

Addition of Introns Improves the Frequency of Formation of Functional RNA Replicons in the Cytoplasm We tested whether the addition of introns into viral pro-replicon sequences would increase the frequency of initiation of replication. Two constructs were made, pICH15025 and pICH15034 (FIG. 6A), each containing three different *Arabidopsis thaliana* introns in two different regions of the RdRP. pICH15025 was designed to contain introns in the middle of the RdRP, while pICH15034 contains introns in the 3' erid of the RdRP, upstream of the MP subgenomic promoter. The introns were amplified by PCR from *Arabidopsis* genomic DNA and incorporated into viral sequences using PCR with primers overlapping the planned intron/exon junctions. The fragments containing the introns were subdloned into pICH14833 as an AvaI HindIII fragment (SEQ ID No. 17 in the annex) to make pICH 15025 or as a PstI NcoI fragment (SEQ ID No. 18 in the annex) to make pICH15034.

Both constructs were separately agroinfiltrated into *N. benthamiana* leaves and compared to pICH14833. Both constructs significantly increased the number of cells initiating viral replication (FIG. 7A). This increase was estimated to be on the order of a 50-fold improvement relative to pICH14833. Both constructs were also coinfiltrated with an MP expressing clone, and cell-to-cell movement was found to be identical to clones without introns. Both constructs were also tested in *N. tabacum*, and a similar improvement was observed as in *N. benthamiana* (FIG. 7B).

A third clone was made, pICH15499, which contained all 6 introns (6B, 7A, 7B). This construct was tested in *N. benthamiana* and *N. tabacum*. This construct was more efficient than each individual construct with 3 introns, but the improvement was however less than additive.

Reference Example 5

Addition of Introns and Removal of Intron-Like Sequences Increases the Frequency of the Formation of Functional RNA Replicons in the Cytoplasm Removing intron-like features and adding additional introns in one construct showed that both types of modifications can contribute to improve initiation of viral replication. We subcloned the 6 introns of pICH15499 into pICH15900, which contains the mutagenized MP subgenomic promoter region. The resulting clone pICH15860 (FIG. 6B) was infiltrated into *N. benthamiana* leaves and found to work significantly better than either parental clones within the range of approximately 50% to 90% of all protoplasts expressing GFP (FIG. 7). The best performing construct contains introns within the RdRP region and modified MP subgenomic promoter region (pICH16191, FIG. 7C). In comparison to a clone without any modification, this represents an 80- to 300-fold improvement. This construct was also coinfiltrated with a MP-expressing construct (pICH10745) and it was found that the modifications did not compromise cell-to-cell movement or replication.

Reference Example 6

Not All Intron Additions Increase the Frequency of Appearance of Functional RNA Replicons in the Cytoplasm We inserted two different *Arabidopsis* introns at the beginning of the RdRP, resulting in clone pICH15477 (the sequence of this region is shown as SEQ ID No. 19 in the annex). The sequence in this region already looks very "exon-like" (e.g. GC-rich without cryptic splice sites) before the addition of introns. No improvement on replication of viral initiation was seen with this construct. Therefore, not any addition of an intron will result in an improvement of the viral vector. It appears that the position chosen for intron insertion or mutagenesis is an important parameter. For example, all intron insertions or nucleotide substitutions that were made in regions near problematic structures such as the MP subgenomic promoter resulted in large improvements, while insertions of introns into sequences that are already "exon-like" did not.

Reference Example 7

Insertion of Introns in MP Sequences Increase the Frequency of Viral Replicon Formation We first made a frameshift in the MP by digestion with the restriction enzyme AvrII, filling and religation. We then inserted two introns in the MP. The resulting clone pICH16422 (FIG. 6B) was infiltrated in *Nicotiana benthamiana* leaves. An about 100-fold increase in the number of cells containing the functional viral replicon was detected Reference Example 8

Insertion of Introns into a MP Containing Vector Improves the Frequency of Initiation of Viral Replication of Autonomous Functional Clones A Kpn1 EcoRI fragment was subcloned from pICH15499 into pICH8543. The resulting clone, 16700 (FIG. 6B) contained a complete viral vector with 6 introns in the RdRP. This clone was infiltrated in *N. benthamiana* leaf and efficiently initiated replication. This clone was also able to move from cell to cell without the need to provide additional MP in trans.

Reference Example 9

Activation of an Inactive Replicon Stably Integrated on a Chromosome

It is also possible to stably transform intron-containing viral vector constructs in transgenic plants. To avoid deleterious viral replication that would inhibit plant growth, an inactive clone (pro-replicon) can be made by having a part of the vector present in antisense orientation (FIG. 8). Incorporation of recombination sites and of intron sequences at the extremities of the inverted fragment allow this fragment to be 'flipped' in the correct orientation by using an appropriate recombinase. Recombination sites will be completely eliminated from the replicon by splicing. Introns in the pro-replicon allow efficient initiation of replication after recombination and transcription. In one specific example, the recombination sites are located within the gene of interest and downstream of the pro-replicon. Such a configuration prevents any gene expression before recombination. Other configurations can be considered where the recombination sites are located in other areas of the pro-replicon such as in the RdRP and upstream of the promoter. Intron sequences at the recombination site have the advantage of allowing to completely remove the recombination site from the replicon, but also increases the efficiency of viral replication, as described before.

The flipped part can be located at the 3' end of the vector (as shown in FIG. 8), in the middle or at the 5' end, as shown in FIG. 9. Two constructs were made, pICH12691 (containing only one intron at the recombination site) and pICH16888 containing 6 additional introns in the RdRP. The sequence of the entire T-DNA region of pICH12691 is given in SEQ ID No. 20. pICH16888 is similar to pICH12691, but, in addition, contains the three introns described above in pICH15025 (SEQ ID No. 17) and the three introns described in pICH15034 (SEQ ID No. 18) inserted in the same position as in these constructs, respectively. Both pICH12691 and pICH16888 were stably transformed in *Nicotiana benthamiana* using Kanamycin selection as follows. The constructs pICH12691 and pICH16888 were separately immobilized into *A. tumefaciens* (GV3101) and were separately used for *Agrobacterium*-mediated leaf discs transformation of *Nicotiana* plants as described by Horsh and colleagues (1985, *Science*, 227, 1229-1231) with minor modifications. Leaf discs were co-cultivated for 30 min in an agrobacterial suspension in Murashige and Skoog (MS) basal medium supplemented with 1 mg/L of alpha-naphthaleneacetic acid (NAA), 0.5 mg/L 6-benzaminopurine (BAP), 200 microM acetosirengone (AS), pH5.5-5.6. Then leaf discs were placed on sterile Whatman® filter paper for removal of excessive liquid and transferred onto solid co-cultivation medium (0.8% agar prepared on MS supplemented as described above) for 48 hours cultivation in darkness at 22-23° C. After co-cultivation, leaf discs were placed on selective regeneration medium (0.8% agar prepared on MS supplemented with 1 mg/L BAP, 0.1 mg/L NAA, 1 mg/L MES (pH pH 5.7-5.8), 300 mg/L cefataxim, 50 mg/L kanamycin). After 3-6 weeks of cultivation on regeneration medium, the shoots regenerated from kanamycin-resistant plant cells were transferred onto rooting selective medium (0.8% agar prepared on MS supplemented with 300 mg/L cefotaxim, 200 mg/L timentin to facilitate the elimination of *agrobacterium,* 50 mg/L kanamycin, pH 5.7-5.8). Regenerated transformants were transferred to a glasshouse and tested by infiltration with a syringe without needle with an *agrobacterium* suspension containing an integrase expression construct (pICH10881: actin2 promoter—PhiC31 integrase; or pICH14313: Zea maize transposable element Spm promoter—PhiC31 integrase). More pICH16888 transformants exhibited viral replication foci after infiltration with the integrase construct than transformants of pICH12691 (FIG. 10). In addition, transformants of pICH16888 displayed more viral initiation foci per infiltration.

Reference Example 10

Plant Viral RNA Sequences Contain Potentially Unstable Regions

The analysis of RNA profile of selected plant RNA viruses as well as one well characterised plant gene (AtDMC1) was performed by using the Netgenell server program (Hebsqaard et al., 1991, *J. Mol. Biol.,* 220, 49-65). The RNA profile shown in FIG. 9 of PCT/EP04/012743 for AtDMC1 clearly reflects the presence of 14 introns (circled), previously identified by comparing the cDNA and genomic DNA sequences. It is evident that RNA profiles of two plant viruses have regions (see the FIGS. 10, 11 of PCT/EP04/012743) which might cause problems for the stability of said RNA, if they are placed in plant nuclear environment. We have analysed the RNA profiles of several other representatives of plant RNA viruses (not shown), such as Brome Mosaic Virus, different strains of TMV, and many others. All of them have potential problematic regions that might compromise the efficiency of plant RNA virus-based replicon formation if delivered into the plant cell as DNA precursors.

Reference Example 11

Optimized Vectors Work in Other Species

A fully optimized construct containing the mutagenized region (described in pICH15466) and 16 introns (including the six introns of pICH15860, the two introns of pICH16422 and eight additional introns) was made. In summary this construct contains introns inserted at the following positions (given relative to TVCV sequence, GenBank accession BRU03387): nt 209, nt 828, nt 1169, nt 1378, nt 1622, nt 1844, nt 2228, nt 2589, nt 2944, nt 3143, nt 3381, nt 3672, nt 3850, nt 4299, nt 5287, nt 5444.

This construct was tested for expression in *Beta vulgaris*. Infiltration of the entire plant was performed as described next. *Agrobacteria* carrying pICH18711 were inoculated to 300 ml of LB containing 50 μg/ml Rifampicin and 50 μg/ml Kanamycin (selection for the binary vector) and grown until saturation. The bacteria were pelleted at 4800 g for 10 min and resuspended in 3 l of infiltration buffer (10 mM MES pH 5.5, 10 mM MgSO$_4$) in order get a 10-fold dilution relative to the saturated *Agrobacterium* culture. A beaker containing the infiltration solution was placed in an exsiccator (30 mm diameter), with the aerial parts of a plant dipped in the solution. A vacuum was applied for two minutes using a Type PM 16763-860.3 pump from KNF Neuberger (Freiburg, Germany), reaching from 0.5 to 0.9 bar. The plants were returned to the greenhouse under standard conditions.

GFP expression was high in leaves of the plants infiltrated with pICH18711 (FIG. 11). In contrast, only a few small spots could be seen in control plants infiltrated with pICH 16700 containing no intron (not shown).

ANNEX
SEQ ID No. 1: intron 1
gtaaatcctggtccacactttacgataaaaacacaagattttaaactat gaactgatcaataatcattcctaaaagaccacacttttgttttgtttcta aagtaatttttactgttataacag SEQ ID No. 2: intron 2
gtaagaggtcaaaaggtttccgcaatgatccctcttttttgtttctcta gtttcaagaatttgggtatatgactaacttctgagtgttccttgatgcat atttgtgatgagacaaatgtttgttctatgttttag SEQ ID No. 3: intron 3
gtaagttctgcatttggttatgctccttgcattttaggtgttcgtcgctc ttccatttccatgaatagctaagatttttttctctgcattcattcttct tgcctcagttctaactgtttgtggtattttgttttaattattgctacag SEQ ID No. 4: intron 4
gtaaagcaactgtgttttaatcaatttcttgtcaggatatatggattata acttaattttgagaaatctgtagtatttggcgtgaaatgagtttgcttt ttggtttctcccgtgttatag SEQ ID No. 5: intron 5
gtaaagtttccaactttccttaccatatcaaactaaagttcgaaacttt ttatttgatcaacttcaaggccacccgatctttctattcctgattaattt gtgatgaatccatattgacttttgatggttacgcag SEQ ID No. 6: intron 6
gtctgtctttcctatttcatatgtttaatcctaggaatttgatcaattga ttgtatgtatgtcgatcccaagactttcttgttcacttatatcttaactc tctctttgctgtttcttgcag SEQ ID No. 7: intron 7
gtaaaatattggatgccagacgatattctttcttttgatttgtaacttt tcctgtcaaggtcgataaattttatttttttggtaaaaggtcgataatt ttttttggagccattatgtaattttcctaattaactgaaccaaaattat acaaaccag SEQ ID No. 8: intron 8
gtaaggacttctcatgaatattagtggcagattagtgttgttaaagtctt tggttagataatcgatgcctcctaattgtccatgttttactggttttcta caattaaag SEQ ID No. 9: intron 9
gtgagttcctaagttccatttttttgtaatccttcaatgttattttaact tttcagatcaacatcaaaattaggttcaattttcatcaaccaaataatat ttttcatgtatatatag SEQ ID No. 10: intron 10
gtaagttttccactttaagaaaattactagcactaaatttacgaattt
aactatacaattatggatgtaaccaccattttaaattaatcttgaaccag
acgatatggattacaaacattcttgttttaatcggctggttagctattgc
atttgcag SEQ ID No. 11: intron 11
gtaaggattttatgatatagtatgcttatgtattttgtactgaaagcat
atcctgcttcattgggatattactgaaagcatttaactacatgtaaactc
acttgatgatcaataaacttgattttgcag SEQ ID No. 12: intron 12
gtaagccatcttcctgcttattttataatgaacatagaaataggaagtt
gtgcagagaaactaattaacctgactcaaaatctaccctcataattgttg
tttgatattggtcttgtattttgcag SEQ ID No. 13: Seq1
cggacgatacgtgatccaccatgatagaggagccattgtgtattacgatc
cgcttaaactaatatctaagctcggctgcaagcacatcagagacgtcgtg
cacttagaagagttacgcgagtctttgtgcgacgtagctagtaacttgaa
caactgcgcctacttctcacagttagatgaggccgttgctgaggtccaca
agactgcggtcggaggctccttcgcgttctgtagcatcatcaaatacttg
tcagacaagaggctgttcagggacctgttcttcgtctgagttgacgaatt
c SEQ ID No. 14 (NcoI-EcoRI fragment of pICH14833):
ccatggacaaagtgataaaggcagcttttttgtggagacgatagcctgatt
tacattcctaaaggtttagacttgcctgatatattcaggcgggcgcgaacct
catgtggaacttcgaggccaaactcttcaggaagaagtatggttacttct
gtggtcgttatgttattcaccatgatagaggagccattgtgtattacgat
ccgcttaaactaatatctaagttaggttgtaaacatattagagatgttgt
tcacttagaagagttacgcgagtctttgtgtgatgtagctagtaacttaa
ataattgtgcgtattttttcacagttagatgaggccgttgccgaggttcat
aagaccgcggtaggcggttcgtttgcttttgtagtataattaagtatttt
gtcagataagagattgtttagagatttgttctttgtttgataatgtcgat
agtctcgtacgaacctaaggtgagtgatttcctcaatctttcgaagaagg
aagagatcttgccgaaggctctaacgaggttagaattc SEQ ID No. 15 (part of pICH15466):
ggagataaacctgagcttcttcttccataatgagagcactctcaattacac
ccacagcttcagcaacatcatcaagtacgtgtgcaagacgttcttccctg
ctagtcaacgcttcgtgtaccacaaggagttcctggtcactagagtcaac
acttggtactgcaagttcacgagagtggatacgttcactctgttccgtgg
tgtgtaccacaacaatgtggattgcgaagagttttacaaggctatggacg
atgcgtggcactacaaaaagacgttagcaatgcttaatgccgagaggacc
atcttcaaggataacgctcgttaaacttttggttcccgaaagtgagaga
catggttatcgtccctctcttttgacgcttctatcacaactggtaggatgt
ctaggagagaggttatggtgaacaaggacttcgtctacacgtcctaaat
cacatcaagacctatcaagctaaggcactgacgtacgcaaacgtgctgag
cttcgtggagtctattaggtctagagtcataattaacggtgtcactgcca
ggtctgaatgggacacagacaaggcaattctaggtccattagcaatgaca
ttcttcctgatcacgaagctgggtcatgtgcaagat SEQ ID No.16 (part of pICH15900):
gcggacgatacgtgatccaccatgatagaggagccattgtgtattacgat
ccgcttaaactaatatctaagctcggctgcaagcacatcagagacgtcgt
gcacttagaagagttacgcgagtctttgtgcgacgtagctagtaacttga
acaactgcgcctacttctcacagttagatgaggccgttgctgaggtccac
aagactgcggtcggaggctccttcgcgttctgtagcatcatcaaatactt
gtcagacaagaggctgttcagggacctgttcttcgtctgagttgacg SEQ ID No.17 (part of pICH15025):
(contains 3 Introns shown underlined in italics)
Cccgagctatactgtaccttcgccgaccgattggtactacagtacaagaa
ggcggaggagttccaatcgtgtgatctttccaaacctctagaagagtcag
agaagtactacaacgcattatccgagctatcagtgcttgagaatctcgac
tcttttgacttagaggcgtttaagactttatgtcagcagaagaatgtgga
cccggatatggcagcaaag*gtaaatcctggtccacacttttacgataaaa*
*acacaagatttaaactatgaactgatcaataatcattcctaaaagacca*
*cacttttgttttgtttctaaagtaattttactgttataacaggtggtcg*
tagcaatcatgaagtcagaattgacgttgcctttcaagaaacctacagaa
gaggaaatctcggagtcgctaaaaccaggagaggggtcgtgtgcagagca
taaggaagtgttgagcttacaaaatgatgctccgttcccgtgtgtgaaaa
atctagttgaaggttccgtgccggcgtatggaatgtgtcctaagggtggt
ggtttcgacaaaattggatgtggacattgctgatttccatctcaagagtgt
agatgcagttaaaaagggaactatgatgtctgcggtgtacacagggtcta
tcaaagttcaacaaatgaagaactacatagattacttaagtgcgtcgctg
gcagctacagtctcaaacctctgcaag*gtaagaggtcaaaaggtttccgc*
*aatgatccctctttttttgtttctctagtttcaagaatttgggtatatga*
*ctaacttctgagtgttccttgatgcatatttgtgatgagacaaatatttg*
*ttctatgttttaggtgcttagagatgttcacggcgttgacccagagtcac*
aggagaaatctggagtgtgggatgttaggagaggacgttggttacttaaa
cctaatgcgaaaagtcacgcgtggggtgtggcagaagacgccaaccacaa
gttggttattgtgttactcaactgggatgacggaaagccggtttgtgatg
agacatggttcagggtggcggtgtcaagcgattccttgatatattcggat
atgggaaaacttaagacgctcacgtcttgcagtccaaatggtgagccacc
ggagcctaacgccaaagtaattttggtcgatggtgttcccggttgtggaa
aaacgaaggagattatcgaaaag*gtaagttctgcatttggttatgctcct*
*tgcattttaggtgttcgtcgctcttccatttccatgaatagctaagattt*
*ttttctctgcattcattcttcttgcctcagttctaactgtttgtggtat*
*ttttgttttaattattgctacacggtaaacttctctgaagacttgatttt*
agtccctgggaaggaagctt SEQ ID No. 18 (part of pICH15034):
(contains 3 Introns shown underlined in italics)
ctgcag*gtaaaatattggatgccagacgatattctttcttttgatttgta*

*actttttcctgtcaaggtcgataaattttatttttttggtaaaaggtcg*

*ataatttttttttcggagccattatgtaattttcctaattaactgaacca*

*aaattatacaaaccaggtttgctggaaaatttggttgcaatgatcaaag* aaacatgaatgcgccggatttgacagggacaattgacattgaggatactg catctctggtggttgaaaagttttgggattcgtatgttgacaaggaattt agtggaacgaacgaaatgaccatgacaagggagagcttctccag*gtaagg*

*acttctcatgaatattagtggcagattagtgttgttaaagtctttggtta*

*gataatcgatgcctcctaattgtccatgttttactggttttctacaatta*

*aaggtggctttcgaaacaagagtcatctacagttggtcagttagcggact* ttaactttgtggatttgccggcagtagatgagtacaagcatatgatcaag agtcaaccaaagcaaaagttagacttgagtattcaagacgaatatcctgc attgcagacgatagtctaccattcgaaaaagatcaatgcgattttcggtc caatgttttcagaacttacgaggatgttactcgaaaggattgactcttcg aagtttctgttctacaccagaaagacacctgcacaaatagaggacttctt ttctgacctagactcaacccaggcgatggaaattctggaactcgacattt cgaagtacgataagtcacaaaacgagttccattgtgctgtagagtacaag atctgggaaaagttaggaattgatgagtggctagctgaggtctggaaaca ag*gtgagttcctaagttccattttttgtaatccttcaatgttattttaa*

*cttttcagatcaacatcaaaattaggttcaattttcatcaaccaaataat*

*attttcatgtatatataggt*cacagaaaaacgaccttgaaagattatac ggccggaatcaaaacatgtctttggtatcaaaggaaaagtggtgatgtga caacctttattggtaataccatcatcattgccgcatgtttgagctcaatg atccccatgg SEQ ID No. 19 (fragment of pICH15477, containing 1 Intron shown in underlined italics)
Gttttagttttattgcaacaacaacaacaaattacaataacaacaaacaa aatacaaacaacaacatggcacaatttcaacaaacaattgacatgca aactctccaagccgctgcgggacgcaacagcttggtgaatgatttggcat ctcgtcgcgtttacgataatgcagtcgaggagctgaatgctcgttccaga cgtcccaag*gtaaaacaacatttcattcacatatatgaatactttgtca*

*ttgagtacgaagaagacacttactacttgttaatgaaagtttccgcctt*

*atacttatctatatcattttcatcattcaaactagtatgaaattaggtg*

*atgtttatatgatatcatggaacattaatctataggaaactgttttgag*

*ttagttttgtataatatttttccctgtttgatgttaggttcatttctcca* aggcagtgtctacggaacagacactgattgcaacaaacgcatatccggag ttcgagatttcctttactcatacgcaatccgctgtgcactccttggccgg aggccttcggtcacttgagttggagtatctcatgatgcaagttccgttcg gctctctgacctacgacatcggcggaaacttctccgcgcacctcttcaaa ggtaattttctttctctactcaattttctccaagatccaatatttgaaga ctgatctatagttaaaattaatctctactccattcttgttacctcaggtc gcgattacgttcactgctgcatgc:gttttagttttattgcaacaacaac aacaaattacaataacaacaaacaaaatacaaacaacaacatggcac aatttcaacaaacaattgacatgcaaactctccaagccgctgcgggacgc aacagcttggtgaatgatttggcatctcgtcgcgtttacgataatgcagt cgaggagctgaatgctcgttccagacgtcccaaggtaaaacaacatttca ttcacatatatgaatactttgtcattgagtacgaagaagacacttacta cttgttgatgaaagtttccgcctttatacttatctatatcattttcatca tttcaaactagtatgaaattaggtgatgtttatatgatatcatggaacat taatctatagggaaactgttttgagttagttttgtataatatttttccct gtttgatgttaggttcatttctccaaggcagtgtctacggaacagacact gattgcaacaaacgcatatccggagttcgagatttcctttactcatacgc aatccgctgtgcactccttggccggaggccttcggtcacttgagttggag tatctcatgatgcaagttccgttcggctctctgacctacgacatcggcgg aaacttctccgcgcacctcttcaaaggtaattttctttctctactcaatt ttctccaagatccaatatttgaagactgatctatagttaaaattaatctc tactccattcttgttaoctcaggtcgcgattacgttcactgctgcatgc SEQ ID No. 20: T-DNA region of pICH12691, wherein sequence segments have the following function:
Nucleotides 1 to 25: Left border (opposite strand),
Nucleotides 86 to 1484: Nos promoter-NPTII coding sequence-Nos terminator (on the opposite strand),
Nucleotides 1506 to 1552: AttP recombination site (opposite strand),
Nucleotides 1553 to 1599: intron 5' part (opposite strand),
Nucleotides 1600 to 2022: TVCV RdRP 5' end (opposite strand),
Nucleotides 2023 to 2809: *Arabidopsis* actin 2 promoter (opposite strand),
Nucleotides 2836 to 2903: AttB recombination site,
Nucleotides 2904 to 2959: intron 3' part,
Nucleotides 2960 to 7991: TVCV RdRP 3' part-MP 5' part,
Nucleotides 7992 to 8168: cr-TMV MP 3' end,
Nucleotides 8248 to 8967: GFP coding sequence
Nucleotides 8961 to 9215: cr-TMV 3' untranslated region,
Nucleotides 9234 to 9497: Nos terminator,
Nucleotides 9549 to 9473: T-DNA right border (opposite strand):

tggcaggatatattgtggtgtaaacaaattgacgcttagacaacttaata acacattgcggacgttttaatgtactggggtggatgcaggtcgatctag taacatagatgacaccgcgcgcgataatttatcctagtttgcgcgctata ttttgttttctatcgcgtattaaatgtataattgcgggactctaatcata aaaaccatctcataaataacgtcatgcattacatgttaattattacatg cttaacgtaattcaacagaaattatatgataatcatcgcaagaccggcaa caggattcaatcttaagaaactttattgccaaatgtttgaacgatctgct tgactctagatccagagtcccgctcagaagaactcgtcaagaaggcgata gaaggcgatgcgctgcgaatcgggagcggcgataccgtaaagcacgagga agcggtcagcccattcgccgccaagctcttcagcaatatcacgggtagcc aacgctatgtcctgatagcggtccgccacacccagccggccacagtcgat
gaatccagaaaagcggccattttccaccatgatattcggcaagcaggcat
cgccatgagtcacgacgagatcctcgccgtcgggcatacgcgccttgagc
ctggcgaacagttcggctggcgcgagcccctgatgctcttcgtccagatc
atcctgatcgacaagaccggcttccatccgagtacgtgctcgctcgatgc
gatgtttcgcttggtggtcgaatgggcaggtagccggatcaagcgtatgc
agccgccgcattgcatcagccatgatggatactttctcggcaggagcaag
gtgagatgacaggagatcctgccccggcacttcgcccaatagcagccagt
cccttcccgcttcagtgacaacgtcgagcacagctgcgcaaggaacgccc
gtcgtggccagccacgatagccgcgctgcctcgtcctggagttcattcag
ggcaccggacaggtcggtcttgacaaaagaaccgggcgccctgcgctg
acagccggaacacggcggcatcagagcagccgattgtctgttgtgccag
tcatagccgaatagcctctccacccaagcggccggagaacctgcgtgcaa
tccatcttgttcaatcatgcgaaacgatccagatccggtgcagattattt
ggattgagagtgaatatgagactctaattggataccgaggggaatttatg
gaacgtcagtggagcatttttgacaagaaatatttgctagctgatagtga
ccttaggcgacttttgaacgcgcaataatggtttctgacgtatgtgctta
gctcattaaactccagaaaccgcggctgagtggctccttcaacgttgcg
gttctgtcagttccaaacgtaaaacggcttgtcccgcgtcatcggcgggg
gtcataacgtgactcccttaattctccgctcatggtaccagcttctcgag
cgaccctacgccccaactgagagaactcaaaggttaccccagttgggc
acaacaaaaatcaaatctaaatttgtgtaattatgaaaatgaaacttacc
tttgaagaggtgcgcggagaagtttccgccgatgtcgtaggtcagagagc
cgaacggaacttgcatcatgagatactccaactcaagtgaccgaaggcct
ccggccaaggagtgcacagcggattgcgtatgagtaaaggaaatctcgaa
ctccggatatgcgtttgttgcaatcagtgtctgttccgtagacactgcct
tggagaaatgaaccttgggacgtctgaacgagcattcagctcctcgact
gcattatcgtaaacgcgacgagatgccaaatcattcaccaagctgttgcg
tcccgcagcggcttggagagtttgcatgtcaattgtttgttgaaattgtg
ccatgttgttgttgtttgtattttgtttgttgttattgtaatttgttgtt
gttgttgcaataaaactaaaacttcaaagcggagaggaaaatatatgaat
ttatataggcgggtttatctcttacaactttattttcggcctttcaaaaa
aataattaaaatcgacagacacgaatcatttcgaccacaggtaaagataa
cgtgacctggctgtcagacagccttttccctcgtgttaactaatttttaa
actaattaatcatctcagcccttggattagttcttttgctttgatggctt
catgactgtgacctgctcgatccgcgtgttacatgacagctccgtttttt
tagtggttaacttaaaccgagtcaatccaggcaacgttagtcgtcgtcgt
ggttggcttgttcaattagtttcatacaattcaacgtaatttaattcgt
tttctattagaattgtatcataattaattcagaccgtgaaagaaagtgtc
tttcatgatgtgtttatggatatttatacaataagatacaatgtttcatc atattcactattcacgattagtatgtacattaaataatggctactactac
atccgaactcgtcaaaacgattctgaatcaattatacatatgctgactct
tgcatacataaaaaatagttgtttaaattttgtctaactaatgtttggta
taagtataatgttgagttgagataccaattacatcgagtctagccatttt
gtcgtgccatattcgtcaaaactttcttacataatgataacctagatcta
gatgagatatgtatcaatgtatttgagatcataattaagttcgttctaaa
ttttgtcgaaacgcgtggtacgctgcagaattgctcgaagccgcggtgcg
ggtgccagggcgtgcccttgggctccccgggcgcgtactccacctcaccc
atctttattacatgtttgaacttcaacaatttatgactttttgttctta
ttgttgcaggtcgcgattacgttcactgctgcatgcctaatctggatgta
cgtgacattgctcgccatgaaggacacaaggaagctatttacagttatgt
gaatcgtttgaaaaggcagcagcgtcctgtgcctgaataccagagggcag
ctttcaacaactacgctgagaacccgcacttcgtccattgcgacaaacct
ttccaacagtgtgaattgacgacagcgtatggcactgacacctacgctgt
agctctccatagcatttatgatatccctgttgaggagttcggttctgcgc
tactcaggaagaatgtgaaaacttgtttcgcggcctttcatttccatgag
aatatgcttctagattgtgatacagtcacactcgatgagattggagctac
ttttcagaagtccggtgataatttaagttttttctttcataatgagagca
ctctcaattacacccacagttttagtaatataattaagtatgtgtgtaaa
acgttctttcctgctagtcaacggtttgtgtatcataaggagttttagt
tactagagtcaacacttggtactgtaagtttacgagagtggatacttta
ctcttttccgtggtgtgtaccataataatgtggattgcgaagagttttac
aaggctatggacgatgcgtggcactacaaaaagacgttagcaatgcttaa
tgccgagaggaccatcttcaaggataacgctgcgttaaacttttggttcc
cgaaagtgagagacatggttatcgtccctctctttgacgcttctatcaca
actggtaggatgtctaggagagagattatggtgaacaaggatttcgttta
tacggtcctaaatcacataaaaacgtatcaagctaaggctttaacttacg
caaatgttctgtcctttgtggagtctattaggtctagagtgataattaac
ggtgtcactgccaggtctgaatgggacacagacaaggcaattctaggtcc
attagcaatgacattttccttataacaaagttgggtcatgtgcaggatg
aaataatcctgaaaaagttccagaagttcgacagaaccaccaatgagctg
atttggacaagtctctgcgatgccctgatgggggttattccctcggtcaa
ggagacgcttgtgcgcggtggttttgtgaaagtagcagaacaagccttag
agataaaggttcccgagctatactgtacctttgccgacagattggtacta
cagtacaagaaggcggaggagttccaatcgtgtgatcttccaaacctct
agaagagtcagagaagtactacaacgcattatccgagctatcagtgcttg
agaatctcgactcttttgacttagaggcgtttaagactttatgtcagcag
aagaatgtggaccggatatggcagcaaaggtggtcgtagcaatcatgaa
gtcagaattgacgttgcctttcaagaaacctacagaagaggaaatctcgg
agtcgctaaaaccaggagaggggtcgtgtgcagagcataaggaagtgttg
agcttacaaaatgatgctccgttcccgtgtgtgaaaaatctagttgaagg -continued ttccgtgccggcgtatggaatgtgtcctaagggtggtggtttcgacaaat
tggatgtggacattgctgatttccatctcaagagtgtagatgcagttaaa
aagggaactatgatgtctgcggtgtacacagggtctatcaaagttcaaca
aatgaagaactacatagattacttaagtgcgtcgctggcagctacagtct
caaacctctgcaaggtgcttagagatgttcacggcgttgacccagagtca
caggagaaatctggagtgtgggatgttaggagaggacgttggttacttaa
acctaatgcgaaaagtcacgcgtggggtgtggcagaagacgccaaccaca
agttggttattgtgttactcaactgggatgacggaaagccggtttgtgat
gagacatggttcagggtggcggtgtcaagcgattccttgatatattcgga
tatgggaaaacttaagacgctcacgtcttgcagtccaaatggtgagccac
cggagcctaacgccaaagtaattttggtcgatggtgttcccggttgtgga
aaaacgaaggagattatcgaaaaggtaaacttctctgaagacttgatttt
agtccctgggaaggaagcttctaagatgatcatccggagggccaaccaag
ctggtgtgataagagcggataaggacaatgttagaacggtggattccttc
ttgatgcatccttctagaagggtgtttaagaggttgtttatcgatgaagg
actaatgctgcatacaggttgtgtaaatttcctactgctgctatctcaat
gtgacgtcgcatatgtgtatggggacacaaagcaaattccgttcatttgc
agagtcgcgaactttccgtatccagcgcattttgcaaaactcgtcgctga
tgagaaggaggttagaagagttacgctcaggtgcccggctgatgttacgt
atttccttaacaagaagtatgacggggcggtgatgtgtaccagcgcggta
gagagatccgtgaaggcagaagtggtgagaggaaagggtgcattgaaccc
aataaccttaccgttggagggtaaaattttgaccttcacacaagctgaca
agttcgagttactgagaaagggttacaaggatgtgaacactgtgcacgag
gtgcaagggagacgtacgagaagactgctattgtgcgcttgacatcaac
tccgttagagatcatatcgagtgcgtcacctcatgttttggtggcgctga
caagacacacaacgtgttgtaaatattacaccgttgtgttggacccgatg
gtgaatgtgatttcagaaatggagaagttgtccaatttccttcttgacat
gtatagagttgaagcggggtccaatagcaattacagatcgatgcagtat
tcagggacagcaacttgtttgttcagacgcccaagtcaggagattggcga
gatatgcaattttactatgacgctcttcttcccggaaacagtactattct
caatgaatttgatgctgttacgatgaatttgagggatattccttaaacg
tcaaagattgcagaatcgacttctccaaatccgtgcaacttcctaaagaa
caacctattttcctcaagcctaaaataagaatgcggcagaaatgccgaac
tgcaggtttgctggaaaatttggttgcaatgatcaaaagaaacatgaatg
cgccggatttgacagggacaattgacattgaggatactgcatctctggtg
gttgaaaagttttgggattcgtatgttgacaaggaatttagtggaacgaa
cgaaatgaccatgacaagggaaagttttctagatggctttcgaaacaag
agtcatctacagttggtcagttagcggactttaactttgtggatttgccg
gcagtagatgagtacaagcatatgatcaagagtcaaccaaagcaaaagtt
agacttgagtattcaagacgaatatcctgcattgcagacgatagtctacc -continued attcgaaaagatcaatgcgattttcggtccaatgttttcagaacttacg
aggatgttactcgaaaggattgactcttcgaagtttctgttctacaccag
aaagacacctgcacaaatagaggacttcttttctgacctagactcaaccc
aggcgatggaaattctggaactcgacatttcgaagtacgataagtcacaa
aacgagttccattgtgctgtagagtacaagatctgggaaaagttaggaat
tgatgagtggctagctgaggtatggaaacaaggacacagaaaaacgacct
tgaaagattatacggccggagtcaaaacatgtctttggtatcaaaggaaa
agtggtgatgtgacaacctttattggtaataccatcatcattgcagcctg
tttgagctcaatgatccccatggacaaagtgataaaggcagcttttttgtg
gagacgatagcctgatttacattcctaaaggtttagacttgcctgatatt
caggcgggcgcgaacctcatgtggaacttcgaggccaaactcttcaggaa
gaagtatggttacttctgtggtcgttatgttattcaccatgatagaggag
ccattgtgtattacgatccgcttaaactaatatctaagttaggttgtaaa
catattagagatgttgttcacttagaagagttacgcgagtctttgtgtga
tgtagctagtaacttaaataattgtgcgtatttttcacagttagatgagg
ccgttgccgaggttcataagaccgcggtaggcggttcgtttgcttttttgt
agtataattaagtatttgtcagataagagattgtttagagatttgttctt
tgataatgcgatagtctcgtacgaacctaaggtgagtgatttcctcaatc
tttcgaagaaggaagagatcttgccgaaggctctaacgaggttaaaaccg
tgtctattagtactaaagatattatatctgtcaaggagtcggagactttg
tgtgatatagatttgttaatcaatgtgccattagataagtatagatatgt
gggtatcctaggagctgttttttaccggagagtggctagtgccagacttcg
ttaaaggtggagtgacgataagtgtgatagataaagcgtctggtgaactc
aaaggagtgcgtgattggtacgtacagagccgcagccaagagtaagaggt
tccagttcaaattggttccaaaattactttgtgtccaccgtggacgcaaag
aggaagccgtggcaggttcatgttcgtatacaagacttgaagattgaggc
gggttggcagccgttagctctggaagtagtttcagttgctatggtcacca
ataacgttgtcatgaagggtttgagggaaaaggtcgtcgcaataaatgat
ccggacgtcgaaggtttcgaaggtgtggttgacgaattcgtcgattcggt
tgcagcattttaaagcggttgacaactttaaaagaaggaaaaagaaggttg
gttgaagaaagggtgtagtaagtaagtataagtacagaccggagaagta
cgccggtcctgattcgtttaatttgaaagaagaaaacgtcttacaacatt
acaaacccgaataatcgataactcgagtattttttacaacaattaccaaca
acaacaaacaacaaacaacattacaattacatttacaattatcatggtga
gcaagggcgaggagctgttcaccggggtggtgcccatcctggtcgagctg
gacggcgagtaaacggccacaagttcagcgtgtccggcgagggcgagggc
gatgccacctacggcaagctgaccctgaagttcatctgcaccaccggcaa
gctgcccgtgccctgcccggcccacctcgtgaccaccttcagctaggc
gtgcagtgcttcagccgctaccccgaccacatgaagcagcacgacttctt
caagtccgccatgcccgaaggctacgtccaggagcgcaccatcttcttca
aggacgacggcaactacaagacccgcgccgaggtgaagttcgagggcgac cctggtgaaccgcatcgagctgaagggcatcgacttcaaggaggacggca acatcctggggcacaagctggagtacaactacaacagccacaacgtctat atcatggccgacaagcagaagaacggcatcaaggtgaacttcaagatccg ccacaacatcgaggacggcagcgtgcagctcgccgaccactaccagcaga acacccatcggcgaggccccgtgctgcccgacaaccactacctgagcac ccagtccgccctgagcaaagacccccaacgagaagcgcgatcatggtcctg ctggagttcgtgaccgccgccgggatcactcacggcatggacgagctgta caagtaaagcggcccctagagcgtggtgcgcacgatagcgcatagtgttt ttctctccacttgaatcgaagagatagacttacggtgtaaatccgtaggg gtggcgtaaaccaaattacgcaatgttttgggttccatttaaatcgaaac cccttatttcctggatcacctgttaacgcacgtttgacgtgtattacagt gggaataagtaaaagtgagaggttcgaatcctccctaaccccgggtaggg gcccagcggccgctctagctagagtcaagcagatcgttcaaacatttggc aataaagtttcttaagattgaatcctgttgccggtcttgcgatgattatc atataatttctgttgaattacgttaagcatgtaataattaacatgtaatg catgacgttatttatgagatgggttttttatgattagagtcccgcaattat acatttaatacgcgatagaaaacaaaatatagcgcgcaaactaggataaa ttatcgcgcgcggtgtcatctatgttactagatcgaccgcttagatcaga ttgtcgtttcccgccttcagtttaaactatcagtgtttgacaggatatat tggcgggtaaac

---

The invention claimed is:

1. A system for replicating or for replicating and expressing a sequence of interest in a plant, comprising:
  (i) a DNA precursor of an RNA replicon, said RNA replicon derived from a tobamovirus and comprising at least one sequence of interest, said DNA precursor of said RNA replicon containing in a tobamoviral replicase open reading frame (ORF) or in a tobamoviral movement protein ORF of said RNA replicon, one or more introns inserted within A/U rich localities of said tobamoviral replicase ORF or said tobamoviral movement protein ORF; and
  (ii) a DNA precursor of a helper replicon, wherein said helper replicon is
    (a) incapable of systemic movement in a plant both in the presence and in the absence of said RNA replicon (i) and
    (b) capable of expressing in a plant or more proteins necessary for systemic movement of said RNA replicon (i),
  whereby said RNA replicon (i) is capable of replication or of replicating and expressing said sequence of interest in a plant, but unable to move systemically in a plant in the absence of said one or more proteins expressed by said helper replicon (ii).

2. The system according to claim 1, wherein said helper replicon (ii) is incapable of systemic movement in a plant due to the absence of a functional origin of viral particle assembly.

3. The system according to claim 1, wherein said helper replicon (ii) is capable of expressing in a plant a coat protein and/or a movement protein necessary or useful for said systemic movement of said RNA replicon (i) in said plant.

4. The system according to claim 1, wherein said RNA replicon (i) cannot express a protein necessary for systemic movement of said RNA replicon (i) in said plant.

5. The system according to claim 4, wherein said RNA replicon (i) lacks a coat protein open reading frame and said sequence of interest is larger than 1 kb.

6. The system according to claim 1, wherein said tobamovirus is a tobacco mosaic virus.

7. The system according to claim 1, wherein said RNA replicon (i) is based on a tobamovirus wherein the coat protein open reading frame is replaced by said sequence of interest.

8. The system according to claim 1, wherein said precursor of said helper replicon (ii) is DNA encoding said helper replicon (ii), whereby said DNA is capable of producing said helper replicon (ii) in cells of said plant.

9. The system according to claim 1, wherein said precursor of said RNA replicon (i) or said precursor of said helper replicon (ii) are carried by agrobacteria.

10. The system according to claim 1, wherein the system further comprises a plant, or seeds thereof, for replicating or for replicating and expressing said sequence of interest.

11. The system according to claim 1, wherein said plant is a dicot plant.

12. The system according to claim 1, wherein said plant is transgenic and expresses a viral protein necessary or useful for cell-to-cell movement of said RNA replicon (i).

13. The system according to claim 12, wherein said viral protein is a movement protein of tobacco mosaic virus.

14. The system according to claim 1, wherein said RNA replicon (i) and said helper replicon (ii) lack homology in functionally overlapping regions.

15. The system according to claim 1, whereby said RNA replicon (i) and said helper replicon (ii) lack a recombination-prone homology in a region recombination in which between said RNA replicon (i) and said helper replicon (ii) would create an RNA replicon capable of expressing a protein necessary for systemic movement and capable of moving systemically in said plant.

16. The system according to claim 1, wherein the sequence homology between said RNA replicon (i) and said helper replicon (ii) in any sequence segments having at least 100 nucleotides is at most 80%.

17. The system according to claim 16, wherein said sequence segments are located downstream of the replicase ORFs of said RNA replicon (i) and said helper replicon (ii).

18. The system according to claim 1, wherein said helper replicon (ii) lacks a movement protein ORF but contains a replicase ORF and an ORF encoding a protein necessary for systemic movement of said RNA replicon (i), the latter ORF being under the control of a subgenomic promoter, said subgenomic promoter being derived from an RNA virus of a strain different from the RNA virus from which the subgenomic promoter controlling expression of said sequence of interest in said RNA replicon (i) is derived.

19. The system according to claim 1, wherein the sequence of said RNA replicon (i) and the sequence of said helper replicon (ii) do not overlap.

20. The system according to claim 1, wherein said DNA precursor of said RNA replicon (i) contains one or more introns in the replicase ORF of said RNA replicon (i).

21. A process for replicating or for replicating and expressing a sequence of interest in a plant, comprising providing cells of a plant with
- (i) a DNA precursor of an RNA replicon, said RNA replicon derived from a tobamovirus and comprising at least one sequence of interest, said DNA precursor of said RNA replicon containing in a tobamoviral replicase open reading frame (ORF) or in a tobamoviral movement protein ORF of said RNA replicon, one or more introns inserted within A/U rich localities of said tobamoviral replicase ORF or said tobamoviral movement protein ORF; and
- (ii) a DNA precursor of a helper replicon, wherein said helper replicon is
  - (a) incapable of systemic movement in a plant both in the presence and in the absence of said RNA replicon (i) and
  - (b) capable of expressing in a plant or more proteins necessary for systemic movement of said RNA replicon (i),
- whereby said RNA replicon (i) is capable of replication or of replicating and expressing said sequence of interest in a plant, but unable to move systemically in a plant in the absence of said one or more proteins expressed by said helper replicon (ii).

22. The process according to claim 21, wherein said plant is provided with said RNA replicon (i) and/or said helper replicon (ii) by transfecting with agrobacteria containing in their T-DNA said precursor of said replicon (i) and/or with agrobacteria containing in their T-DNA said precursor of said helper replicon (ii).

23. The process according to claim 21, wherein a part of said plant like a leaf is provided with said RNA replicon (i) and said helper replicon (ii) but not other parts of said plant.

24. The process according to claim 21, wherein said sequence of interest is capable of replicating or of replicating and expressing systemically in parts of said plant not provided with both said RNA replicon (i) and said helper replicon (ii).

25. The process according to claim 21, wherein said plant is a dicot plant.

26. A system for replicating or for replicating and expressing a sequence of interest in a plant, comprising:
- (i) a DNA precursor of an RNA replicon, said RNA replicon derived from a tobamovirus and comprising at least one sequence of interest, said DNA precursor of said RNA replicon containing one or more introns in a tobamoviral replicase ORF of said RNA replicon, wherein said one or more introns are inserted within A/U rich localities of said tobamoviral replicase ORF; and
- (ii) a DNA precursor of a helper replicon, wherein said helper replicon is
  - (a) incapable of systemic movement in a plant both in the presence and in the absence of said RNA replicon (i) and
  - (b) capable of expressing in a plant or more proteins necessary for systemic movement of said RNA replicon (i),
- whereby said RNA replicon (i) is capable of replication or of replicating and expressing said sequence of interest in a plant, but unable to move systemically in a plant in the absence of said one or more proteins expressed by said helper replicon (ii).

* * * * *

UNITED STATES PATENT AND TRADEMARK OFFICE
CERTIFICATE OF CORRECTION

PATENT NO. : 8,597,950 B2
APPLICATION NO. : 10/586998
DATED : December 3, 2013
INVENTOR(S) : Sylvestre Marillonnet et al.

Page 1 of 1

It is certified that error appears in the above-identified patent and that said Letters Patent is hereby corrected as shown below:

In the Claims

Column 63:
Line 38 "(b) capable of expressing in a plant or more proteins", should read --(b) capable of expressing in a plant one or more proteins--

Column 65:
Line 19 "(b) capable of expressing in a plant or more proteins", should read --(b) capable of expressing in a plant one or more proteins--

Column 66:
Line 24 "(b) capable of expressing in a plant or more proteins", should read --(b) capable of expressing in a plant one or more proteins--

Signed and Sealed this
Twenty-first Day of April, 2015

Michelle K. Lee
*Director of the United States Patent and Trademark Office*

SEQUENCE LISTING

<160> NUMBER OF SEQ ID NOS: 20

<210> SEQ ID NO 1
<211> LENGTH: 124
<212> TYPE: DNA
<213> ORGANISM: Artificial Sequence
<220> FEATURE:
<223> OTHER INFORMATION: chemically synthesized

<400> SEQUENCE: 1
gtaaatcctg gtccacactt ttacgataaa aacacaagat tttaaactat gaactgatca     60
ataatcattc ctaaaagacc acactttgt tttgtttcta aagtaatttt tactgttata    120
acag                                                                 124

<210> SEQ ID NO 2
<211> LENGTH: 136
<212> TYPE: DNA
<213> ORGANISM: Artificial Sequence
<220> FEATURE:
<223> OTHER INFORMATION: chemically synthesized

<400> SEQUENCE: 2
gtaagaggtc aaaaggtttc cgcaatgatc cctctttttt tgtttctcta gtttcaagaa     60
tttgggtata tgactaactt ctgagtgttc cttgatgcat atttgtgatg agacaaatgt    120
ttgttctatg ttttag                                                    136

<210> SEQ ID NO 3
<211> LENGTH: 150
<212> TYPE: DNA
<213> ORGANISM: Artificial Sequence
<220> FEATURE:
<223> OTHER INFORMATION: chemically synthesized

<400> SEQUENCE: 3
gtaagttctg catttggtta tgctccttgc attttaggtg ttcgtcgctc ttccatttcc     60
atgaatagct aagatttttt ttctctgcat tcattcttct tgcctcagtt ctaactgttt    120
gtggtatttt tgttttaatt attgctacag                                     150

<210> SEQ ID NO 4
<211> LENGTH: 121
<212> TYPE: DNA

<213> ORGANISM: Artificial Sequence
<220> FEATURE:
<223> OTHER INFORMATION: chemically synthesized

<400> SEQUENCE: 4

```
gtaaagcaac tgtgttttaa tcaatttctt gtcaggatat atggattata acttaatttt      60
tgagaaatct gtagtatttg gcgtgaaatg agtttgcttt ttggtttctc ccgtgttata     120
g                                                                    121
```

<210> SEQ ID NO 5
<211> LENGTH: 136
<212> TYPE: DNA
<213> ORGANISM: Artificial Sequence
<220> FEATURE:
<223> OTHER INFORMATION: chemically synthesized

<400> SEQUENCE: 5

```
gtaaagtttc caactttcct ttaccatatc aaactaaagt tcgaaacttt ttatttgatc      60
aacttcaagg ccacccgatc tttctattcc tgattaattt gtgatgaatc catattgact    120
tttgatggtt acgcag                                                    136
```

<210> SEQ ID NO 6
<211> LENGTH: 121
<212> TYPE: DNA
<213> ORGANISM: Artificial Sequence
<220> FEATURE:
<223> OTHER INFORMATION: chemically synthesized

<400> SEQUENCE: 6

```
gtctgtcttt cctatttcat atgtttaatc ctaggaattt gatcaattga ttgtatgtat      60
gtcgatccca agactttctt gttcacttat atcttaactc tctctttgct gtttcttgca    120
g                                                                    121
```

<210> SEQ ID NO 7
<211> LENGTH: 159
<212> TYPE: DNA
<213> ORGANISM: Artificial Sequence
<220> FEATURE:
<223> OTHER INFORMATION: chemically synthesized

<400> SEQUENCE: 7

```
gtaaaatatt ggatgccaga cgatattctt tcttttgatt tgtaactttt tcctgtcaag      60
gtcgataaat tttatttttt ttggtaaaag gtcgataatt ttttttggga gccattatgt    120
aattttccta attaactgaa ccaaaattat acaaaccag                           159
```

<210> SEQ ID NO 8
<211> LENGTH: 109
<212> TYPE: DNA
<213> ORGANISM: Artificial Sequence
<220> FEATURE:
<223> OTHER INFORMATION: chemically synthesized

<400> SEQUENCE: 8

```
gtaaggactt ctcatgaata ttagtggcag attagtgttg ttaaagtctt tggttagata      60
atcgatgcct cctaattgtc catgttttac tggttttcta caattaaag               109
```

<210> SEQ ID NO 9
<211> LENGTH: 117
<212> TYPE: DNA
<213> ORGANISM: Artificial Sequence
<220> FEATURE:

<223> OTHER INFORMATION: chemically synthesized

<400> SEQUENCE: 9

| | |
|---|---|
| gtgagttcct aagttccatt tttttgtaat ccttcaatgt tatttaact tttcagatca | 60 |
| acatcaaaat taggttcaat tttcatcaac caaataatat ttttcatgta tatatag | 117 |

<210> SEQ ID NO 10
<211> LENGTH: 158
<212> TYPE: DNA
<213> ORGANISM: Artificial Sequence
<220> FEATURE:
<223> OTHER INFORMATION: chemically synthesized

<400> SEQUENCE: 10

| | |
|---|---|
| gtaagttttt ccactttaag aaaattacta gcactaaatt tacgaatttt aactatacaa | 60 |
| ttatggatgt aaccaccatt ttaaattaat cttgaaccag acgatatgga ttacaaacat | 120 |
| tcttgtttta atcggctggt tagctattgc atttgcag | 158 |

<210> SEQ ID NO 11
<211> LENGTH: 130
<212> TYPE: DNA
<213> ORGANISM: Artificial Sequence
<220> FEATURE:
<223> OTHER INFORMATION: chemically synthesized

<400> SEQUENCE: 11

| | |
|---|---|
| gtaaggattt ttatgatata gtatgcttat gtattttgta ctgaaagcat atcctgcttc | 60 |
| attgggatat tactgaaagc atttaactac atgtaaactc acttgatgat caataaactt | 120 |
| gattttgcag | 130 |

<210> SEQ ID NO 12
<211> LENGTH: 126
<212> TYPE: DNA
<213> ORGANISM: Artificial Sequence
<220> FEATURE:
<223> OTHER INFORMATION: chemically synthesized

<400> SEQUENCE: 12

| | |
|---|---|
| gtaagccatc ttcctgctta tttttataat gaacatagaa ataggaagtt gtgcagagaa | 60 |
| actaattaac ctgactcaaa atctacccctc ataattgttg tttgatattg gtcttgtatt | 120 |
| ttgcag | 126 |

<210> SEQ ID NO 13
<211> LENGTH: 301
<212> TYPE: DNA
<213> ORGANISM: Artificial Sequence
<220> FEATURE:
<223> OTHER INFORMATION: chemically synthesized

<400> SEQUENCE: 13

| | |
|---|---|
| cggacgatac gtgatccacc atgatagagg agccattgtg tattacgatc cgcttaaact | 60 |
| aatatctaag ctcggctgca agcacatcag agacgtcgtg cacttagaag agttacgcga | 120 |
| gtctttgtgc gacgtagcta gtaacttgaa caactgcgcc tacttctcac agttagatga | 180 |
| ggccgttgct gaggtccaca agactgcggt cggaggctcc ttcgcgttct gtagcatcat | 240 |
| caaatacttg tcagacaaga ggctgttcag ggacctgttc ttcgtctgag ttgacgaatt | 300 |
| c | 301 |

<210> SEQ ID NO 14

```
<211> LENGTH: 538
<212> TYPE: DNA
<213> ORGANISM: Artificial Sequence
<220> FEATURE:
<223> OTHER INFORMATION: chemically synthesized

<400> SEQUENCE: 14
ccatggacaa agtgataaag gcagctttt  gtggagacga tagcctgatt tacattccta      60
aaggtttaga cttgcctgat attcaggcgg gcgcgaacct catgtggaac ttcgaggcca     120
aactcttcag gaagaagtat ggttacttct gtggtcgtta tgttattcac catgatagag     180
gagccattgt gtattacgat ccgcttaaac taatatctaa gttaggttgt aaacatatta     240
gagatgttgt tcacttagaa gagttacgcg agtctttgtg tgatgtagct agtaacttaa     300
ataattgtgc gtattttca cagttagatg aggccgttgc cgaggttcat aagaccgcgg      360
taggcggttc gtttgctttt tgtagtataa ttaagtattt gtcagataag agattgttta     420
gagatttgtt ctttgtttga taatgtcgat agtctcgtac gaacctaagg tgagtgattt     480
cctcaatctt tcgaagaagg aagagatctt gccgaaggct ctaacgaggt tagaattc      538

<210> SEQ ID NO 15
<211> LENGTH: 636
<212> TYPE: DNA
<213> ORGANISM: Artificial Sequence
<220> FEATURE:
<223> OTHER INFORMATION: chemically synthesized

<400> SEQUENCE: 15
ggagataacc tgagcttctt cttccataat gagagcactc tcaattacac ccacagcttc      60
agcaacatca tcaagtacgt gtgcaagacg ttcttccctg ctagtcaacg cttcgtgtac     120
cacaaggagt tcctggtcac tagagtcaac acttggtact gcaagttcac gagagtggat     180
acgttcactc tgttccgtgg tgtgtaccac aacaatgtgg attgcgaaga gttttacaag     240
gctatggacg atgcgtggca ctacaaaag acgttagcaa tgcttaatgc cgagaggacc      300
atcttcaagg ataacgctgc gttaaacttt tggttcccga agtgagagaa catggttatc     360
gtccctctct tgacgcttc tatcacaact ggtaggatgt ctaggagaga ggttatggtg      420
aacaaggact tcgtctacac ggtcctaaat cacatcaaga cctatcaagc taaggcactg     480
acgtacgcaa acgtgctgag cttcgtggag tctattaggg ctagagtcat aattaacggt     540
gtcactgcca ggtctgaatg ggacacagac aaggcaattc taggtccatt agcaatgaca     600
ttcttcctga tcacgaagct gggtcatgtg caagat                               636

<210> SEQ ID NO 16
<211> LENGTH: 297
<212> TYPE: DNA
<213> ORGANISM: Artificial Sequence
<220> FEATURE:
<223> OTHER INFORMATION: chemically synthesized

<400> SEQUENCE: 16
gcggacgata cgtgatccac catgatagag gagccattgt gtattacgat ccgcttaaac      60
taatatctaa gctcggctgc aagcacatca gagacgtcgt gcacttagaa gagttacgcg     120
agtctttgtg cgacgtagct agtaacttga acaactgcgc ctacttctca cagttagatg     180
aggccgttgc tgaggtccac aagactgcgg tcggaggctc cttcgcgttc tgtagcatca     240
tcaaatactt gtcagacaag aggctgttca gggacctgtt cttcgtctga gttgacg       297

<210> SEQ ID NO 17
```

```
<211> LENGTH: 1419
<212> TYPE: DNA
<213> ORGANISM: Artificial Sequence
<220> FEATURE:
<223> OTHER INFORMATION: genetically engineered sequence containing
      fragment derived from Arabidopsis thaliana

<400> SEQUENCE: 17
cccgagctat actgtacctt cgccgaccga ttggtactac agtacaagaa ggcggaggag      60
ttccaatcgt gtgatctttc caaacctcta gaagagtcag agaagtacta caacgcatta     120
tccgagctat cagtgcttga gaatctcgac tcttttgact tagaggcgtt taagacttta     180
tgtcagcaga agaatgtgga cccggatatg gcagcaaagg taaatcctgg tccacacttt     240
tacgataaaa acacaagatt ttaaactatg aactgatcaa taatcattcc taaaagacca     300
cacttttgtt ttgtttctaa agtaattttt actgttataa caggtggtcg tagcaatcat     360
gaagtcagaa ttgacgttgc ctttcaagaa acctacagaa gaggaaatct cggagtcgct     420
aaaaccagga gagggtcgt gtgcagagca taaggaagtg ttgagcttac aaaatgatgc     480
tccgttcccg tgtgtgaaaa atctagttga aggttccgtg ccggcgtatg aatgtgtcc      540 taagggtggt ggtttcgaca aattggatgt ggacattgct gatttccatc tcaagagtgt     600
agatgcagtt aaaaagggaa ctatgatgtc tgcggtgtac acagggtcta tcaaagttca     660
acaaatgaag aactacatag attacttaag tgcgtcgctg gcagctacag tctcaaacct     720
ctgcaaggta agaggtcaaa aggtttccgc aatgatccct ctttttttgt ttctctagtt     780
tcaagaattt gggtatatga ctaacttctg agtgttcctt gatgcatatt tgtgatgaga     840
caaatgtttg ttctatgttt taggtgctta gagatgttca cggcgttgac ccagagtcac     900
aggagaaatc tggagtgtgg gatgttagga gaggacgttg gttacttaaa cctaatgcga     960
aaagtcacgc gtggggtgtg gcagaagacg ccaaccacaa gttggttatt gtgttactca    1020
actgggatga cggaaagccg gtttgtgatg agacatggtt cagggtggcg gtgtcaagcg    1080
attccttgat atattcggat atgggaaaac ttaagacgct cacgtcttgc agtccaaatg    1140
gtgagccacc ggagcctaac gccaaagtaa ttttggtcga tggtgttccc ggttgtggaa    1200
aaacgaagga gattatcgaa aaggtaagtt ctgcatttgg ttatgctcct tgcatttag     1260 gtgttcgtcg ctcttccatt tccatgaata gctaagattt ttttctctg cattcattct     1320 tcttgcctca gttctaactg tttgtggtat ttttgtttta attattgcta caggtaaact    1380
tctctgaaga cttgatttta gtccctggga aggaagctt                           1419

<210> SEQ ID NO 18
<211> LENGTH: 1159
<212> TYPE: DNA
<213> ORGANISM: Artificial Sequence
<220> FEATURE:
<223> OTHER INFORMATION: genetically engineered sequence containing
      fragment derived from Arabidopsis thaliana

<400> SEQUENCE: 18
ctgcaggtaa aatattggat gccagacgat attctttctt ttgatttgta acttttttcct      60 gtcaaggtcg ataaatttta ttttttttgg taaaaggtcg ataatttttt tttggagcca     120
ttatgtaatt ttcctaatta actgaaccaa aattatacaa accaggtttg ctggaaaatt     180
tggttgcaat gatcaaaaga aacatgaatg cgccggattt gacagggaca attgacattg     240
aggatactgc atctctggtg gttgaaaagt tttgggattc gtatgttgac aaggaattta     300
gtggaacgaa cgaaatgacc atgacaaggg agagcttctc caggtaagga cttctcatga     360
```

-continued

| | |
|---|---|
| atattagtgg cagattagtg ttgttaaagt ctttggttag ataatcgatg cctcctaatt | 420 |
| gtccatgttt tactggtttt ctacaattaa aggtggcttt cgaaacaaga gtcatctaca | 480 |
| gttggtcagt tagcggactt taactttgtg gatttgccgg cagtagatga gtacaagcat | 540 |
| atgatcaaga gtcaaccaaa gcaaaagtta gacttgagta ttcaagacga atatcctgca | 600 |
| ttgcagacga tagtctacca ttcgaaaaag atcaatgcga ttttcggtcc aatgttttca | 660 |
| gaacttacga ggatgttact cgaaaggatt gactcttcga gtttctgtt ctacaccaga | 720 |
| aagacacctg cacaaataga ggacttcttt tctgacctag actcaaccca ggcgatggaa | 780 |
| attctggaac tcgacatttc gaagtacgat aagtcacaaa acgagttcca ttgtgctgta | 840 |
| gagtacaaga tctgggaaaa gttaggaatt gatgagtggc tagctgaggt ctggaaacaa | 900 |
| ggtgagttcc taagttccat tttttgtaa tccttcaatg ttattttaac ttttcagatc | 960 |
| aacatcaaaa ttaggttcaa ttttcatcaa ccaaataata tttttcatgt atatataggt | 1020 |
| cacagaaaaa cgaccttgaa agattatacg gccggaatca aaacatgtct ttggtatcaa | 1080 |
| aggaaaagtg gtgatgtgac aacctttatt ggtaatacca tcatcattgc cgcatgtttg | 1140 |
| agctcaatga tccccatgg | 1159 |

<210> SEQ ID NO 19
<211> LENGTH: 1548
<212> TYPE: DNA
<213> ORGANISM: Artificial Sequence
<220> FEATURE:
<223> OTHER INFORMATION: genetically engineered

<400> SEQUENCE: 19

| | |
|---|---|
| gttttagttt tattgcaaca acaacaacaa attacaataa caacaaacaa aatacaaaca | 60 |
| acaacaacat ggcacaattt caacaaacaa ttgacatgca aactctccaa gccgctgcgg | 120 |
| gacgcaacag cttggtgaat gatttggcat ctcgtcgcgt ttacgataat gcagtcgagg | 180 |
| agctgaatgc tcgttccaga cgtcccaagg taaaacaaca tttcattcac atatatgaat | 240 |
| acttttgtca ttgagtacga agaagacact tactacttgt tgatgaaagt ttccgccttt | 300 |
| atacttatct atatcatttt catcatttca aactagtatg aaattaggtg atgtttatat | 360 |
| gatatcatgg aacattaatc tatagggaaa ctgttttgag ttagttttgt ataatatttt | 420 |
| tccctgtttg atgttaggtt catttctcca aggcagtgtc tacggaacag acactgattg | 480 |
| caacaaacgc atatccggag ttcgagattt cctttactca tacgcaatcc gctgtgcact | 540 |
| ccttggccgg aggccttcgg tcacttgagt tggagtatct catgatgcaa gttccgttcg | 600 |
| gctctctgac ctacgacatc ggcggaaact tctccgcgca cctcttcaaa ggtaattttc | 660 |
| tttctctact caatttttctc caagatccaa tatttgaaga ctgatctata gttaaaatta | 720 |
| atctctactc cattcttgtt acctcaggtc gcgattacgt tcactgctgc atgcgtttta | 780 |
| gtttattgc aacaacaaca acaaattaca ataacaacaa acaaaataca acaacaaca | 840 |
| acatggcaca atttcaacaa acaattgaca tgcaaactct ccaagccgct gcgggacgca | 900 |
| acagcttggt gaatgatttg gcatctcgtc gcgtttacga taatgcagtc gaggagctga | 960 |
| atgctcgttc cagacgtccc aaggtaaaac aacatttcat tcacatatat gaatactttt | 1020 |
| gtcattgagt acgaagaaga cacttactac ttgttgatga agtttccgc ctttatactt | 1080 |
| atctatatca ttttcatcat ttcaaactag tatgaaatta ggtgatgttt atatgatatc | 1140 |
| atggaacatt aatctatagg gaaactgttt tgagttagtt ttgtataata ttttccctg | 1200 |
| tttgatgtta ggttcatttc tccaaggcag tgtctacgga acagacactg attgcaacaa | 1260 |

```
acgcatatcc ggagttcgag atttccttta ctcatacgca atccgctgtg cactccttgg   1320
ccggaggcct tcggtcactt gagttggagt atctcatgat gcaagttccg ttcggctctc   1380
tgacctacga catcggcgga aacttctccg cgcacctctt caaaggtaat tttctttctc   1440
tactcaattt tctccaagat ccaatatttg aagactgatc tatagttaaa attaatctct   1500
actccattct tgttacctca ggtcgcgatt acgttcactg ctgcatgc                1548
```

<210> SEQ ID NO 20
<211> LENGTH: 9573
<212> TYPE: DNA
<213> ORGANISM: Artificial Sequence
<220> FEATURE:
<223> OTHER INFORMATION: genetically engineered

<400> SEQUENCE: 20

```
tggcaggata tattgtggtg taaacaaatt gacgcttaga caacttaata acacattgcg     60
gacgttttta atgtactggg gtggatgcag gtcgatctag taacatagat gacaccgcgc    120
gcgataattt atcctagttt gcgcgctata ttttgttttc tatcgcgtat aaatgtata    180 attgcgggac tctaatcata aaacccatc tcataaataa cgtcatgcat tacatgttaa    240
ttattacatg cttaacgtaa ttcaacagaa attatatgat aatcatcgca agaccggcaa    300
caggattcaa tcttaagaaa ctttattgcc aaatgtttga acgatctgct tgactctaga    360
tccagagtcc cgctcagaag aactcgtcaa gaaggcgata gaaggcgatg cgctgcgaat    420
cgggagcggc gataccgtaa agcacgagga agcggtcagc ccattcgccg ccaagctctt    480
cagcaatatc acgggtagcc aacgctatgt cctgatagcg gtccgccaca cccagccggc    540
cacagtcgat gaatccagaa aagcggccat tttccaccat gatattcggc aagcaggcat    600
cgccatgagt cacgacgaga tcctcgccgt cgggcatacg cgccttgagc ctggcgaaca    660
gttcggctgg cgcgagcccc tgatgctctt cgtccagatc atcctgatcg acaagaccgg    720
cttccatccg agtacgtgct cgctcgatgc gatgtttcgc ttggtggtcg aatgggcagg    780
tagccggatc aagcgtatgc agccgccgca ttgcatcagc catgatggat actttctcgg    840
caggagcaag gtgagatgac aggagatcct gccccggcac ttcgcccaat agcagccagt    900
ccctttccgc ttcagtgaca acgtcgagca gctgcgca aggaacgccc gtcgtggcca    960
gccacgatag ccgcgctgcc tcgtcctgga gttcattcag ggcaccggac aggtcggtct   1020
tgacaaaaag aaccgggcgc ccctgcgctg acagccggaa cacggcggca tcagagcagc   1080
cgattgtctg ttgtgcccag tcatagccga atagcctctc cacccaagcg gccggagaac   1140
ctgcgtgcaa tccatcttgt tcaatcatgc gaaacgatcc agatccggtg cagattattt   1200
ggattgagag tgaatatgag actctaattg gataccgagg ggaatttatg gaacgtcagt   1260
ggagcatttt tgacaagaaa tatttgctag ctgatagtga ccttaggcga cttttgaacg   1320
cgcaataatg gttctgacg tatgtgctta gctcattaaa ctccagaaac ccgcggctga   1380
gtggctcctt caacgttgcg gttctgtcag ttccaaacgt aaaacggctt gtcccgcgtc   1440
atcggcgggg gtcataacgt gactccctta attctccgct catggtacca gcttctcgag   1500
cgaccctacg cccccaactg agagaactca aaggttaccc cagttggggc acaacaaaaa   1560
tcaaatctaa atttgtgtaa ttatgaaaat gaaacttacc tttgaagagg tgcgcggaga   1620
agtttccgcc gatgtcgtag gtcagagagc cgaacggaac ttgcatcatg agatactcca   1680
actcaagtga ccgaaggcct ccggccaagg agtgcacagc ggattgcgta tgagtaaagg   1740
aaatctcgaa ctccggatat gcgtttgttg caatcagtgt ctgttccgta gacactgcct   1800
```

```
tggagaaatg aaccttggga cgtctggaac gagcattcag ctcctcgact gcattatcgt   1860
aaacgcgacg agatgccaaa tcattcacca agctgttgcg tcccgcagcg gcttggagag   1920
tttgcatgtc aattgtttgt tgaaattgtg ccatgttgtt gttgtttgta ttttgtttgt   1980
tgttattgta atttgttgtt gttgttgcaa taaaactaaa acttcaaagc ggagaggaaa   2040
atatatgaat ttatataggc gggtttatct cttacaactt tattttcggc ctttcaaaaa   2100
aataattaaa atcgacagac acgaatcatt tcgaccacga gtaaagataa cgtgacctgg   2160
ctgtcagaca gccttttccc tcgtgttaac taattttta actaattaat catctcagcc   2220
cttggattag ttcttttgct ttgatggctt catgactgtg acctgctcga tccgcgtgtt   2280
acatgacagc tccgtttttt tagtggttaa cttaaaccga gtcaatccag gcaacgttag   2340
tcgtcgtcgt ggttggcttg ttcaattaga tttcatacaa ttcaacgtaa tttaattcgt   2400
tttctattag aattgtatca taattaattc agaccgtgaa agaaagtgtc tttcatgatg   2460
tgtttatgga tatttataca ataagataca atgtttcatc atattcacta ttcacgatta   2520
gtatgtacat taaataatgg ctactactac atccgaactc gtcaaaacga ttctgaatca   2580
attatacata tgctgactct tgcatacata aaaaatagtt gtttaaattt tgtctaacta   2640
atgtttggta taagtataat gttgagttga gataccaatt acatcgagtc tagccatttt   2700
gtcgtgccat attcgtcaaa actttcttac ataatgataa cctagatcta gatgagatat   2760
gtatcaatgt atttgagatc ataattaagt tcgttctaaa ttttgtcgaa acgcgtggta   2820
cgctgcagaa ttgctcgaag ccgcggtgcg ggtgccaggg cgtgcccttg gctccccgg    2880 gcgcgtactc cacctcaccc atcttttatt acatgtttga acttcaacaa tttatgactt   2940
tttgttctta ttgttgcagg tcgcgattac gttcactgct gcatgcctaa tctggatgta   3000
cgtgacattg ctcgccatga aggacacaag gaagctattt acagttatgt gaatcgtttg   3060
aaaaggcagc agcgtcctgt gcctgaatac cagagggcag ctttcaacaa ctacgctgag   3120
aacccgcact tcgtccattg cgacaaacct ttccaacagt gtgaattgac gacagcgtat   3180
ggcactgaca cctacgctgt agctctccat agcatttatg atatccctgt tgaggagttc   3240
ggttctgcgc tactcaggaa gaatgtgaaa acttgtttcg cggcctttca tttccatgag   3300
aatatgcttc tagattgtga tacagtcaca ctcgatgaga ttggagctac ttttcagaag   3360
tccggtgata atttaagttt tttctttcat aatgagagca ctctcaatta cacccacagt   3420
tttagtaata taattaagta tgtgtgtaaa acgttctttc ctgctagtca acggtttgtg   3480
tatcataagg agttttagt tactagagtc aacacttggt actgtaagtt tacgagagtg   3540 gatacttta ctcttttccg tggtgtgtac cataataatg tggattgcga agagttttac   3600
aaggctatgg acgatgcgtg gcactacaaa agacgttag caatgcttaa tgccgagagg   3660
accatcttca aggataacgc tgcgttaaac ttttggttcc cgaaagtgag agacatggtt   3720
atcgtccctc tctttgacgc ttctatcaca actggtagga tgtctaggag agagattatg   3780
gtgaacaagg atttcgttta tacggtccta atcacataa aaacgtatca agctaaggct   3840
ttaacttacg caaatgttct gtcctttgtg gagtctatta ggtctagagt gataattaac   3900
ggtgtcactg ccaggtctga atgggacaca gacaaggcaa ttctaggtcc attagcaatg   3960 acattttcc ttataacaaa gttgggtcat gtgcaggatg aaataatcct gaaaagttc    4020 cagaagttcg acagaaccac caatgagctg atttggacaa gtctctgcga tgccctgatg   4080
ggggttattc cctcggtcaa ggagacgctt gtgcgcggtg gttttgtgaa agtagcagaa   4140
caagccttag agataaaggt tcccgagcta tactgtacct tgccgacag attggtacta    4200
```

```
cagtacaaga aggcggagga gttccaatcg tgtgatcttt ccaaacctct agaagagtca    4260
gagaagtact acaacgcatt atccgagcta tcagtgcttg agaatctcga ctcttttgac    4320
ttagaggcgt ttaagacttt atgtcagcag aagaatgtgg acccggatat ggcagcaaag    4380
gtggtcgtag caatcatgaa gtcagaattg acgttgcctt tcaagaaacc tacagaagag    4440
gaaatctcgg agtcgctaaa accaggagag gggtcgtgtg cagagcataa ggaagtgttg    4500
agcttacaaa atgatgctcc gttcccgtgt gtgaaaaatc tagttgaagg ttccgtgccg    4560
gcgtatggaa tgtgtcctaa gggtggtggt ttcgacaaat tggatgtgga cattgctgat    4620
ttccatctca agagtgtaga tgcagttaaa aagggaacta tgatgtctgc ggtgtacaca    4680
gggtctatca aagttcaaca aatgaagaac tacatagatt acttaagtgc gtcgctggca    4740
gctacagtct caaacctctg caaggtgctt agagatgttc acggcgttga cccagagtca    4800
caggagaaat ctggagtgtg ggatgttagg agaggacgtt ggttacttaa acctaatgcg    4860
aaaagtcacg cgtgggggtgt ggcagaagac gccaaccaca agttggttat tgtgttactc    4920
aactgggatg acggaaagcc ggtttgtgat gagacatggt tcagggtggc ggtgtcaagc    4980
gattccttga tatattcgga tatgggaaaa cttaagacgc tcacgtcttg cagtccaaat    5040
ggtgagccac cggagcctaa cgccaaagta attttggtcg atggtgttcc cggttgtgga    5100
aaaacgaagg agattatcga aaaggtaaac ttctctgaag acttgatttt agtccctggg    5160
aaggaagctt ctaagatgat catccggagg gccaaccaag ctggtgtgat aagagcggat    5220
aaggacaatg ttagaacggt ggattccttc ttgatgcatc cttctagaag ggtgttaag    5280 aggttgttta tcgatgaagg actaatgctg catacaggtt gtgtaaattt cctactgctg    5340
ctatctcaat gtgacgtcgc atatgtgtat ggggacacaa agcaaattcc gttcatttgc    5400
agagtcgcga actttccgta tccagcgcat tttgcaaaac tcgtcgctga tgagaaggag    5460
gttagaagag ttacgctcag gtgcccggct gatgttacgt atttccttaa caagaagtat    5520
gacggggcgg tgatgtgtac cagcgcggta gagagatccg tgaaggcaga agtggtgaga    5580
ggaaagggtg cattgaaccc aataaccttta ccgttggagg gtaaaatttt gaccttcaca    5640
caagctgaca agttcgagtt actggagaag ggttacaagg atgtgaacac tgtgcacgag    5700
gtgcaagggg agacgtacga gaagactgct attgtgcgct tgacatcaac tccgttagag    5760
atcatatcga gtgcgtcacc tcatgttttg gtggcgctga caagacacac aacgtgttgt    5820
aaatattaca ccgttgtgtt ggacccgatg gtgaatgtga tttcagaaat ggagaagttg    5880
tccaatttcc ttcttgacat gtatagagtt gaagcggggg tccaatagca attacagatc    5940
gatgcagtat tcagggacag caacttgttt gttcagacgc ccaagtcagg agattggcga    6000
gatatgcaat tttactatga cgctcttctt cccggaaaca gtactattct caatgaattt    6060
gatgctgtta cgatgaattt gagggatatt tccttaaacg tcaaagattg cagaatcgac    6120
ttctccaaat ccgtgcaact tcctaaagaa caacctattt tcctcaagcc taaaataaga    6180
actgcggcag aaatgccgag aactgcaggt ttgctggaaa atttggttgc aatgatcaaa    6240
agaaacatga atgcgccgga tttgacaggg acaattgaca ttgaggatac tgcatctctg    6300
gtggttgaaa agttttggga ttcgtatgtt gacaaggaat ttagtggaac gaacgaaatg    6360
accatgacaa gggaaagttt ttctagatgg ctttcgaaac aagagtcatc tacagttggt    6420
cagttagcgg actttaactt tgtggatttg ccggcagtag atgagtacaa gcatatgatc    6480
aagagtcaac caaagcaaaa gttagacttg agtattcaag acgaatatcc tgcattgcag    6540
acgatagtct accattcgaa aaagatcaat gcgattttcg gtccaatgtt ttcagaactt    6600
```

```
acgaggatgt tactcgaaag gattgactct tcgaagtttc tgttctacac cagaaagaca   6660
cctgcacaaa tagaggactt cttttctgac ctagactcaa cccaggcgat ggaaattctg   6720
gaactcgaca tttcgaagta cgataagtca caaaacgagt tccattgtgc tgtagagtac   6780
aagatctggg aaaagttagg aattgatgag tggctagctg aggtatggaa acaaggacac   6840
agaaaaacga ccttgaaaga ttatacggcc ggagtcaaaa catgtctttg gtatcaaagg   6900
aaaagtggtg atgtgacaac ctttattggt aataccatca tcattgcagc ctgtttgagc   6960
tcaatgatcc ccatggacaa agtgataaag gcagcttttt gtggagacga tagcctgatt   7020
tacattccta aaggtttaga cttgcctgat attcaggcgg cgcgaaacct catgtggaac   7080
ttcgaggcca aactcttcag gaagaagtat ggttacttct gtggtcgtta tgttattcac   7140
catgatagag gagccattgt gtattacgat ccgcttaaac taatatctaa gttaggttgt   7200
aaacatatta gagatgttgt tcacttagaa gagttacgcg agtctttgtg tgatgtagct   7260
agtaacttaa ataattgtgc gtattttca cagttagatg aggccgttgc cgaggttcat    7320
aagaccgcgg taggcggttc gtttgctttt tgtagtataa ttaagtattt gtcagataag   7380
agattgttta gagatttgtt cttgtttga taatgtcgat agtctcgtac gaacctaagg    7440
tgagtgattt cctcaatctt tcgaagaagg aagagatctt gccgaaggct ctaacgaggt   7500
taaaaaccgt gtctattagt actaaagata ttatatctgt caaggagtcg agactttgt    7560 gtgatataga tttgttaatc aatgtgccat tagataagta tagatatgtg ggtatcctag   7620
gagctgtttt taccggagag tggctagtgc cagacttcgt taaaggtgga gtgacgataa   7680
gtgtgataga taagcgtctg gtgaactcaa aggagtgcgt gattggtacg tacagagccg   7740
cagccaagag taagaggttc cagttcaaat tggttccaaa ttactttgtg tccaccgtgg   7800
acgcaaagag gaagccgtgg caggttcatg ttcgtataca agacttgaag attgaggcgg   7860
gttggcagcc gttagctctg gaagtagttt cagttgctat ggtcaccaat aacgttgtca   7920
tgaagggttt gagggaaaag gtcgtcgcaa taaatgatcc ggacgtcgaa ggtttcgaag   7980
gtgtggttga cgaattcgtc gattcggttg cagcatttaa agcggttgac aactttaaaa   8040
gaaggaaaaa gaaggttgaa gaaaagggtg tagtaagtaa gtataagtac agaccggaga   8100
agtacgccgg tcctgattcg tttaatttga aagaagaaaa cgtcttacaa cattacaaac   8160
ccgaataatc gataactcga gtatttttac aacaattacc aacaacaaca aacaacaaac   8220
aacattacaa ttacatttac aattatcatg gtgagcaagg gcgaggagct gttcaccggg   8280
gtggtgccca tcctggtcga gctggacggc gacgtaaacg ccacaagtt cagcgtgtcc     8340 ggcgagggcg agggcgatgc cacctacggc aagctgaccc tgaagttcat ctgcaccacc   8400
ggcaagctgc ccgtgccctg gcccaccctc gtgaccacct tcagctacgg cgtgcagtgc   8460
ttcagccgct accccgacca catgaagcag cacgacttct tcaagtccgc catgcccgaa   8520
ggctacgtcc aggagcgcac catcttcttc aaggacgacg gcaactacaa gacccgcgcc   8580
gaggtgaagt tcgagggcga caccctggtg aaccgcatcg agctgaaggg catcgacttc   8640
aaggaggacg gcaacatcct ggggcacaag ctggagtaca actacaacag ccacaacgtc   8700
tatatcatgg ccgacaagca gaagaacggc atcaaggtga acttcaagat ccgccacaac   8760
atcgaggacg gcagcgtgca gctcgccgac cactaccagc agaacacccc catcggcgac   8820
ggccccgtgc tgctgcccga caaccactac ctgagcaccc agtccgccct gagcaaagac   8880
cccaacgaga gcgcgatca catggtcctg ctggagttcg tgaccgccgc cgggatcact    8940
cacggcatgg acgagctgta caagtaaagc ggcccctaga gcgtggtgcg cacgatagcg   9000
```

-continued

```
catagtgttt ttctctccac ttgaatcgaa gagatagact tacggtgtaa atccgtaggg    9060
gtggcgtaaa ccaaattacg caatgttttg ggttccattt aaatcgaaac cccttatttc    9120
ctggatcacc tgttaacgca cgtttgacgt gtattacagt gggaataagt aaaagtgaga    9180
ggttcgaatc ctccctaacc ccgggtaggg gcccagcggc cgctctagct agagtcaagc    9240
agatcgttca aacatttggc aataaagttt cttaagattg aatcctgttg ccggtcttgc    9300
gatgattatc atataatttc tgttgaatta cgttaagcat gtaataatta acatgtaatg    9360
catgacgtta tttatgagat gggtttttat gattagagtc ccgcaattat acatttaata    9420
cgcgatagaa aacaaaatat agcgcgcaaa ctaggataaa ttatcgcgcg cggtgtcatc    9480
tatgttacta gatcgaccag cttagatcag attgtcgttt cccgccttca gtttaaacta    9540
tcagtgtttg acaggatata ttggcgggta aac                                 9573
```